United States Patent
Connell-Crowley et al.

(10) Patent No.: US 11,358,983 B2
(45) Date of Patent: Jun. 14, 2022

(54) METHOD OF PURIFYING GLYCOSYLATED PROTEIN FROM HOST CELL GALECTINS AND OTHER CONTAMINANTS

(71) Applicant: Just-Evotec Biologics, Inc., Seattle, WA (US)

(72) Inventors: Lisa A Connell-Crowley, Seattle, WA (US); Megan J. McClure, Seattle, WA (US); Ronald O. Gillespie, Seattle, WA (US)

(73) Assignee: Just-Evotec Biologics, Inc., Seattle, WA (US)

( * ) Notice: Subject to any disclaimer, the term of this patent is extended or adjusted under 35 U.S.C. 154(b) by 291 days.

(21) Appl. No.: 16/630,458

(22) PCT Filed: Aug. 18, 2018

(86) PCT No.: PCT/US2018/046919
§ 371 (c)(1),
(2) Date: Jan. 12, 2020

(87) PCT Pub. No.: WO2019/036626
PCT Pub. Date: Feb. 21, 2019

(65) Prior Publication Data
US 2021/0163528 A1 Jun. 3, 2021

Related U.S. Application Data

(60) Provisional application No. 62/546,558, filed on Aug. 17, 2017.

(51) Int. Cl.
*C07K 1/22* (2006.01)
*C07K 1/16* (2006.01)
(Continued)

(52) U.S. Cl.
CPC .............. *C07K 1/165* (2013.01); *C07K 14/71* (2013.01); *C07K 1/22* (2013.01); *C07K 1/36* (2013.01); *C07K 2319/30* (2013.01)

(58) Field of Classification Search
CPC . C07K 1/16; C07K 1/165; C07K 1/18; C07K 1/20; C07K 1/22; C07K 1/36;
(Continued)

(56) References Cited

U.S. PATENT DOCUMENTS 5,429,746 A 7/1995 Shadle et al.
6,333,398 B1 12/2001 Blank
(Continued)

FOREIGN PATENT DOCUMENTS

EP 1544299 B1 12/2008
JP 09-509658 A 9/1997
(Continued)

OTHER PUBLICATIONS

WIPO Transmittal of IPRP and IPRP in corresponding PCT/US2018/046919, dated Feb. 27, 2020.
(Continued)

*Primary Examiner* — Jeffrey E. Russel
(74) *Attorney, Agent, or Firm* — Law Offices of Nisan Steinberg

(57) ABSTRACT

A method for purifying a glycosylated recombinant protein of interest from a contaminant is disclosed that is suitable for industrial production purposes to remove galectins and other host cell contaminants, such as metallic cations, from recombinant therapeutic proteins.

9 Claims, 36 Drawing Sheets

Specification includes a Sequence Listing.

(51) Int. Cl.
*C07K 14/71* (2006.01)
*C07K 1/36* (2006.01)

(58) Field of Classification Search
CPC .............. C07K 14/70521; C07K 14/71; C07K 14/7151; C07K 14/7155; C07K 14/755; C07K 16/00; C07K 2319/30; C07K 2319/32; C07K 2319/33
See application file for complete search history.

(56) References Cited

U.S. PATENT DOCUMENTS

| | | |
|---|---|---|
| 6,797,814 B2 | 9/2004 | Blank |
| 6,870,034 B2 | 3/2005 | Breece et al. |
| 7,070,959 B1 | 7/2006 | Papadopoulos et al. |
| 7,303,746 B2 | 12/2007 | Wiegand et al. |
| 7,303,747 B2 | 12/2007 | Wiegand et al. |
| 7,306,799 B2 | 12/2007 | Wiegand et al. |
| 7,374,757 B2 | 5/2008 | Papadopoulos et al. |
| 7,374,758 B2 | 5/2008 | Papadopoulos et al. |
| 7,427,659 B2 | 9/2008 | Shukla et al. |
| RE41,555 E | 8/2010 | Shadle et al. |
| 7,820,799 B2 | 10/2010 | Godavarti et al. |
| 8,168,185 B2 | 5/2012 | Eon-Duval et al. |
| 8,263,750 B2 | 9/2012 | Shukla et al. |
| 8,343,737 B2 | 1/2013 | Papadopoulos et al. |
| 8,647,842 B2 | 2/2014 | Papadopoulos et al. |
| 8,709,492 B2 | 4/2014 | Teschner et al. |
| 8,895,709 B2 | 11/2014 | Hickman et al. |
| 2003/0153735 A1 | 8/2003 | Breece et al. |
| 2005/0249815 A1 | 11/2005 | Teschner et al. |
| 2008/0317860 A1 | 12/2008 | Senni et al. |
| 2010/0022757 A1 | 1/2010 | Eon-Duval et al. |
| 2010/0135987 A1 | 6/2010 | Hickman et al. |
| 2011/0144311 A1 | 6/2011 | Chmielowski et al. |
| 2012/0149878 A1 | 6/2012 | Gillespie et al. |
| 2012/0202974 A1 | 8/2012 | Eon-Duval et al. |
| 2013/0323788 A1 | 12/2013 | Chen et al. |
| 2016/0251411 A1 | 9/2016 | Burakov et al. |
| 2017/0045527 A1 | 2/2017 | Muthusamy et al. |

FOREIGN PATENT DOCUMENTS

| | | |
|---|---|---|
| JP | 2008-543868 A | 4/2008 |
| JP | 2010-516651 A | 12/2011 |
| JP | 2011-530606 A | 12/2011 |
| WO | 9522389 A1 | 8/1995 |
| WO | 9812225 A2 | 3/1998 |
| WO | 9823645 A1 | 6/1998 |
| WO | 2003066662 A2 | 8/2003 |
| WO | 2006138553 A2 | 12/2006 |
| WO | 2006138553 A3 | 12/2006 |
| WO | 2007109163 A2 | 9/2007 |
| WO | 2008087184 A2 | 7/2008 |
| WO | 2009010271 A2 | 1/2009 |
| WO | 2010019493 A1 | 2/2010 |
| WO | 2010056550 A1 | 5/2010 |
| WO | 2011038894 A1 | 4/2011 |
| WO | 2011073389 A1 | 6/2011 |
| WO | 2012078376 A1 | 6/2012 |
| WO | 2016183222 A1 | 11/2016 |
| WO | 2019036626 A1 | 2/2019 |

OTHER PUBLICATIONS

EPO Rule 161/162 EPC Communication in corresponding European application EP18778588.6, dated Mar. 24, 2020.
EPO Rule 71(3) EPC Communication (Notice of Intention to Grant) and Annex in corresponding European application EP18778588.6, dated Feb. 16, 2021.
Nabila Aboulaich, et al., "A Novel Approach to Monitor Clearance of Host Cell Proteins Associated With Monoclonal Antibodies," Published online Jul. 26, 2014 in Wiley Online Library (wileyonlinelibrary.com).
Mark D. Blostein, et al., "Galectin-3 Binding Protein Contaminates the Purification of Recombinant Factor IX.", Blood Journal, 2006 108:1038, www.bloodjournal.org.content (Abstract only).
Jerka Dumic, et al., "Galectin-3: An open-ended story," Biochimica et Biophysica Acta 1760 (2006) 616-635, online at www.sciencedirect.com, Elsevier.
Benedicte Fournier, et al., "Protein A gene expression in regulated by DNA supercoiling which is modified by the ArlS—ArR two-component system of *Staphylococcus aureus*," Microbiology (2004), 150, 3807-3819.
U.S. Department of Health and Human Services, Food and Drug Administration, Center for Drug Evaluation and Research (CDER) Center for Biologics Evaluation and Research (CBER), "Guidance for Industry, Q5A Viral Safety Evaluation of Biotechnology Products Derived From Cell Lines of Human or Animal Origin," Sep. 1998.
Rachel C. Houp, "Ultrafiltraion and Diafiltration," Journal of Validation Technology, Autum 2009.
G. Joucla, et al., "Cation exchange versus multimodal cation exchange resins for antibody capture from CHO supernatants: Identification of contaminating Host Cell Proteins by mass spectrometry," Journal of Chromatogaphy B 942-943 (2013) 126-133.
Atsuhiro Kanda, et al., "Aflibercept Traps Galectin-1, and Angiogenic Factor Associated with Diabetic Retinopathy," Scientific Reports. 5:17946-DOI: 10.1038/srep17946, published Dec. 9, 2015.
Megan McClure, et al., "Impact of an Iron Contaminant and its Removal During Downstream Processing," Just Biotherapeutics, Inc., one page poster presented to American Chemical Society (ACS) Apr. 2017.
Sofia Nohlden, "Master thesis, Affinity Determination of Protein A Domains to IgG subclasses by Surface Plasmon Resonance," Feb. 22, 2018, Linkoping University Institute of Technology, LiTH-IFM-EX-08/1921-SE.
Richard S. Rogers, et al., "Development of a quantitative mass spectrometry multi-attribute method for characterization, quality control testing and disposition of biologies," mAbs 7:5, 881-890; Sep./Oct. 2015.
European Patent Office, "International Search Report and Written Opinion of the International Searching Authority," re PCT/US2018/046919, dated Nov. 30, 2018.
Aboulaich, Nabila, et al., "A novel approach to monitor clearance of host cell proteins associated with monoclonal antibodies," Biotechnol. Prog. Sep.-Oct. 2014; 30(5):1114-24. doi: 10.1002/btpr.1948. Epub Jul. 26, 2014. (As cited by JPO, Jan. 28, 2022).
Kanda, Atsuhiro, et al., "Aflibercept traps Galectin-1, an Angiogenic Factor Associated with Diabetic Retinopathy," Sci. Rep. Dec. 9, 2015; 5:17946. doi: 10.1038/srep17946. (As cited by JPO, Jan. 28, 2022).
Heyl, Kerstin A., et al., "Galectin-3 binds highly galactosylated IgG1 and is crucial for the IgG1 complex mediated inhibition of C5aReceptor induced immune responses," Biochem. Biophys. Res. Commun. Oct. 7, 2016; 479(1):86-90. doi: 10.1016/j.bbrc.2016.09.038. Epub Sep. 13, 2016. (As cited by JPO, Jan. 28, 2022).
Joucla, G., et al., "Cation exchange versus multimodal cation exchange resins for antibody capture from CHO supernatants: identification of contaminating host cell proteins by mass spectrometry," J. Chromatogr. B Analyt. Technol. Biomed. Life Sci. Dec. 30, 2013; 942-943:126-33. doi: 10.1016/j.jchromb.2013.10.033. Epub Oct. 25, 2013. (As cited by JPO, Jan. 28, 2022).
Patnaik, Santosh Kumar, et al., "Complex N-glycans are the major ligands for galectin-1, -3, and -8 on Chinese hamster ovary cells," Glycobiology Apr. 2006; 16(4):305-317. doi: 10.1093/glycob/cwj063. Epub Nov. 29, 2005. (As cited by JPO, Jan. 28, 2022).
First Office Action by JPO, dated Jan. 28, 2022, in corresponding Japanese Patent Application No. 2020-505786. (Original Japanese language with English translation attached).
Miguelino, Maricel, et al., "Clinical utility and patient perspectives on the use of extended half-life rFIXFc in the management of hemophilia B," Patient Prefer. Adherence Aug. 8, 2014; 8:1073-83. doi: 10.2147/PPA.S54951. eCollection 2014.

(56) References Cited

OTHER PUBLICATIONS

Diao, Lei, et al., "Population pharmacokinetic modelling of recombinant factor IX Fc fusion protein (rFIXFc) in patients with haemophilia B," Clin. Pharmacokinet. May 2014; 53(5):467-77. doi: 10.1007/s40262-013-0129-7.

Astermark, Jan, et al., "Efficacy of rFIXFc versus rIX-FP for the Treatment of Patients with Hemophilia B: Matching-Adjusted Indirect Comparison of B-LONG and PROLONG-9FP Trials," J. Blood Med. Jul. 14, 2021; 12:613-621. doi: 10.2147/JBM.S312885. eCollection 2021.

Vincenti, Flavio, et al., "Belatacept and Long-Term Outcomes in Kidney Transplantation," N. Engl. J. Med. 2016; 374:333-43. DOI: 10.1056/NEJMoa15060.

- MabSelect Sure resin (Bind and elute mode)
- Wash 1 and 3: EQ
- Wash 2: 2M $CaCl_2$
- Elution: 25mM citrate pH 3.6 elution

- Acid titration: 2M citrate to pH 3.5
- Hold 1hr
- Neutralize: 2M Tris base to pH 5.0

- Fractogel $SO_3^-$ resin (Bind and elute mode)
- Operate at pH 5.0
- Elution: Gradient of 15-65% blend of 0 and 1M NaCl buffers over 10 CV

- Butyl 650M resin (Flowthrough mode)
- Operate at pH 5.0 in 400mM NaCl for load and wash

METHOD OF PURIFYING GLYCOSYLATED PROTEIN FROM HOST CELL GALECTINS AND OTHER CONTAMINANTS

This is a U.S. national phase application under 35 U.S.C. § 371 of United States Patent Cooperation Treaty Application No. PCT/US2018/046919, filed Aug. 17, 2018, which claims priority from U.S. Provisional patent Application Ser. No. 62/546,558, filed in the United States Patent and Trademark Office on Aug. 17, 2017, and which incorporates by reference those PCT and Provisional applications in their entireties.

SEQUENCE LISTING

The instant application contains a Sequence Listing which has been filed electronically in ASCII format and is hereby incorporated by reference in its entirety. Said ASCII copy, created on Aug. 14, 2018, is named JUST0381_SL.txt and is 4,148 bytes in size.

BACKGROUND OF THE INVENTION

1. Field of the Invention

This invention relates to methods of purifying recombinantly produced proteins from contaminating host cell proteins and metallic ions.

2. Discussion of the Related Art

Industrial production of recombinant therapeutic proteins requires that contaminating host cell proteins and metallic ions be effectively removed from the protein of interest to meet strict regulatory standards.

When a glycosylated recombinant protein is rich in terminal β-galactosyl residues, purifying the recombinant protein from host cell protein galectins reversibly bound to those galactoside residues is a critical problem.

Galectins are animal lectins that can specifically bind beta-galactosides.

Twelve galectins have been described in vertebrates, belonging to three different subgroups: prototype (e.g., galectin-1, -2, -7, -10, -13, -14), tandem-repeat (e.g., galectin-4, -8, -9, -12) and chimeric galectins (e.g., galectin-3). These galectin proteins reportedly are involved in cellular interactions and neoplastic transformations in host cells. (See, e.g., Cummings R D and Liu F T, Galectins, In: Varki A, Cummings R D, Esko J D, Freeze H H, Stanley P, Bertozzi C R, Hart G W, Etzler M E, editors. Essentials of Glycobiology. 2nd edition. Cold Spring Harbor (N.Y.): Cold Spring Harbor Laboratory Press; 2009. Chapter 33; Gitt, M A et al., *Galectin-4 and galectin-6 are two closely related lectins expressed in mouse gastrointestinal tract*, J Biol Chem. 273(5):2954-60 (1998); Bidon, N. et al., *Galectin-8: a complex sub family of galectins (Review)*, Int J Mol Med. 8(3):245-50 (2001); Hadari, Y R et al., *Galectin-8. A new rat lectin, related to galectin-4*, J Biol Chem. 270(7):3447-53 (1995); Sato, M. et al., *Functional analysis of the carbohydrate recognition domains and a linker peptide of galectin-9 as to eosinophil chemoattractant activity*, Glycobiology 12(3):191-97 (2002); Yang, R Y et al., *Cell cycle regulation by galectin-12, a new member of the galectin superfamily*, J Biol Chem. 276(23):20252-60 (2001); Ramaswamy, S et al., *Structural basis of multivalent galactose-based dendrimer recognition by human galectin-7*, FEBS J. 2015 January; 282(2):372-87 (2015); Patnaik, S K et al., *Complex N-glycans are the major ligands for galectin-1, -3, and-8 on Chinese hamster ovary cells*, Glycobiology 16(4):305-17 (2006)).

Galectin-3 is about 30 kDa in MW and contains a carbohydrate-recognition-binding domain (CRD) of about 130 amino acids that enables the specific binding of β-galactosides. Among the proteins that galectin-3 is reported to bind are laminin, fibronectin, hensin, elastin, collagen IV, tenascin-C, tenascin-R, integrins α1β1, α4β7, α6β1, and αMβ1, VEGFR2, NG2, and aminopeptidase N. (Funasaka et al., *Galectin-3 in angiogenesis and metastasis*, Glycobiology 24 (10): 886-891 (2014)). Host cell protein galectin-3 was reported to be a contaminant of recombinantly produced Factor IX protein. (Blostein et al., *Galectin-3 Binding Protein Contaminates the Purification of Recombinant Factor IX*, Blood 108:1038 (2006).

Aflibercept is another recombinant therapeutic protein, typically rich in terminal beta-galactosyl residues. Aflibercept protein includes two main components: the vascular endothelial growth factor (VEGF) binding portions from the extracellular domains of human VEGF receptors 1 and 2, fused to the Fc portion of human IgG1. (See, Papadopoulos et al., Modified chimeric polypeptides with improved pharmacokinetic properties, WO 00/75319 A1; U.S. Pat. No. 7,070,959B2). The United States Food and Drug Administration (FDA) approved aflibercept for marketing in November 2011, and the European Medicines Agency (EMA) approved in November 2012. Aflibercept, under the brand name Eylea® (Regeneron Pharmaceuticals, Inc.) is used as an ophthalmic agent in the treatment of eye disorders or diseases, e.g., macular edema following Central Retinal Vein Occlusion (CRVO), Central Retinal Vein Occlusion (CRVO), Branch Retinal Vein Occlusion (BRVO), Neovascular (Wet) Age-Related Macular Degeneration (AMD), Impaired vision due to Myopic Choroidal Neovascularisation, Diabetic Macular Edema (DME), Diabetic Retinopathy (DR) in patients with DME, and neovascular Age-Related Macular Degeneration (AMD). Ziv-aflibercept, under the brand name Zaltrap® (Regeneron Pharmaceuticals, Inc.), was developed as an intravenous infusion for treatment of metastatic colorectal cancer.

Structurally, aflibercept is a dimeric glycoprotein with a protein molecular weight of about 96.9 kilo Daltons (kDa). It contains approximately 15% glycosylation to give a total molecular weight of approximately 115 kDa. All five putative N-glycosylation sites on each polypeptide chain predicted by the primary sequence can be occupied with carbohydrate and exhibit some degree of chain heterogeneity, including heterogeneity in terminal sialic acid residues. However, aflibercept produced by CHO cells can be rich in terminal beta-galactosyl residues, the binding target of galectin-3.

An effective and economical method for purifying recombinant proteins to remove galectins and other host cell contaminants, such as metallic cations, and which is suitable for industrial production purposes, is a desideratum that the present invention provides.

SUMMARY OF THE INVENTION

The present invention relates to a method for purifying a glycosylated recombinant protein of interest from a contaminant. The method involves:

(a) loading onto a Protein A matrix, at about neutral pH, a host cell culture supernatant or filtrate comprising the glycosylated recombinant protein of interest (POI) and a galectin host cell protein contaminant, wherein the POI comprises the $C_H2$ and $C_H3$ domains of an immunoglobulin Fc domain and one or more terminal beta-galactosyl residues to which the galectin host cell protein contaminant is reversibly bound;

(b) washing the Protein A matrix that has the POI bound to it, with a buffer at about pH 6.0-6.5, comprising 1-3 M calcium chloride;

(c) eluting the POI from the Protein A matrix with a buffer comprising citric acid or a citrate salt below about pH 4 into an eluant pool, and:
  (i) if the eluant pool is more basic than the pH range of pH 3.3-3.7, titrating the eluant pool to pH 3.3-3.7 with citric acid, and
  (ii) optionally, keeping the eluant pool at pH 3.3-3.7 for a period sufficient for viral inactivation (typically 30-90 minutes, but as needed empirically by virus panel verification of viral inactivation);

(d) binding the POI in the eluant pool from (c) to a cation exchange matrix in a low conductivity buffer of about 2-15 millisiemens (mS), at pH 5.0-5.5;

(e) eluting the POI from the cation exchange matrix with an electrolyte concentration gradient of increasingly higher conductivity, up to about 40-100 mS, into a CEX eluant pool; and (f) loading the CEX eluant pool onto a hydrophobic interaction chromatography (HIC) matrix in a high conductivity buffer at pH 5.0-6.0 and washing the HIC matrix. The inventive method separates the POI from β-galactosyl-binding galectin host cell protein contaminant(s) and from other unwanted contaminants, such as metallic cation contaminants.

Glycosylated recombinant therapeutic proteins, such as, but not limited to aflibercept, alefacept, etanercept, abatacept, belatacept, rFVIIIFc, rFIXFc, and rilonacept, can be purified from such contaminants on an industrial scale using the inventive method.

The foregoing summary is not intended to define every aspect of the invention, and additional aspects are described in other sections, such as the Detailed Description of Embodiments. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus. Although the applicant(s) invented the full scope of the invention described herein, the applicants do not intend to claim subject matter described in the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

DETAILED DESCRIPTION OF EMBODIMENTS

Figure 1:
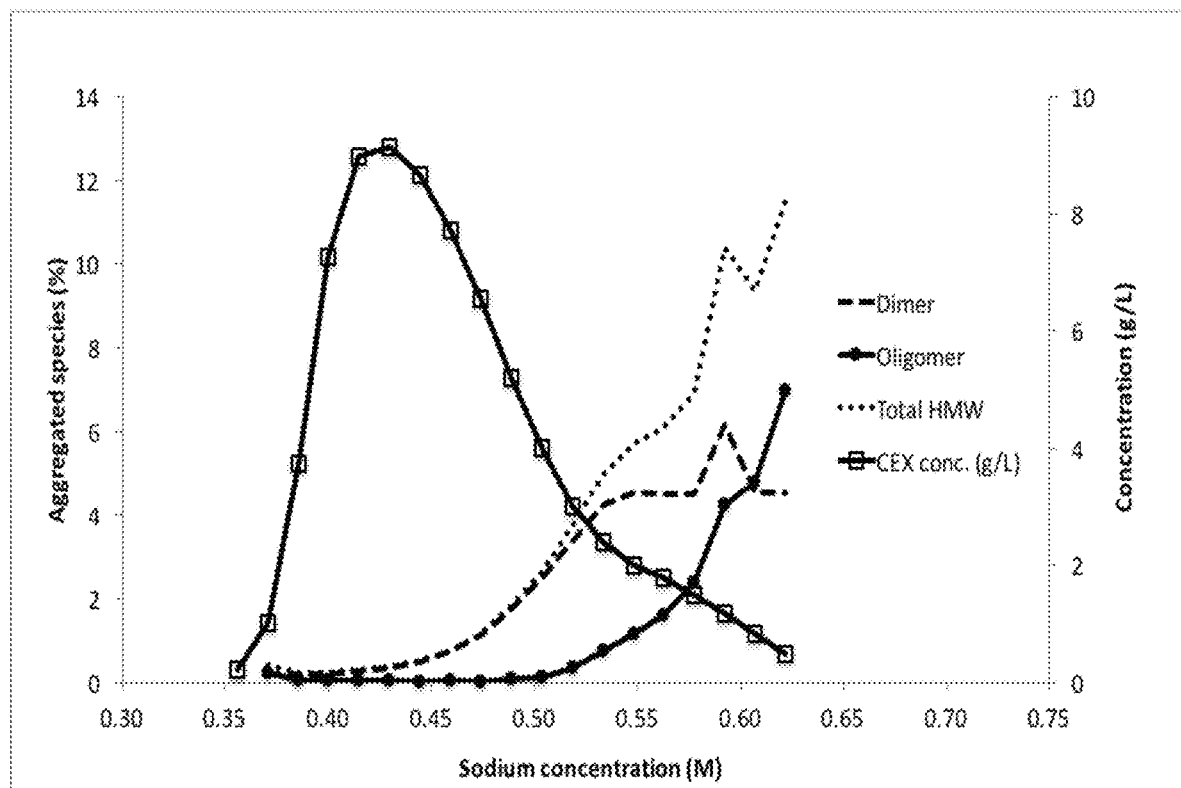
FIG. 1 shows a comparison of data from Fractogel® $SO_3^-$ CEX chromatography fractions analyzed for product concentration and HMW levels by size exclusion chromatography across the NaCl gradient elution.

The section headings used herein are for organizational purposes only and are not to be construed as limiting the subject matter described.

Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. Thus, as used in this specification and the appended claims, the singular forms "a", "an" and "the" include plural referents unless the context clearly indicates otherwise. For example, reference to "a protein" includes a plurality of proteins; reference to "a cell" includes populations of a plurality of cells.

The present invention relates to a method for purifying a glycosylated recombinant protein of interest from a contaminant. The glycosylated recombinant protein of interest comprises at least the $C_H2$ and $C_H3$ domains of an immunoglobulin Fc domain and one or more terminal beta-galactosyl residues. An example of such a glycosylated recombinant protein is aflibercept, which is also known commercially as Eylea®. Aflibercept is an assembly of two identical fusion polypeptide chains having the aflibercept amino acid sequence (SEQ ID NO:1), typically produced most conveniently by recombinant DNA expression technology. The aflibercept amino acid sequence is the following:

SEQ ID NO: 1
SDTGRPFVEMYSEIPEIIHMTEGRELVIP<u>C</u>RVTSPNITVTLKKFPLDTLI

PDGKRIIWDSRKGFIISNATYKEIGLLT<u>C</u>EATVNGHLYKTNYLTHRQTNT

IIDVVLSPSHGIELSVGEKLVLN<u>C</u>TARTELNVGIDFNWEYPSSKHQHKKL

VNRDLKTQSGSEMKKFLSTLTIDGVTRSDQGLYT<u>C</u>AASSGLMTKKNSTFV

RVHEKDKTHT<u>C</u>PP<u>C</u>PAPELLGGPSVFLFPPKPKDTLMISRTPEVT<u>C</u>VVVD

VSHEDPEVKFNWYVDGVEVHNAKTKPREEQYNSTYRVVSVLTVLHQDWLN

GKEYK<u>C</u>KVSNKALPAPIEKTISKAKGQPREPQVYTLPPSRDELTKNQVSL

T<u>C</u>LVKGFYPSDIAVEWESNGQPENNYKTTPPVLDSDGSFFLYSKLTVDKS

RWQQGNVFS<u>C</u>SVMHEALHNHYTQKSLSLSPG//.

Disulfide bridges are expected between the cysteine residues at following amino acid positions of SEQ ID NO:1 (underlined cysteine (C) residues shown in SEQ ID NO:1, above):

30-79 (intrachain)
124-185 (intrachain)
211-211 (interchain)
214-214 (interchain)
246-306 (intrachain)
352-410 (intrachain).

The two fusion polypeptide chains of aflibercept are covalently linked by disulfide linkage at amino acid positions 211 and 214 of SEQ ID NO:1. The fusion protein is typically glycosylated, with N-glycan (that can have terminal beta-galactosyl residues, dependent on culture conditions) covalently linked at asparagine residues at positions 36, 68, 123, 196, and 282 of SEQ ID NO:1 (bold/italicized asparagine (N) residues shown in SEQ ID NO:1 above).

"Aflibercept" within the scope of the invention also includes embodiments in which one, both, or none, of the fusion polypeptide chains has the amino acid sequence SEQ ID NO:1 with an additional carboxy-terminal lysine (K) residue.

Other glycosylated recombinant proteins of interest (or "POI") can include, but are not limited to, alefacept, etanercept, abatacept, belatacept, rFVIIIFc, rFIXFc, and rilonacept, and various therapeutic peptibodies.

The glycosylated recombinant protein of interest is initially contained in a batch or perfusion (continuous flow bioprocessing) host cell culture supernatant or filtrate (e.g., after one or more steps of diafiltration and/or ultrafiltration and/or viral filtration) for further processing by the inventive method. If desired, additional purification steps can also be applied to a preparation of the glycosylated recombinant protein of interest before or after applying the steps of the inventive method. For example, the POI can be purified by one or several steps, as appropriate, using, for example, diafiltration, ultrafiltration, hydroxylapatite chromatography, cation exchange (CEX) or anion exchange (AEX) chromatography, or affinity chromatography, using the antigen of interest or Protein A or protein G as an affinity ligand. Protein A can be used to purify proteins that include polypeptides are based on human γ1, γ2, or γ4 heavy chains (Lindmark et al., J. Immunol. Meth. 62: 1-13 (1983)). Protein G is recommended for all mouse isotypes and for human γ3 (Guss et al, EMBO J. 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the protein comprises a $C_H3$ domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible options, depending on the protein to be recovered.

The present method for purifying a glycosylated recombinant protein of interest from a contaminant involves loading a batch or perfusion host cell culture supernatant or filtrate comprising the glycosylated recombinant protein of interest (POI) onto a Protein A affinity chromatography matrix (i.e., Protein A matrix), at about neutral pH. "Protein A" is an approximately 42 kDa surface protein originally found in the cell wall of the bacteria *Staphylococcus aureus*; Protein A is encoded by the spa gene of *S. aureus*, and its expression in *S. aureus* is controlled by DNA topology, cellular osmolarity, and a two-component system called ArlS-ArlR. (See, Fournier, B., and Klier, A, *Protein A gene expression is regulated by DNA supercoiling which is modified by the ArlS-ArlR two-component system of Staphylococcus aureus*, Microbiology 150:3807-19 (2004)). Protein A (Spa gene product) is useful in biochemical research and industry because of its ability to bind immunoglobulins. Protein A is composed of five homologous Ig-binding domains that fold into a three-helix bundle. Each domain is able to bind proteins from many mammalian species, most notably IgGs. It has been shown via crystallographic refinement that the primary binding site for Protein A is on the Fc region, between the $C_H2$ and $C_H3$ domains. (Deisenhofer, J., *Crystallographic refinement and atomic models of a human Fc fragment and its complex with fragment B of Protein A from Staphylococcus aureus at 2.9- and 2.8-Å resolution*, Biochemistry 20 (9): 2361-70 (1981)). In addition, Protein A binds human IgG molecules containing IgG F(ab')2 fragments from the human VH3 gene family. (See, Sasso E H, Silverman G J, Mannik M, *Human IgA and IgG F(ab')₂ that bind to staphylococcal Protein A belong to the VHIII subgroup*, Journal of Immunology. 147 (6): 1877-83 (1991)). Protein A is typically produced and purified in industrial fermentation for use in immunology, biological research and industrial applications. Natural (or native) Protein A can be cultured in *Staphylococcus aureus* and contains the five homologous antibody binding regions described above and a C-terminal region for cell wall attachment. Recombinant versions of Protein A, typically produced in *Escherichia coli*, are also useful for purposes of the invention. For use in the present invention, Protein A matrix can be obtained commercially in various embodiments (e.g., Protein A-Sepharose® from *Staphylococcus aureus*, from Sigma Aldrich; MabSelect™ Protein A, MabSelect SuRe® Protein A, MabSelect SuRe® LX, and Protein A Sepharose® FF from GE Healthcare Life Sciences; Eshmuno® A Protein A from EMD Millipore; Toyopearl® AF-rProtein A from Tosoh Bioscience; POROS® Protein A from Thermo Fisher Scientific; CaptivA® Protein A affinity resin from Repligen). Recombinant versions of Protein A commonly contain the five homologous antibody binding domains, but for purposes of the present invention can vary in other parts of the structure in order to facilitate covalent coupling to substrates, e.g., resins (such as, but not limited to, agarose). A Protein A matrix may be placed or packed into a column useful for the purification of proteins. Also useful in the present invention in a Protein A matrix are engineered versions of Protein A that are multimers (typically tetramers, pentamers or hexamers) of a single domain which has been modified to improve its characteristics for industrial applications.

Encompassed within the term "matrix" are resins, beads, nanoparticles, nanofibers, hydrogels, membranes, and monoliths, or any other physical matrix, bearing a relevant chromatographic ligand (e.g., Protein A or other affinity chromatographic ligand, a charged moiety, or a hydrophobic moiety, etc.) for purposes of the inventive method.

The batch host cell culture or perfusion (continuous flow bioprocessing) host cell culture, supernatant or filtrate containing the glycosylated recombinant protein of interest also contains a galectin host cell contaminant reversibly bound to the one or more terminal beta-galactosyl residues of the glycosylated recombinant protein of interest (POI). The term "galectin" means a β-galactoside-binding lectin, usually occurring in a soluble form. Various galectins are expressed by a wide variety of animal cell types and distinguishable by the amino acid sequence of their carbohydrate-recognition domains (CRD). There are three subgroups: (i) prototypical galectins, which contain a single CRD that may associate to form homodimers; (ii) chimeric galectins, e.g., galectin-3, which is characterized by having a single CRD and a large amino-terminal domain, which is rich in proline, glycine, and tyrosine residues; and (iii) tandem-repeat galectins, in which at least two CRDs occur within a single polypeptide, covalently bridged or linked by a small peptide link domain, typically ranging from 5 to more than 50 amino acid residues in length. In addition, many of the galectin transcripts may be differentially spliced to generate different isoforms. Examples of galectins include electrolectin and a variety of S-type (sulfhydryl-dependent) galectins. Some examples include, but are not limited to, galectin-1, galectin-3, galectin-4, galectin-6, galectin-7, galectin-8, galectin-9, galectin-10, galectin-12, galectin-13, and galectin-14. (See, e.g., Cummings R D and Liu F T, Galectins, In: Varki A, Cummings R D, Esko J D, Freeze H H, Stanley P, Bertozzi C R, Hart G W, Etzler M E, editors. *Essentials of Glycobiology.* 2nd edition. Cold Spring Harbor (N.Y.): Cold Spring Harbor Laboratory Press; 2009. Chapter 33; Gitt, M A et al., *Galectin-4 and galectin-6 are two closely related lectins expressed in mouse gastrointestinal tract*, J Biol Chem. 273(5):2954-60 (1998); Bidon, N. et al., *Galectin-8: a complex sub family of galectins (Review)*, Int J Mol Med. 8(3):245-50 (2001); Hadari, Y R et al., *Galectin-8. A new rat lectin, related to galectin-4*, J Biol Chem. 270(7):3447-53 (1995); Sato, M. et al., *Functional analysis of the carbohydrate recognition domains and a linker peptide of galectin-9 as to eosinophil chemoattractant activity*, Glycobiology 12(3):191-97 (2002); Yang, R Y et al., *Cell cycle regulation by galectin-12, a new member of the galectin superfamily*, J Biol Chem. 276(23):20252-60 (2001); Ramaswamy, S et al., *Structural basis of multivalent galactose-based dendrimer recognition by human galectin-7*, FEBS J. 2015 January; 282(2):372-87 (2015); Patnaik, S K et al., *Complex N-glycans are the major ligands for galectin-1, -3, and-8 on Chinese hamster ovary cells*, Glycobiology 16(4):305-17 (2006)).

"Galectin-3" is a β-galactoside-binding protein of mammalian cells, such as, but not limited to, hamster or hamster-derived cells, mouse or mouse-derived cells, or human or human-derived cells. This host cell lectin is widely distributed among cells of mammalian species. (See, e.g., Mehul, B. et al., J. Biol. Chem. 269, 18250-18258 (1994); Mehul, B. et al., *Cross-linking of galectin 3, a galactose-binding protein of mammalian cells, by tissue-type transglutaminase*, FEBS Lett 360:160-164 (1995); Reljic, R. et al., *Mouse monoclonal IgA binds to the galectin-3/Mac-2 lectin from mouse macrophage cell lines*, Immunology Letters, 93:1, 51 (2004); Henrick, K. et al., *Evidence for subsites in the galectins involved in sugar binding at the nonreducing end of the central galactose of oligosaccharide ligands: sequence analysis, homology modeling and mutagenesis studies of hamster galectin-3*, Glycobiology 8(1):45-57 (1998); Dumic et al., *Galectin-3: An open-ended story*, Biochimica and Biophysica Acta 1760:616-635 (2006)).

The term "contaminant" or "impurity" refers to any foreign or objectionable molecule or ion, particularly a biological macromolecule such as a DNA, an RNA, or a protein, other than the recombinant protein of interest being purified that is present in a sample of the recombinant protein being purified. Contaminants include, for example, other proteins from host cells that secrete the recombinant protein being purified, e.g., contaminating galectin host cell protein (e.g., galectin-3), or metallic cations, e.g., aluminum cations (e.g., Al(III)), barium cations, calcium cations, cobalt cations (e.g., Co(II)), copper cations, iron cations (e.g., Fe(II) or Fe(III)), zinc cations, magnesium cations, manganese cations, mercury cations, nickel cations, and/or strontium cations. Contaminant components of a protein's natural environment or medium are materials that would interfere with diagnostic or therapeutic uses for the protein, and may include enzymes, hormones, and other proteinaceous or nonproteinaceous (e.g., polynucleotides, lipids, carbohydrates) solutes. Typically, an "isolated protein" constitutes at least about 5%, at least about 10%, at least about 25%, or at least about 50% of a given sample. In some embodiments, the protein of interest, e.g., aflibercept fusion protein, will be purified (1) to greater than 95% by weight of protein, and most preferably more than 99% by weight, or (2) to homogeneity by SDS-PAGE, or other suitable technique, under reducing or nonreducing conditions, optionally using a stain, e.g., Coomassie blue or silver stain. Isolated recombinant protein includes the in situ within recombinant cells. Typically, however, the isolated protein of interest (e.g., aflibercept) will be prepared by at least one purification step. Purity and impurity levels are assessed using any suitable assays including, but not limited to, CE-SDS, HCP ELISA, Galectin ELISA, multi-attribute mass spectrometry (MAM), metal analysis by mass spectrometry, and/or QPCR for DNA.

Various analytical techniques for measuring protein stability in the course of practicing the inventive method are available in the art and are reviewed, e.g., in Wang, W. (1999), *Instability, stabilization and formulation of liquid protein pharmaceuticals*, Int. J. Pharm. 185:129-188. Stability can be measured at a selected temperature for a selected time period. For example, where the formulation would in practice actually be stored at 2-8° C., generally the formulation should be stable at 30° C. for at least 1 month, or 40° C. for at least a week, and/or stable at 2-8° C. for at least two years. For rapid screening, a solution or formulation containing a protein may be kept at 30-40° C. for 2 weeks to 1 month, at which time protein stability is measured. This storage at higher than normal storage temperature (30-40° C.) is to simulate what would occur in a more conventional refrigerated temperature storage for a longer period, and is termed "accelerated stability."

A "stable" solution or formulation of a protein is one in which the protein therein essentially retains its physical stability and/or chemical stability and/or biological activity upon purification and/or processing (e.g., ultrafiltration, diafiltration, or other filtering steps, chromatographic steps, low pH viral inactivation, vial filling, transportation, and/or storage) of the protein, e.g., recombinant aflibercept protein. Together, the physical, chemical and biological stability of the protein of interest in a particular solution or formulation under particular physical conditions, e.g., temperature and pH, embody the "stability" of the protein. For instance, a protein stored at subzero temperatures would be expected to have no significant change in either chemical, physical or biological activity while a protein stored at 40° C. would be expected to have changes in its physical, chemical and biological activity with the degree of change dependent on the time of storage for the protein. The configuration of the protein formulation can also influence the rate of change. For instance, aggregate formation is highly influenced by protein concentration with higher rates of aggregation observed with higher protein concentration. Excipients are also known to affect stability of the drug product with, for example, addition of salt increasing the rate of aggregation for some proteins while other excipients such as sucrose are known to decrease the rate of aggregation during storage. Instability is also greatly influenced by pH giving rise to both higher and lower rates of degradation depending on the type of modification and pH dependence.

A protein "retains its physical stability," if it shows minimal signs of changes to the secondary and/or tertiary structure (i.e., intrinsic structure), or aggregation, and/or precipitation and/or denaturation upon visual examination of color and/or clarity, or as measured by UV light scattering or by size exclusion chromatography, or other suitable methods. Physical instability of a protein, i.e., loss of physical stability, can be caused by oligomerization resulting in dimer and higher order aggregates, subvisible, and visible particle formation, and precipitation. The degree of physical degradation can be ascertained using varying techniques depending on the type of degradant of interest. Dimers and higher order soluble aggregates can be quantified using size exclusion chromatography, while subvisible particles may be quantified using light scattering, light obscuration or other suitable techniques. In one embodiment, the stability of the protein is determined according to the percentage of aflibercept monomer protein in the solution, with a low percentage of degraded (e.g., fragmented) and/or aggregated protein.

A protein "retains its chemical stability" in a pharmaceutical formulation, if the chemical stability at a given time is such that covalent bonds are not made or broken, resulting in changes to the primary structure of the protein component. Changes to the primary structure may result in modifications of the secondary and/or tertiary and/or quaternary structure of the protein and may result in formation of aggregates or reversal of aggregates already formed. Typical chemical modifications can include isomerization, deamidation, N-terminal cyclization, backbone hydrolysis, methionine oxidation, tryptophan oxidation, histidine oxidation, beta-elimination, disulfide formation, disulfide scrambling, disulfide cleavage, and other changes resulting in changes to the primary structure including D-amino acid formation. Chemical instability, i.e., loss of chemical stability, may be interrogated by a variety of techniques including ion-exchange chromatography, capillary isoelectric focusing, analysis of peptide digests and multiple types of mass spectrometric techniques. Chemical stability can be assessed by detecting and quantifying chemically altered forms of the protein. Chemical alteration may involve size modification (e.g. clipping) which can be evaluated using size exclusion chromatography (SEC), SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by charge-based methods, such as, but not limited to, ion-exchange chromatography, capillary isoelectric focusing, or peptide mapping.

Loss of physical and/or chemical stability may result in changes to biological activity as either an increase or decrease of a biological activity of interest, depending on the modification and the protein being modified. A protein "retains its biological activity" in a pharmaceutical formulation, if the biological activity of the Protein At a given time is within about 30% of the biological activity exhibited at the time the pharmaceutical formulation was prepared. Activity is considered decreased if the activity is less than 70% of its starting value. Biological assays may include both in vivo and in vitro based assays such as ligand binding, potency, cell proliferation or other surrogate measure of its biopharmaceutical activity. As an example, biological activity of aflibercept can be estimated using an in vitro ligand binding assay such as binding to placental growth factor (PlGF) by ELISA or inhibition of VEGFA-dependent human umbilical vein endothelial cell (HUVEC) proliferation.

A recombinant protein of interest (e.g., aflibercept, alefacept, etanercept, abatacept, belatacept, rFVIIIFc, rFIXFc, and rilonacept) for purposes of the invention is typically produced by recombinant expression technology. The term "recombinant" indicates that the material (e.g., a nucleic acid or a polypeptide) has been artificially or synthetically (i.e., non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other well known molecular biological procedures. Examples of such molecular biological procedures are found in Maniatis et al., Molecular Cloning. A Laboratory Manual. Cold Spring Harbor Laboratory, Cold Spring Harbor, N.Y. (1982). A "recombinant DNA molecule," is comprised of segments of DNA joined together by means of such molecular biological techniques. The term "recombinant protein" or "recombinant polypeptide" as used herein refers to a protein molecule which is expressed using a recombinant DNA molecule. A "recombinant host cell" is a cell that contains and/or expresses a recombinant nucleic acid. For example, recombinant DNA molecules useful in expressing aflibercept fusion protein are described, e.g., by Papadopoulos et al., Modified Chimeric Polypeptides with Improved Pharmacokinetic Properties, U.S. Pat. No. 7,070,959 B2; and WO 00/75319 A1).

The term "naturally occurring," where it occurs in the specification in connection with biological materials such as polypeptides, nucleic acids, host cells, and the like, refers to materials which are found in nature.

The term "control sequence" or "control signal" refers to a polynucleotide sequence that can, in a particular host cell, affect the expression and processing of coding sequences to which it is ligated. The nature of such control sequences may depend upon the host organism. In particular embodiments, control sequences for prokaryotes may include a promoter, a ribosomal binding site, and a transcription termination sequence. Control sequences for eukaryotes may include promoters comprising one or a plurality of recognition sites for transcription factors, transcription enhancer sequences or elements, polyadenylation sites, and transcription termination sequences. Control sequences can include leader sequences and/or fusion partner sequences. Promoters and enhancers consist of short arrays of DNA that interact specifically with cellular proteins involved in transcription (Maniatis, et al., Science 236:1237 (1987)). Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see Voss, et al., Trends Biochem. Sci., 11:287 (1986) and Maniatis, et al., Science 236:1237 (1987)).

A "promoter" is a region of DNA including a site at which RNA polymerase binds to initiate transcription of messenger RNA by one or more downstream structural genes. Promoters are located near the transcription start sites of genes, on the same strand and upstream on the DNA (towards the 5' region of the sense strand). Promoters are typically about 100-1000 bp in length.

An "enhancer" is a short (50-1500 bp) region of DNA that can be bound with one or more activator proteins (transcription factors) to activate transcription of a gene.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. For example, a control sequence in a vector that is "operably linked" to a protein coding sequence is ligated thereto so that expression of the protein coding sequence is achieved under conditions compatible with the transcriptional activity of the control sequences.

"Polypeptide" and "protein" are used interchangeably herein and include a molecular chain of two or more amino acids linked covalently through peptide bonds. The terms do not refer to a specific length of the product. Thus, "peptides," and "oligopeptides," are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs or non-canonical or unnatural amino acids are included as can be expressed recombinantly using known protein engineering techniques. In addition, fusion proteins can be derivatized as described herein by well-known organic chemistry techniques.

A "variant" of a polypeptide (e.g., a fusion protein, an immunoglobulin, or an antibody) comprises an amino acid sequence wherein one or more amino acid residues are inserted into, deleted from and/or substituted into the amino acid sequence relative to another polypeptide sequence. Variants include fusion proteins.

The term "fusion protein," for example, aflibercept fusion protein, indicates that the protein includes polypeptide components derived from more than one parental protein or polypeptide. Typically, a fusion protein is expressed from a "fusion gene" in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein.

A "secreted" protein refers to those proteins capable of being directed to the endoplasmic reticulum (ER), secretory vesicles, or the extracellular space as a result of a secretory signal peptide sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage. In some other embodiments, the aflibercept fusion protein of interest can be synthesized by the host cell as a secreted protein, which can then be further purified from the extracellular space and/or medium.

As used herein "soluble" when in reference to a protein produced by recombinant DNA technology in a host cell is a protein that exists in aqueous solution; if the protein contains a twin-arginine signal amino acid sequence the soluble protein is exported to the periplasmic space in gram negative bacterial hosts, or is secreted into the culture medium by eukaryotic host cells capable of secretion, or by bacterial host possessing the appropriate genes (e.g., the kil gene). Thus, a soluble protein is a protein which is not found in an inclusion body inside the host cell. Alternatively, depending on the context, a soluble protein is a protein which is not found integrated in cellular membranes, or, in vitro, is dissolved, or is capable of being dissolved in an aqueous buffer under physiological conditions without forming significant amounts of insoluble aggregates (i.e., forms aggregates less than 10%, and typically less than about 5%, of total protein) when it is suspended without other proteins in an aqueous buffer of interest under physiological conditions, such buffer not containing a detergent or chaotropic agent, such as urea, guanidinium hydrochloride, or lithium perchlorate. In contrast, an insoluble protein is one which exists in denatured form inside cytoplasmic granules (called an inclusion body) in the host cell, or again depending on the context, an insoluble protein is one which is present in cell membranes, including but not limited to, cytoplasmic membranes, mitochondrial membranes, chloroplast membranes, endoplasmic reticulum membranes, etc., or in an in vitro aqueous buffer under physiological conditions forms significant amounts of insoluble aggregates (i.e., forms aggregates equal to or more than about 10% of total protein) when it is suspended without other proteins (at physiologically compatible temperature) in an aqueous buffer of interest under physiological conditions, such buffer not containing a detergent or chaotropic agent, such as urea, guanidinium hydrochloride, or lithium perchlorate.

The term "polynucleotide" or "nucleic acid" includes both single-stranded and double-stranded nucleotide polymers containing two or more nucleotide residues. The nucleotide residues comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phosphoraniladate and phosphoroamidate.

The term "oligonucleotide" means a polynucleotide comprising 200 or fewer nucleotide residues. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a label, including a radiolabel, a fluorescent label, a hapten or an antigenic label, for detection assays. Oligonucleotides may be used, for example, as PCR primers, cloning primers or hybridization probes.

A "polynucleotide sequence" or "nucleotide sequence" or "nucleic acid sequence," as used interchangeably herein, is the primary sequence of nucleotide residues in a polynucleotide, including of an oligonucleotide, a DNA, and RNA, a nucleic acid, or a character string representing the primary sequence of nucleotide residues, depending on context. From any specified polynucleotide sequence, either the given nucleic acid or the complementary polynucleotide sequence can be determined. Included are DNA or RNA of genomic or synthetic origin which may be single- or double-stranded, and represent the sense or antisense strand. Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

As used herein, an "isolated nucleic acid molecule" or "isolated nucleic acid sequence" is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined. An isolated nucleic acid molecule is other than in the form or setting in which it is found in nature. However, an isolated nucleic acid molecule includes a nucleic acid molecule contained in cells that ordinarily express the immunoglobulin (e.g., antibody) where, for example, the nucleic acid molecule is in a chromosomal location different from that of natural cells.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of ribonucleotides along the mRNA chain, and also determines the order of amino acids along the polypeptide (protein) chain. The DNA sequence thus codes for the RNA sequence and for the amino acid sequence.

The term "gene" is used broadly to refer to any nucleic acid associated with a biological function. Genes typically include coding sequences and/or the regulatory sequences required for expression of such coding sequences. The term "gene" applies to a specific genomic or recombinant sequence, as well as to a cDNA or mRNA encoded by that sequence. Genes also include non-expressed nucleic acid segments that, for example, form recognition sequences for other proteins. Non-expressed regulatory sequences including transcriptional control elements to which regulatory proteins, such as transcription factors, bind, resulting in transcription of adjacent or nearby sequences.

"Expression of a gene" or "expression of a nucleic acid" means transcription of DNA into RNA (optionally including modification of the RNA, e.g., splicing), translation of RNA into a polypeptide (possibly including subsequent post-translational modification of the polypeptide), or both transcription and translation, as indicated by the context.

An expression cassette is a typical feature of recombinant expression technology. The expression cassette includes a gene encoding a protein of interest, e.g., a gene encoding an aflibercept fusion protein sequence. A eukaryotic "expression cassette" refers to the part of an expression vector that enables production of protein in a eukaryotic cell, such as a mammalian cell. It includes a promoter, operable in a eukaryotic cell, for mRNA transcription, one or more gene(s) encoding protein(s) of interest and a mRNA termination and processing signal. An expression cassette can usefully include among the coding sequences, a gene useful as a selective marker. In the expression cassette promoter is operably linked 5' to an open reading frame encoding an exogenous protein of interest; and a polyadenylation site is operably linked 3' to the open reading frame. Other suitable control sequences can also be included as long as the expression cassette remains operable. The open reading frame can optionally include a coding sequence for more than one protein of interest.

As used herein the term "coding region" or "coding sequence" when used in reference to a structural gene refers to the nucleotide sequences which encode the amino acids found in the nascent polypeptide as a result of translation of an mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

Recombinant expression technology typically involves the use of a recombinant expression vector comprising an expression cassette.

The term "vector" means any molecule or entity (e.g., nucleic acid, plasmid, bacteriophage or virus) used to transfer protein coding information into a host cell.

The term "expression vector" or "expression construct" as used herein refers to a recombinant DNA molecule containing a desired coding sequence and appropriate nucleic acid control sequences necessary for the expression of the operably linked coding sequence in a particular host cell. An expression vector can include, but is not limited to, sequences that affect or control transcription, translation, and, if introns are present, affect RNA splicing of a coding region operably linked thereto. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired. Such techniques are well known in the art. (E.g., Goodey, Andrew R.; et al., Peptide and DNA sequences, U.S. Pat. No. 5,302,697; Weiner et al., Compositions and methods for protein secretion, U.S. Pat. Nos. 6,022,952 and 6,335,178; Uemura et al., Protein expression vector and utilization thereof, U.S. Pat. No. 7,029,909; Ruben et al., 27 human secreted proteins, US 2003/0104400 A1). For expression of multi-subunit proteins of interest, separate expression vectors in suitable numbers and proportions, each containing a coding sequence for each of the different subunit monomers, can be used to transform a host cell. In other embodiments, a single expression vector can be used to express the different subunits of the protein of interest.

Recombinant expression technology typically involves a mammalian host cell comprising the recombinant expression vector.

The term "host cell" means a cell that has been transformed, or is capable of being transformed, with a nucleic acid and thereby expresses a gene or coding sequence of interest. The term includes the progeny of the parent cell, whether or not the progeny is identical in morphology or in genetic make-up to the original parent cell, so long as the gene of interest is present. Any of a large number of available and well-known host cells may be used in the practice of this invention to produce recombinant aflibercept fusion protein. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, bio-safety and costs. A balance of these factors must be struck with the understanding that not all hosts may be equally effective for the expression of a particular DNA sequence. Within these general guidelines, useful microbial host cells in culture include bacteria (such as *Escherichia coli* sp.), yeast (such as *Saccharomyces* sp.) and other fungal cells, algal or algal-like cells, insect cells, plant cells, mammalian (including human) cells, e.g., CHO cells and HEK-293 cells. Modifications can be made at the DNA level, as well. The peptide-encoding DNA sequence may be changed to codons more compatible with the chosen host cell. For *E. coli*, optimized codons are known in the art. Codons can be substituted to eliminate restriction sites or to include silent restriction sites, which may aid in processing of the DNA in the selected host cell. Next, the transformed host is cultured and purified. Host cells may be cultured under conventional fermentation conditions, e.g., in batch mode or continuous perfusion mode, so that the desired compounds are expressed. Such fermentation conditions are well known in the art.

Examples of useful mammalian host cell lines are Chinese hamster ovary cells, including CHO-K1 cells (e.g., ATCC CCL61), DXB-11, DG-44, and Chinese hamster ovary cells/-DHFR (CHO, Urlaub et al, Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture (Graham et al, J. Gen Virol. 36: 59 (1977)); baby hamster kidney cells (BHK, ATCC CCL 10); mouse Sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N.Y Acad. Sci. 383: 44-68 (1982)); MRC 5 cells or FS4 cells; or mammalian myeloma cells.

"Cell," "cell line," and "cell culture" are often used interchangeably and all such designations herein include cellular progeny. For example, a cell "derived" from a CHO cell is a cellular progeny of a Chinese Hamster Ovary cell, which may be removed from the original primary cell parent by any number of generations, and which can also include a transformant progeny cell. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

Host cells are transformed or transfected with the above-described nucleic acids or vectors for production of polypeptides (including target binding proteins) and are cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of polypeptides, such as antibodies.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al., 1981, Gene 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

The host cells used to produce the glycosylated recombinant protein of interest or POI (e.g., recombinant aflibercept fusion polypeptides) in the invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. Nos. 4,767,704; 4,657, 866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source, such that the physiological conditions of the cell in, or on, the medium promote expression of the protein of interest by the host cell; any other necessary supplements may also be included at appropriate concentrations that would be known to those skilled in the art. The culture conditions, such as temperature (typically, but not necessarily, about 37° C.), pH (typically, but not necessarily, about pH 6.5-7.5), oxygenation, and the like, are those previously used with the host cell selected for expression of the protein of interest, and will be apparent to the ordinarily skilled artisan. The culture medium can include a suitable amount of serum such a fetal bovine serum (FBS), or preferably, the host cells can be adapted for culture in serum-free medium. In some embodiments, the aqueous medium is liquid, such that the host cells are cultured in a cell suspension within the liquid medium. The host cells can be usefully grown in batch cell culture or in continuous (perfusion) cell culture systems.

In other embodiments, the mammalian host cells can be cultured on solid or semi-solid aqueous medium, for example, containing agar or agarose, to form a medium or substrate surface to which the cells adhere and form an adhesion layer.

Upon culturing the host cells, the recombinant polypeptide can be produced intracellularly, in the periplasmic space, or directly secreted into the medium. If the polypeptide, such as aflibercept, is produced intracellularly, as a first step, the particulate debris, either host cells or lysed fragments, is removed, for example, by centrifugation, depth filtration or ultrafiltration.

"Under physiological conditions" with respect to incubating buffers or other binding/reaction assay reagents means incubation under conditions of temperature, pH, and ionic strength, that permit a biochemical reaction, such as a non-covalent binding reaction, to occur. Typically, the temperature is at room or ambient temperature up to about 37° C. and at pH 6.5-7.5.

"Physiologically acceptable salt" of a composition of matter, for example a salt of a protein of interest, e.g., a fusion protein or an immunoglobulin, such as an antibody, or any other protein of interest, means any salt, or salts, that are known or later discovered to be pharmaceutically acceptable. Some non-limiting examples of pharmaceutically acceptable salts are: acetate; trifluoroacetate; hydrohalides, such as hydrochloride and hydrobromide; sulfate; citrate;

maleate; tartrate; glycolate; gluconate; succinate; mesylate; besylate; salts of gallic acid esters (gallic acid is also known as 3, 4, 5 trihydroxybenzoic acid) such as PentaGalloylGlucose (PGG) and epigallocatechin gallate (EGCG), salts of cholesteryl sulfate, pamoate, tannate and oxalate salts.

A "reaction mixture" is an aqueous mixture containing all the reagents and factors necessary, which under physiological conditions of incubation, permit an in vitro biochemical reaction of interest to occur, such as a covalent or non-covalent binding reaction.

A "domain" or "region" (used interchangeably herein) of a polynucleotide is any portion of the entire polynucleotide, up to and including the complete polynucleotide, but typically comprising less than the complete polynucleotide. A domain can, but need not, fold independently (e.g., DNA hairpin folding) of the rest of the polynucleotide chain and/or be correlated with a particular biological, biochemical, or structural function or location, such as a coding region or a regulatory region.

A "domain" or "region" (used interchangeably herein) of a protein is any portion of the entire protein, up to and including the complete protein, but typically comprising less than the complete protein. A domain can, but need not, fold independently of the rest of the protein chain and/or be correlated with a particular biological, biochemical, or structural function or location (e.g., a ligand binding domain, or a cytosolic, transmembrane or extracellular domain).

Quantification of the recombinant protein of interest, such as, but not limited to, aflibercept fusion protein, is often useful or necessary in tracking protein production or protein purification step yield (or for lot release assays of drug substance or drug product containing aflibercept or other therapeutic protein of interest). An antibody that specifically binds the protein of interest, particularly a monoclonal antibody, can therefore be useful for these purposes.

The term "antibody", or interchangeably "Ab", is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab, Fab', F(ab')2, Fv, single chain antibodies, diabodies), comprising complementarity determining regions (CDRs) of the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated. Different isotypes can have different effector functions; for example, IgG1 and IgG3 isotypes can have antibody-dependent cellular cytotoxicity (ADCC) activity.

An "isolated" protein, e.g., an aflibercept fusion protein or other recombinant protein of interest, is one that has been identified and separated from one or more components of its natural environment or of a culture medium in which it has been secreted by a producing cell. In some embodiments, the isolated protein is substantially free from proteins or polypeptides or other contaminants that are found in its natural or culture medium environment that would interfere with its therapeutic, diagnostic, prophylactic, research or other use.

The term "to bind" or "binding" a molecule to Protein A, or a Protein A matrix, means exposing the molecule to Protein A, under appropriate conditions (e.g., pH and selected salt/buffer composition), such that the molecule is reversibly immobilized in, or on, the Protein A matrix (e.g., Protein A resin) by virtue of its binding affinity to Protein A under those conditions, regardless of the physical mechanism of affinity that may be involved. (See, e.g., Jendeberg, L. et al., *The Mechanism of Binding Staphylococcal Protein A to Immunoglobin G Does Not Involve Helix Unwinding*, Biochemistry 35(1): 22-31 (1996); Nelson, J. T. et al., *Mechanism of Immobilized Protein A Binding to Immunoglobulin G on Nanosensor Array Surfaces*, Anal. Chem., 87(16):8186-8193 (2015)).

The term "to bind" or "binding" a molecule to an ion exchange matrix (e.g., a CEX matrix, such as a CEX resin), means exposing the molecule to the ion exchange matrix under appropriate conditions (e.g., pH and selected salt/buffer composition) such that the molecule is reversibly immobilized in, or on, the ion exchange matrix by virtue of ionic interactions between the molecule and a charged group or charged groups (i.e., charged ligands) of the ion exchange matrix.

The term "buffer" or "buffered solution" refers to solutions which resist changes in pH by the action of its conjugate acid-base range. Examples of useful buffers that control pH at ranges of about pH 4 to about pH 6.5 include acetate, MES, citrate, Tris, bis-tris, histidine, arginine, succinate, citrate, glutamate, and lactate, or a combination of two or more of these, or other mineral acid or organic acid buffers; phosphate is another example of a useful buffer. Salts containing sodium, ammonium, and potassium cations are often used in making a buffered solution.

The term "loading buffer" or "equilibrium buffer" refers to the buffer, and salt or salts, which is mixed with a protein preparation (e.g., a batch or perfusion culture supernatant or filtrate, or an eluant pool containing the protein of interest) for loading the protein preparation onto a Protein A matrix or onto an ion exchange matrix (e.g., a CEX matrix or AEX matrix), or onto a hydrophobic interaction chromatography (HIC) matrix, as the case may be. This buffer is also used to equilibrate the matrix before loading, and to wash after loading the protein.

The term "wash buffer" is used herein to refer to the buffer that is passed over a Protein A matrix or ion exchange matrix (e.g., a CEX matrix or AEX matrix), or a hydrophobic interaction chromatography (HIC) matrix, as the case may be, following loading of a protein preparation and prior to elution or after flow-through of the protein of interest. The wash buffer may serve to remove one or more contaminants without substantial elution of the desired protein or can be used to wash out a non-binding protein.

The term "elution buffer" or "eluant" refers to the buffer used to elute the protein of interest (POI) reversibly bound to a matrix. As used herein, the term "solution" refers to either a buffered or a non-buffered solution, including water.

The term "elution pool" or "eluant pool" means the material eluted from a matrix, which material includes the recombinant protein of interest.

The term "loading," with respect to a Protein A matrix, or an ion exchange matrix (e.g., a CEX matrix), or a hydrophobic interaction chromatography (HIC) matrix, means loading a protein preparation (e.g., a batch or perfusion culture supernatant or filtrate, or an eluant pool containing the protein of interest) onto the Protein A matrix or the ion exchange matrix, or the HIC matrix.

The term "washing," with respect to a Protein A matrix or an ion exchange matrix (e.g., a CEX matrix) or a hydrophobic interaction chromatography (HIC) matrix, means passing an appropriate buffer through or over the Protein A matrix or ion exchange matrix or HIC matrix, as the case may be.

The inventive method for purifying a glycosylated recombinant protein of interest from a contaminant involves washing the Protein A matrix that has the POI reversibly bound to it, with a buffer at about pH 6.0-6.5, comprising 1-3 M calcium chloride. More preferably the concentration of calcium chloride in the wash buffer is 2-2.7 M calcium chloride, for example, about 2.0 M, about 2.1 M, about 2.2 M, about 2.3 M, about 2.4 M, about 2.5 M, about 2.6 M, or about 2.7 M calcium chloride.

The term "eluting" a molecule (e.g. a desired recombinant protein or contaminant) from a Protein A matrix or an ion exchange matrix (e.g., a CEX matrix), means removing the molecule from such material, typically by passing an elution buffer over the Protein A matrix or the ion exchange matrix.

The term "separate" or "isolate" as used in connection with protein purification refers to the separation of a desired protein from a second protein or other contaminant or impurity in a mixture comprising both the desired protein and a second protein or other contaminant or impurity, such that at least the majority of the molecules of the desired protein are removed from that portion of the mixture that comprises at least the majority of the molecules of the second protein or other contaminant or impurity.

The term "purify" or "purifying" a desired protein from a composition or solution comprising the recombinant protein of interest (i.e., the "POI") and one or more contaminants means increasing the degree of purity of the desired recombinant protein in the composition or solution by removing (completely or partially) at least one contaminant from the composition or solution.

The term "therapeutic biologic product" means a protein applicable to the prevention, treatment, or cure of a disease or condition of human beings. Examples of therapeutic biologic products include monoclonal antibodies, recombinant forms of a native protein (e.g., a receptor, ligand, hormone, enzyme or cytokine), fusion proteins, peptibodies, and/or a monomer domain binding proteins, e.g., based on a domain selected from LDL receptor A-domain, thrombospondin domain, thyroglobulin domain, trefoil/PD domain, VEGF binding domain, EGF domain, Anato domain, Notch/LNR domain, DSL domain, integrin beta domain, and Ca-EGF domain.

The term "peptibody" refers to a fusion protein molecule comprising an antibody Fc domain (i.e., at least the $C_H2$ and $C_H3$ antibody domains) that excludes antibody $C_H1$, CL, VH, and VL domains as well as Fab and F(ab)$_2$, wherein the Fc domain is attached to one or more peptides, preferably a pharmacologically active peptide. The production of peptibodies is generally described in PCT publication WO00/24782.

The term "cation exchange matrix" or "CEX matrix," refers to a solid phase that is negatively charged and has free cations for exchange with cations in an aqueous solution passed over or through the solid phase. The negative charge may be provided by attaching one or more charged ligands to the solid phase, e.g. by covalent linking. Alternatively, or in addition, the charge may be an inherent property of the solid phase (e.g. as is the case for silica, which has an overall negative charge). Cation exchange ("CEX") matrix (e.g., CEX resin) may be placed or packed into a column useful for the purification of proteins. CEX is an effective step for removing protein high molecular weight (HMW) species, as well as host cell protein, DNA, and residual Protein A (Zeid, et al., (2008). Biotechnology and Bioengineering 102, 971-976; Yigzaw, Y., et al., (2009), Current Pharmaceutical Biotechnology 10, 421-426; Gagnon, P., Purification tools for monoclonal antibodies. 1996: Validated Biosystems, Inc.; Stein, A., and Kiesewetter, A. (2007). Journal of Chromatography B 848, 151-158; Staby, A., et al., (2006), Journal of Chromatography 1118, 168-179). Generally, CEX is operated in bind-and-elute mode (BEM) where the protein is bound to the CEX matrix (e.g., CEX resin) under low conductivity conditions at a pH that is below the pI of the target molecule. Elution of the bound protein is then typically achieved by increasing the conductivity and/or inducing a pH shift. This can be performed either over a linear gradient or a step elution to predetermined conditions. Impurities, particularly HMW species, often bind more tightly than the mAb product and can be separated from the main desired fraction by adjusting the elution conditions and pool collection criteria (Yigzaw, Y., et al., (2009) supra; Gagnon, P., et al., (1996) supra; Pabst, T. M., et al., (2009) Journal of Chromatography 1216, 7950-7956). Examples of useful CEX matrices available commercially include, but are not limited to, Fractogel® COO⁻, Fractogel® $SO_3^-$, or Eshmuno® S from EMD Millipore; SP Sepharose® FF or Capto™ S from GE Healthcare Life Sciences; and POROS® XS from Thermo Fisher Scientific; Toyopearl® Sulfate-650-F from Tosoh Bioscience.

The term "anion exchange matrix" or "AEX matrix" refers to a solid phase that is positively charged and has free anions for exchange with anions in an aqueous solution passed over or through the solid phase. The charge may be provided by attaching one or more positively charged ligands to the solid phase, e.g. by covalent linking. Alternatively, or in addition, the charge may be an inherent property of the solid phase. Anion exchange ("AEX") matrix (e.g., an AEX resin) may be placed or packed into a column useful for the purification of proteins.

The term "hydrophobic interaction chromatography matrix" or "HIC matrix" refers to a solid phase material or matrix that interacts differentially with substances, based on the surface hydrophobicity of the substance. (See, e.g., Queiroz, J. A. et al., *Hydrophobic interaction chromatography of proteins*, J. Biotechnol. 87(2):143-59 (2001); Chen, J. et al., *Comparison of standard and new generation hydrophobic interaction chromatography resins in the monoclonal antibody purification process*, Journal of Chromatography A 1177(2): 272-81 (2008)). Various suitable HIC matrices are commercially available, for example, Macro-Prep® HIC resins, such as Macro-Prep® t-Butyl from Bio-Rad; Toyopearl® Butyl, Toyopearl® Butyl 650M, Toyopearl® Hexyl, Toyopearl® Hexyl 650C or Toyopearl® Phenyl from Tosoh Bioscience; Fractogel® EMD phenyl 650 from EMD Millipore; and Phenyl Sepharose® Fast Flow High Sub or Phenyl Sepharose® Fast Flow Low Sub from GE Healthcare Life Sciences. A multi-modal resin that includes an HIC moiety can also be a useful HIC matrix for practicing the inventive method. The HIC matrix (e.g., a HIC resin) may be placed or packed into a column useful for the purification of proteins.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies that are target binding proteins are highly specific binders, being directed against an individual antigenic site or epitope, in contrast to polyclonal antibody preparations that typically include different antibodies directed against different epitopes. Nonlimiting examples of monoclonal antibodies include murine, rabbit, rat, chicken, chimeric, humanized, or human antibodies, fully assembled antibodies, multispecific antibodies (including bispecific antibodies), antibody fragments that can bind an antigen (including, Fab, Fab', F(ab)$_2$, Fv, single chain antibodies, diabodies), maxibodies, nanobodies, and recombinant peptides comprising CDRs of the foregoing as long as they exhibit the desired biological activity, or variants or derivatives thereof.

The modifier "monoclonal" indicates the character of the antibody as being obtained from a substantially homogeneous population of antibodies, and is not to be construed as requiring production of the antibody by any particular method. For example, monoclonal antibodies may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The term "immunoglobulin" encompasses full antibodies comprising two dimerized heavy chains (HC), each covalently linked to a light chain (LC); a single undimerized immunoglobulin heavy chain and covalently linked light chain (HC+LC), or a chimeric immunoglobulin (light chain+heavy chain)-Fc heterotrimer (a so-called "hemibody"). An "immunoglobulin" is a protein, but is not necessarily a target binding protein.

In an "antibody", each tetramer is composed of two identical pairs of polypeptide chains, each pair having one "light" chain of about 220 amino acids (about 25 kDa) and one "heavy" chain of about 440 amino acids (about 50-70 kDa). The amino-terminal portion of each chain includes a "variable" ("V") region of about 100 to 110 or more amino acids primarily responsible for antigen recognition. The carboxy-terminal portion of each chain defines a constant region primarily responsible for effector function. The variable region differs among different antibodies. The constant region is the same among different antibodies. Within the variable region of each heavy or light chain, there are three hypervariable subregions that help determine the antibody's specificity for antigen in the case of an antibody that is a target binding protein. The variable domain residues between the hypervariable regions are called the framework residues and generally are somewhat homologous among different antibodies. Immunoglobulins can be assigned to different classes depending on the amino acid sequence of the constant domain of their heavy chains. Human light chains are classified as kappa (κ) and lambda (λ) light chains. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)). An "antibody" also encompasses a recombinantly made antibody, and antibodies that are glycosylated or lacking glycosylation.

The term "light chain" or "immunoglobulin light chain" includes a full-length light chain and fragments thereof having sufficient variable region sequence to confer binding specificity. A full-length light chain includes a variable region domain, $V_L$, and a constant region domain, $C_L$. The variable region domain of the light chain is at the amino-terminus of the polypeptide. Light chains include kappa chains and lambda chains.

The term "heavy chain" or "immunoglobulin heavy chain" includes a full-length heavy chain and fragments thereof having sufficient variable region sequence to confer binding specificity. A full-length heavy chain includes a variable region domain, $V_H$, and three constant region domains, $C_H1$, $C_H2$, and $C_H3$. The VH domain is at the amino-terminus of the polypeptide, and the CH domains are at the carboxyl-terminus, with the $C_H3$ being closest to the carboxy-terminus of the polypeptide. Heavy chains are classified as mu (μ), delta (δ), gamma (γ), alpha (α), and epsilon (ε), and define the antibody's isotype as IgM, IgD, IgG, IgA, and IgE, respectively. Heavy chains may be of any isotype, including IgG (including IgG1, IgG2, IgG3 and IgG4 subtypes), IgA (including IgA1 and IgA2 subtypes), IgM and IgE. Several of these may be further divided into subclasses or isotypes, e.g. IgG1, IgG2, IgG3, IgG4, IgA1 and IgA2. Different IgG isotypes may have different effector functions (mediated by the Fc region), such as antibody-dependent cellular cytotoxicity (ADCC) and complement-dependent cytotoxicity (CDC). In ADCC, the Fc region of an antibody binds to Fc receptors (Fc.gamma.Rs) on the surface of immune effector cells such as natural killers and macrophages, leading to the phagocytosis or lysis of the targeted cells. In CDC, the antibodies kill the targeted cells by triggering the complement cascade at the cell surface.

An "Fc region", or used interchangeably herein, "Fc domain" or "immunoglobulin Fc domain", contains two heavy chain fragments, which in a full antibody comprise the $C_H1$ and $C_H2$ domains of the antibody. The two heavy chain fragments are held together by two or more disulfide bonds and by hydrophobic interactions of the $C_H3$ domains.

The term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

For a detailed description of the structure and generation of antibodies, see Roth, D. B., and Craig, N. L., Cell, 94:411-414 (1998), herein incorporated by reference in its entirety. Briefly, the process for generating DNA encoding the heavy and light chain immunoglobulin sequences occurs primarily in developing B-cells. Prior to the rearranging and joining of various immunoglobulin gene segments, the V, D, J and constant (C) gene segments are found generally in relatively close proximity on a single chromosome. During B-cell-differentiation, one of each of the appropriate family members of the V, D, J (or only V and J in the case of light chain genes) gene segments are recombined to form functionally rearranged variable regions of the heavy and light immunoglobulin genes. This gene segment rearrangement process appears to be sequential. First, heavy chain D-to-J joints are made, followed by heavy chain V-to-DJ joints and light chain V-to-J joints. In addition to the rearrangement of V, D and J segments, further diversity is generated in the primary repertoire of immunoglobulin heavy and light chains by way of variable recombination at the locations where the V and J segments in the light chain are joined and where the D and J segments of the heavy chain are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity. The net effect of such rearrangements in the variable region gene segments and the variable recombination which may occur during such joining is the production of a primary antibody repertoire.

The term "hypervariable" region refers to the amino acid residues of an antibody which are responsible for antigen-binding. The hypervariable region comprises amino acid residues from a complementarity determining region or CDR [i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, th Ed. Public Health Service, National Institutes of Health, Bethesda, Md. (1991)]. Even a single CDR may recognize and bind antigen, although with a lower affinity than the entire antigen binding site containing all of the CDRs. "Framework" or "FR" residues are those variable region residues other than the hypervariable region residues.

An alternative definition of residues from a hypervariable "loop" is described by Chothia et al., J. Mol. Biol. 196: 901-917 (1987) as residues 26-32 (L1), 50-52 (L2) and 91-96 (L3) in the light chain variable domain and 26-32 (H1), 53-55 (H2) and 96-101 (H3) in the heavy chain variable domain.

The term "target binding protein" (TBP) includes aflibercept, alefacept, etanercept, abatacept, belatacept, rFVIIIFc, rFIXFc, and rilonacept, or an antibody or immunologically functional fragment of an antibody, and other recombinant proteins that contain sequences derived from CDRs or other ligand binding moieties having the desired target-binding properties such that they specifically bind a target moiety of interest.

In general, a target binding protein "specifically binds" to a target moiety or ligand of interest when it has a significantly higher binding affinity for, and consequently is capable of distinguishing, that target moiety or ligand, compared to its affinity for other unrelated targets, under similar binding assay conditions. Typically, a target binding protein is said to "specifically bind" its target when the dissociation constant ($K_D$) is $10^{-8}$ M or lower. The target binding protein specifically binds target with "high affinity" when the $K_D$ is $10^{-9}$ M or lower, and with "very high affinity" when the $K_D$ is $10^{-10}$ M or lower.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073. For example, sequence identity can be determined by standard methods that are commonly used to compare the similarity in position of the amino acids of two polypeptides. Using a computer program such as BLAST or FASTA, two polypeptide or two polynucleotide sequences are aligned for optimal matching of their respective residues (either along the full length of one or both sequences, or along a pre-determined portion of one or both sequences). The programs provide a default opening penalty and a default gap penalty, and a scoring matrix such as PAM 250 [a standard scoring matrix; see Dayhoff et al., in Atlas of Protein Sequence and Structure, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences. In calculating percent identity, the sequences being compared are aligned in a way that gives the largest match between the sequences.

The GCG program package is a computer program that can be used to determine percent identity, which package includes GAP (Devereux et al., 1984, Nucl. Acid Res. 12:387; Genetics Computer Group, University of Wisconsin, Madison, Wis.). The computer algorithm GAP is used to align the two polypeptides or two polynucleotides for which the percent sequence identity is to be determined. The sequences are aligned for optimal matching of their respective amino acid or nucleotide (the "matched span", as determined by the algorithm). A gap opening penalty (which is calculated as 3.times. the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Recommended parameters for determining percent identity for polypeptides or nucleotide sequences using the GAP program include the following:

Algorithm: Needleman et al., 1970, J. Mol. Biol. 48:443-453;

Comparison matrix: BLOSUM 62 from Henikoff et al., 1992, supra;

Gap Penalty: 12 (but with no penalty for end gaps)

Gap Length Penalty: 4

Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

The term "modification" when used in connection with proteins of interest (e.g., aflibercept, alefacept, etanercept, abatacept, belatacept, rFVIIIFc, rFIXFc, and rilonacept) include, but are not limited to, one or more amino acid changes (including substitutions, insertions or deletions); chemical modifications; covalent modification by conjugation to therapeutic or diagnostic agents; labeling (e.g., with radionuclides or various enzymes); covalent polymer attachment such as PEGylation (derivatization with polyethylene glycol) and insertion or substitution by chemical synthesis of non-natural amino acids. By methods known to the skilled artisan, proteins, can be "engineered" or modified for improved target affinity, selectivity, stability, and/or manufacturability before the coding sequence of the "engineered" protein is included in the expression cassette.

The term "derivative" when used in connection with proteins of interest, such as aflibercept, alefacept, etanercept, abatacept, belatacept, rFVIIIFc, rFIXFc, and rilonacept, refers to proteins that are covalently modified by conjugation to therapeutic or diagnostic agents, labeling (e.g., with radionuclides or various enzymes), covalent polymer attachment such as PEGylation (derivatization with polyethylene glycol) and insertion or substitution by chemical synthesis of non-natural amino acids.

Cloning DNA

Cloning of DNA is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+ mRNA, preferably membrane-associated mRNA, and the library screened using probes specific for human immunoglobulin polypeptide gene sequences. In one embodiment, however, the polymerase chain reaction (PCR) is used to amplify cDNAs (or portions of full-length cDNAs) encoding an immunoglobulin gene segment of interest (e.g., a light or heavy chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the polypeptide of interest, e.g., of the aflibercept fusion polypeptide sequence.

One source for antibody nucleic acids is a hybridoma produced by obtaining a B cell from an animal immunized with the antigen of interest and fusing it to an immortal cell. Alternatively, nucleic acid can be isolated from B cells (or whole spleen) of the immunized animal. Yet another source of nucleic acids encoding antibodies is a library of such nucleic acids generated, for example, through phage display technology. Polynucleotides encoding peptides of interest, e.g., variable region peptides with desired binding characteristics, can be identified by standard techniques such as panning.

Sequencing of DNA is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of genes and cDNAs, one of skill will readily be able to determine, depending on the region sequenced. One source of gene sequence information is the National Center for Biotechnology Information, National Library of Medicine, National Institutes of Health, Bethesda, Md.

Isolated DNA can be operably linked to control sequences or placed into expression vectors, which are then transfected into host cells that do not otherwise produce the recombinant protein of interest, to direct the synthesis of the protein in the recombinant host cells. Recombinant production of immunoglobulins and other proteins is well known in the art.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Many vectors are known in the art. Vector components may include one or more of the following: a signal sequence (that may, for example, direct secretion of the expressed protein; an origin of replication, one or more selective marker genes (that may, for example, confer antibiotic or other drug resistance, complement auxotrophic deficiencies, or supply critical nutrients not available in the media), an enhancer element, a promoter, and a transcription termination sequence, all of which are well known in the art.

Purity of Water and Other Ingredients.

The water and all other ingredients that are used in the present invention are preferably of a level of purity meeting the applicable legal or pharmacopoeial standards required for such pharmaceutical compositions and medicaments in the jurisdiction of interest, e.g., United States Pharmacopeia (USP), European Pharmacopeia, Japanese Pharmacopeia, or Chinese Pharmacopeia, etc. For example, according to the USP, Water for Injection is used as an excipient in the production of parenteral and other preparations where product endotoxin content must be controlled, and in other pharmaceutical applications, such as cleaning of certain equipment and parenteral product-contact components; and the minimum quality of source or feed water for the generation of Water for Injection is Drinking Water as defined by the U.S. Environmental Protection Agency (EPA), EU, Japan, or WHO.

Before administration to a patient, a therapeutic recombinant protein of interest should meet the applicable legal or pharmacopoeial standards required for pharmaceutical compositions and medicaments in the jurisdiction of interest as to sterility, lack of endotoxin or viral contaminants, etc.

Buffer Systems

The buffer(s) employed in the inventive method for purifying a glycosylated recombinant protein of interest from a contaminant can include a buffer in the range of about 5 to 100 mM concentration. A suitable buffer system for practicing the inventive method can be chosen from a phosphate buffer, MES buffer, TRIS buffer, BIS-TRIS buffer, histidine buffer, arginine buffer, acetate buffer, succinate buffer, citrate buffer, glutamate buffer, and lactate buffer, or the buffer can be a combination of two or more of these buffer systems. Some useful embodiments of the invention have a buffer concentration in the range of about 5 mM to about 20 mM, and other embodiments have a buffer concentration of about 5 to about 10 mM.

The buffers employed may optionally contain a non-ionic surfactant at a concentration of about 0.001 (w/v) to about 0.1% (w/v). A useful non-ionic surfactant can be polysorbate 20, polysorbate 80, Brij®35 (i.e., polyethylene glycol dodecyl ether), Poloxamer 188 (i.e., Pluronic F68; Polyethylene-Polypropylene Glycol; Polyoxyethylene-Polyoxypropylene Block Copolymer; Poly(Ethylene oxide-co-Polypropylene oxide)), or Triton™ X-100 (i.e., 4-(1,1,3,3-Tetramethylbutyl)phenyl-polyethylene glycol)). Also encompassed within "non-ionic surfactant" for purposes of practicing the present invention are alkylsaccharides or alkylglycosides (e.g., sold under the trade name ProTek® by Aegis Therapeutics, LLC; see, e.g., Maggio, Stabilizing Alkylglycoside Compositions And Methods Thereof, U.S. Pat. No. 8,133,863 B2).

Electrolytes

The inventive method for purifying a glycosylated recombinant protein of interest from a contaminant includes the step of binding the POI in the eluant pool arising from the elution of the POI from the Protein A matrix to a cation exchange matrix in a low conductivity buffer at pH 5.0-5.5. This is typically a buffer with conductivity of about 2-15 mS. Optionally, before binding the POI in the eluant pool from the Protein A matrix to the cation exchange matrix, the eluant pool can be subjected to a depth filtration through diatomaceous earth. Preferably, the diatomaceous earth used in the optional depth filtration step was pre-conditioned before use by flushing with a citrate buffer of about 0.1 M to about 1 M citrate (buffer about pH 4 to about pH 6). This pre-conditioning citrate buffer flush can significantly remove some adhering metallic cations from the diatomaceous earth to be used in the optional depth filtration.

After binding to the cation exchange matrix, the POI is then eluted from the cation exchange matrix with an electrolyte concentration gradient (linear or step gradient) of increasingly higher conductivity, up to about 40-100 mS, into a CEX eluant pool. Thus, a suitable gradient range for the CEX elution has a conductivity range of 2-100 mS. Depending on the particular POI, the effective gradient range can be 2-70 mS, for example, a useful gradient range for purifying aflibercept increase the buffer conductivity in a range from about 15 mS up to about 66 mS. Useful electrolytes for adjusting conductivity include sodium chloride, potassium chloride, and sodium sulfate.

The next step of the inventive method is loading the CEX eluant pool onto a hydrophobic interaction chromatography (HIC) matrix in a high conductivity buffer at pH 5.0-6.0 and washing the HIC matrix (with several volumes of high conductivity buffer, e.g., typically three or more column volumes). The high conductivity buffer for HIC loading is typically about 40-100 mS in conductivity. The HIC washing buffer can be the same buffer as the high conductivity HIC loading buffer or a different buffer, but should be of the same or greater conductivity, and at pH 5.0-6.0. Useful electrolytes for adjusting conductivity include sodium chloride, potassium chloride, and sodium sulfate.

Exemplary Embodiments of the Invention

By way of further illustration, the following numbered embodiments are encompassed by the present invention:

Embodiment 1

A method for purifying a glycosylated recombinant protein of interest from a contaminant, comprising:
(a) loading onto a Protein A matrix, at about neutral pH, a host cell culture supernatant or filtrate comprising the glycosylated recombinant protein of interest (POI) and a galectin host cell protein (HCP) contaminant, wherein the POI comprises the $C_H2$ and $C_H3$ domains of an immunoglobulin Fc domain and one or more terminal beta-galactosyl residues to which the galectin-3 contaminant is reversibly bound;
(b) washing the Protein A matrix that has the POI bound to it, with a buffer at about pH 6.0-6.5, comprising 1-3 M calcium chloride;
(c) eluting the POI from the Protein A matrix with a buffer comprising citric acid or a citrate salt below about pH 4 into an eluant pool, and:
   (i) if the eluant pool is more basic than the pH range of pH 3.3-3.7, titrating the eluant pool to pH 3.3-3.7 with citric acid, and
   (ii) optionally, keeping the eluant pool at pH 3.3-3.7 for a period sufficient for viral inactivation;
(d) binding the POI in the eluant pool from (c) to a cation exchange matrix in a low conductivity buffer of about 2-15 mS, at pH 5.0-5.5;
(e) eluting the POI from the cation exchange matrix with an electrolyte concentration gradient of increasingly higher conductivity, up to about 40-100 mS, into a CEX eluant pool; and
(f) loading the CEX eluant pool onto a hydrophobic interaction chromatography (HIC) matrix in a high conductivity buffer at pH 5.0-6.0 and washing the HIC matrix, whereby the POI is separated from the galectin HCP contaminant.

Embodiment 2

The method of Embodiment 1, wherein in (b) washing the Protein A matrix that has the POI bound to it, is with a buffer comprising 2 to 2.7 M calcium chloride.

Embodiment 3

The method of Embodiments 1-2, wherein the POI is selected from aflibercept, alefacept, etanercept, abatacept, belatacept, rFVIIIFc, rFIXFc, and rilonacept.

Embodiment 4

The method of Embodiments 1-3, wherein the POI is aflibercept.

Embodiment 5

The method of Embodiments 1-4, wherein the galectin HCP contaminant is galectin-3.

Embodiment 6

The method of Embodiments 1-5, wherein the host cell culture supernatant or filtrate further comprises a metallic cation contaminant, and wherein the POI is also separated from the metallic cation contaminant.

Embodiment 7

The method of Embodiments 1-6, wherein the metallic cation contaminant is selected from aluminum, barium, calcium, cobalt, copper, zinc, iron, magnesium, manganese, mercury, nickel, and strontium cations.

Embodiment 8

The method of Embodiments 1-7, wherein the metallic cation contaminant is an iron cation.

Embodiment 9

The method of Embodiments 1-8, further comprising, before binding the POI in the eluant pool from (c) to a cation exchange matrix, subjecting the eluant pool to depth filtration comprising filtration through diatomaceous earth.

Embodiment 10

The method of Embodiments 1-9, wherein the diatomaceous earth was pre-conditioned with a citrate buffer.

The following working examples are illustrative and not to be construed in any way as limiting the scope of the invention.

EXAMPLES

Example 1: Materials and Methods

The water used in all the experiments described herein was purified using a Milli-Q® Integral Water Purification System (Merck), since the POI was not intended for ultimate administration to patients.

CHO Galectin Removal Studies:

High Throughput Screening ("HTS").

Downstream HTS studies were performed using a Tecan Freedom EVO® robotic liquid handling system (Tecan US, Research Triangle Park, N.C., USA). The robotic liquid handling system was configured with Te-Chrom components to facilitate automated micro-chromatography. Measurements for concentration and turbidity were performed on an integrated microplate reader. Resins were acquired as pre-packed 450-µL RoboColumns® from Atoll (Weingarten, Germany); eight such columns were operated in parallel in either bind-and-elute (BEM) mode or flow-through (FT) mode, depending on the experiment.

Protein a Chromatography.

HTS Protein A wash screening studies were performed in BEM using RoboColumns® containing MabSelect SuRe® Protein A resin (GE Healthcare, Piscataway, N.J., USA). The columns were equilibrated with equilibration buffer (25 mM Tris, 100 mM NaCl, pH 7.4), and then loaded with harvested cell culture fluid to approximately 10 g per liter of resin. Following loading, a 3-column volume ("CV") equilibration wash step with the equilibration buffer ("EQ") was performed. Each column was then washed with one of the following wash buffer solutions for experimental comparison:

25 mM Tris, 480 mM lactose pH 7.3;
25 mM MES, 2 M $CaCl_2$) pH 6.0;
25 mM MES, 2 M $CaCl_2$) pH 6.5;
25 mM Tris, 2 M $CaCl_2$) pH 7.0,
25 mM MES, 750 mM Arginine pH 6.0;
25 mM MES, 750 mM Arginine pH 6.5; or
25 mM Tris, 750 mM Arginine pH 7.0.

A second experiment was performed using wash two conditions with increasing concentrations of calcium chloride (0.25-2.63M) buffered with 25 mM MES, pH 6 for 4 column volumes. A third wash was then performed with two column volumes of EQ. The columns were eluted with four column volumes of 25 mM citrate pH 3.6 into 96-deep well plates (Qiagen Sciences, Germantown, Md., USA). The subsequent elution pools were neutralized to pH 5 using 2 M Tris base. The elution pools from each column were measured for product concentration by analytical Protein A HPLC and galectin-3 ELISA (R&D systems, Minneapolis, Minn., USA) using the protocol recommended by the manufacturer with a CHO galectin-3 protein standard.

CEX Chromatography.

An HTS NaCl elution gradient screen was performed using RoboColumns® containing Fractogel® $SO_3^-$ or Fractogel® $COO^-$ (EMD Millipore, Billerica, Mass., USA) and run at 20 cm/hr. The CEX columns were equilibrated to the target pH (pH 4.5-6.0) and conductivity (approximately 3-8 mS/cm) prior to loading. Following equilibration, the columns were loaded from 15 to 30 g/L resin. Following a wash step with equilibration buffer, the columns were eluted with a stepwise sodium chloride gradient. Elution fractions (1 CV/fraction) were collected into 96-deep well plates (Qiagen Sciences, Germantown, Md., USA) for further analysis including product concentration analysis by absorbance at 280 nm (A280) and purity by size exclusion chromatography (SEC), the galectin-3-specific ELISA, and a CHO host cell protein (HCP)-specific ELISA (Cygnus, Southport, N.C.) using the protocol recommended by the manufacturer. Results from individual fractions were used to generate pseudo-chromatograms. Cumulative results from each fraction were used to calculate yield and mass balance.

Bench scale chromatography experiments were conducted using an Äktaexplorer 100 or an Äktapurifier 100 (GE Healthcare Life Sciences, Piscataway, N.J., USA) liquid chromatography systems. Fractogel® $SO_3^-$ (EMD Millipore, Billerica, Mass., USA) and Fractogel® $COO^-$ resins were packed into 1.15 cm ID or 3.2 cm ID Vantage columns (EMD Millipore, Billerica, Mass., USA) to a bed height of approximately 15-20 cm. Runs were performed at 140 to 180 cm/hr. The CEX columns were equilibrated to pH 5.0 or pH 5.5 in a sodium acetate buffer at a conductivity of approximately 6 mS/cm prior to loading. Columns were then loaded with neutralized Protein A eluant pool to approximately 20 to 30 g/L resin, washed with equilibration buffer, and eluted over a linear NaCl gradient, increasing the NaCl concentration by 50 mM NaCl per column volume (CV) for 10 to 20 CVs. The column effluent pH, conductivity, and absorbance were monitored during the chromatography runs. During the elution phase, fractions were collected and measured for product concentration by A280, SEC, CHO HCP-specific ELISA, and galectin-3-specific ELISA. Pool recovery and purity were calculated from individual fractions.

Hic Chromatography.

An HTS NaCl gradient screen was performed using RoboColumns® packed with Toyopearl® Butyl 650M (Tosoh, King of Prussia, Pa., USA) and Phenyl Sepharose® Fast Flow High Sub (GE Healthcare, Piscataway, N.J., USA). The columns were loaded to 25 g product per liter of resin (g/Lr) with neutralized Protein A pools conditioned with NaCl. The elution salt gradients were performed in a stepwise fashion from high to low salt concentration. The buffer/salt conditions screened included sodium acetate/ NaCl, sodium MES/NaCl, sodium acetate/sodium sulfate, sodium citrate and sodium phosphate. All steps were performed at 20 cm/hr. Flow-through and elution fractions were analyzed for protein concentration (by A280 and SEC) and by galectin-3-specific ELISA.

HTS HIC product flow-through screens were performed using RoboColumns® packed with Toyopearl® Butyl 650M and run at 20 cm/hour. The load was neutralized Protein A eluant pool material and was applied to the columns in 1-CV increments up to 70 to 125 g/L resin. Wash volumes of 6-9 CVs were also performed in 1-CV increments. Fractions were collected and analyzed spectrographically for protein concentration (A280) and by galectin-3-specific ELISA.

Bench scale runs were performed on the Äktapurifier 100 (GE Healthcare Life Sciences) at 180 cm/hour with Toyopearl® Butyl 650M resin packed into Vantage® L chromatography columns in sizes ranging from 1.15 cm inner diameter (ID) by 25-cm bed height to 3.2-cm ID by 25-cm bed height. Columns were loaded from 100 to 125 g/Lr. The flow-through product pool was either collected as fractions or collected based on UV absorbance. Fractions or flow-through wash/product pool samples were analyzed for protein concentration by A280, SEC, CHO HCP-specific ELISA, and galectin-3-specific ELISA.

Iron Removal Studies:

Protein A chromatography. HTS Protein A wash screens were performed using RoboColumns® packed with Mab-Select SuRe® Protein A and run at 45 cm/hour. Columns were loaded to 12 g/Lr and then washed with 3 CVs of EQ followed by 4 CVs of a different buffer condition in the second wash (Wash 2). Wash 2 buffers that were screened included the following conditions:
50 mM sodium citrate at pH 6.0;
50 mM sodium citrate at pH 7.0;
200 mM sodium citrate at pH 6.0;
200 mM sodium citrate at pH 7.0;
125 mM Tris, 500 mM NaCl, pH 7.4;
25 mM Tris, 100 mM NaCl, pH 7.4;
25 mM Tris, 100 mM NaCl, 5 mM EDTA, pH 7.0; or
25 M Tris, 100 mM NaCl, 5 mM EDTA, pH 8.0.
Wash 2 was followed up by an additional 3 CVs of equilibration buffer. Wash 2 and elution fractions were analyzed for protein concentration as described above. These fractions were also analyzed by Brooks Analytical Laboratory (Bothell, Wash., USA) for iron levels using a conventional inductively coupled plasma mass spectrometry (ICP-MS) assay.

Bench Scale Protein a, Low pH Viral Inactivation ("VI"), and CEX Experiment. The lead Protein A Wash 2 condition was run at bench scale on an Aktapurifier 100 using a 1.15 cm ID by 25 cm column height packed with MabSelect SuRe® Protein A at 250 cm/hour. The column was loaded with harvested cell culture fluid (HCCF) to 19 g/L resin. The volume of wash buffers were reduced to 2 CVs of EQ for wash 1, 3 CVs of Wash 2, and 3 CVs of EQ for wash 3. Two different Wash 2 conditions were compared: EQ buffer (25 mM Tris, 100 mM NaCl, pH 7.4) and 500 mM sodium citrate, pH 5.5. Elution buffers of 100 mM sodium acetate and 25 mM sodium citrate, both at pH 3.6, were also compared. Elution pools were divided into two aliquots. One aliquot was titrated to a lower pH of 3.5 using 2 M citric acid, held for 60 minutes to simulate the low pH viral inactivation (VI) operation, and was neutralized to pH 5.0 using 2 M Tris base. The second aliquot was only neutralized to pH 5.0 using 2 M Tris base.

The four resulting product pools, i.e.: sodium acetate elution with and without low pH hold and sodium citrate elution with and without low pH hold, were purified by HT-CEX chromatography using RoboColumns® packed with Fractogel® COO⁻. The columns were loaded to 20 g/Lr and the NaCl elution gradient was performed in 100 mM sodium acetate (pH 5.5) buffer at a slope of 40 mM NaCl/CV in a stepwise fashion. All steps were performed at 20 cm/hour. Fractions were pooled and analyzed for protein concentration by A280. Samples from all steps were analyzed for iron by inductively coupled plasma mass spectrometry (ICP-MS).

Example 2: CHO Galectin-3 Removal from Aflibercept

Protein a Chromatography Wash Screening Experiments.

HTS screening experiments were performed using buffers containing 2M $CaCl_2$ or 750 mM arginine buffers as "Wash 2" to determine if they could disrupt the interaction between CHO galectin-3 and aflibercept. The experiment was performed using eight (8) MabSelect SuRe® Protein A-packed RoboColumns® on a Tecan liquid handler. The column equilibration, post load wash 1 and wash 3 were performed using equilibration buffer ("EQ"; 25 mM Tris, 100 mM NaCl, pH 7.4). The elution was performed using 25 mM citrate, pH 3.6 and all pools were neutralized to pH 5.0 with 2M Tris base. Harvested cell culture fluid containing aflibercept was used for loading, and all columns were loaded with the same product mass. For Wash 2, 480 mM lactose was used as a positive control since it contains a beta-galactose moiety that can compete for galectin-3 binding. Equilibration buffer (EQ; 25 mM Tris, 100 mM NaCl, pH 7.4) was used as a Wash 2 negative control. The lactose-containing buffer was able to remove 2 logs of galectin-3 as compared to EQ (Table 1, below). The 2M $CaCl_2$ wash removed 1 log of galectin-3 more than EQ, with no significant product loss observed at pH 6.0 and pH 6.5. A significant amount of product was removed by the 2 M $CaCl_2$ wash at pH 7.0, indicating this pH is not ideal for this particular product. The arginine wash removed a little over 0.5 logs of galectin-3 as compared to EQ, with significant yield loss observed during the wash at pH 6.0 and pH 6.5, but not pH 7.0.

TABLE 1

Results from initial Protein A Wash 2 screening.

| Condition | % Yield loss | CHO Galectin-3 (ng/ml) | CHO Galectin-3 (ppm) |
|---|---|---|---|
| HCCF load | NA | 137.8 | 156.6 |
| EQ | 3.2 | 124 | 45.8 |
| EQ + 480 mM lactose | 3.5 | 0.83 | 0.30 |
| 25 mM MES, 2M $CaCl_2$ pH 6.0 | 8.3 | 12.5 | 5.1 |
| 25 mM MES, 2M $CaCl_2$ pH 6.5 | 4.0 | 14.5 | 5.6 |
| 25 mM Tris, 2M $CaCl_2$ pH 7.0 | 31.9 | 8.2 | 5.0 |
| 25 mM MES, 750 mM Arginine pH 6.0 | 35.3 | 28.3 | 21.3 |
| 25 mM MES, 750 mM Arginine pH 6.5 | 17.1 | 56.3 | 23.6 |
| 25 mM Tris, 750 mM Arginine pH 7.0 | 4.1 | 60.6 | 23.6 |

HCCF = harvested cell culture fluid;
NA = Not applicable;
EQ = equilibration buffer, i.e., 25 mM Tris, 100 mM NaCl, pH 7.4.

A second round of experiments was performed as above using MabSelect SuRe® Protein A-packed RoboColumns® to estimate the range of calcium chloride where effective galectin-3 removal could be expected. The Wash 2 $CaCl_2$) concentration was tested from 0.25 M through 2.63 M, buffered with 20 mM MES at pH 6.0. EQ was used as a negative control. Results are shown in Table 2, below. Relative to the control condition, the Protein A step yields were consistent up to 2.40 M $CaCl_2$). At higher $CaCl_2$) concentrations, a decrease in the step yield was observed and is most likely specific to the product used for the study (aflibercept), but would not necessarily be observed with other molecules. Independent of step yield, when compared to the harvested cell culture fluid (HCCF), the galectin-3 clearance was high across the conditions tested. When compared to the galectin-3 concentration in a Protein A eluant pool with no $CaCl_2$) wash, there was no removal of galectin-3 at 0.25 M $CaCl_2$) and only 4% removal of galectin-3 at 0.5 M $CaCl_2$). Additional galectin-3 removal was modest (24%) at 1.0 M $CaCl_2$). At 2.0-2.63 M $CaCl_2$) an additional 42-52% of galectin-3 removal was observed. With this glycosylated recombinant protein molecule, it was observed that, compared to the control, additional galectin-3 removal could be achieved by employing a $CaCl_2$) wash at a concentration of ≥1.0 M. It was also observed that effective galectin-3 removal occurred up to 2.63 M $CaCl_2$) in this experiment. From these experimental results, one would expect that even higher $CaCl_2$ concentrations (limited by the solubility of calcium chloride) can be effective for galectin-3 removal. Likewise, depending on the interaction between galectin-3 and the POI, lower $CaCl_2$ concentrations may be useful for other glycosylated recombinant protein products. In practicing the inventive method the selection of a suitable $CaCl_2$ concentration involves a desirable balance of step yield for the protein of interest with galectin clearance.

TABLE 2

Results from Protein A Wash 2 $CaCl_2$ screening study.

| Column | $CaCl_2$ concentration (mM) | Yield (%) | Galectin-3 concentration (ng/mg) | Additional removal compared to control (%) |
|---|---|---|---|---|
| Load | NA | NA | 304.8 | NA |
| Column 1 | 0 | 82.5 | 14.6 | NA |
| Column 2 | 0.25 | 90.2 | 15.4 | None |
| Column 3 | 0.50 | 88.3 | 14.0 | 4.1 |
| Column 4 | 1.00 | 89.5 | 11.1 | 24.0 |
| Column 5 | 2.00 | 87.6 | 7.0 | 52.0 |
| Column 6 | 2.40 | 86.3 | 8.5 | 41.8 |
| Column 7 | 2.50 | 65.4 | 8.1 | 44.5 |
| Column 8 | 2.63 | 50.8 | 8.2 | 43.8 |

NA = Not applicable.

CEX Chromatography Screening Experiments.

Figure 2:
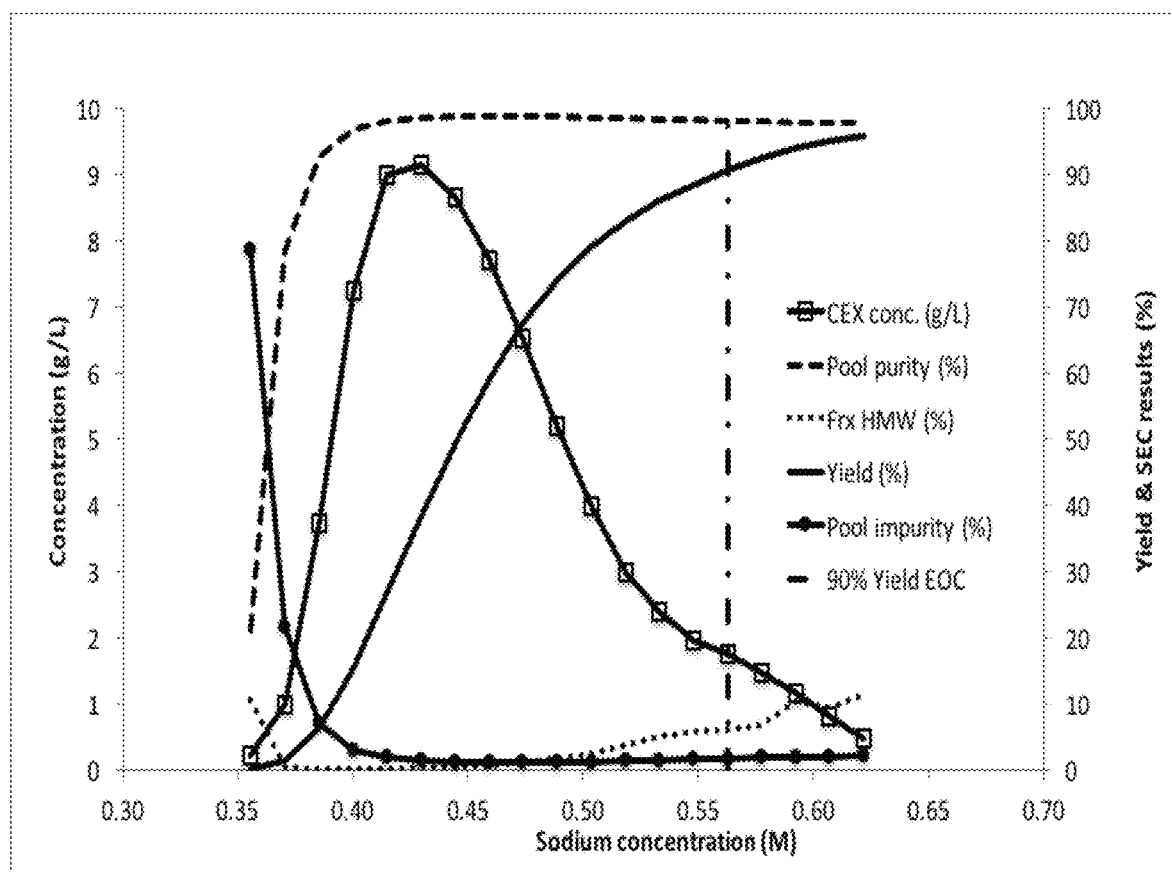
FIG. 2 shows a comparison of data from Fractogel® $SO_3^-$ CEX gradient elution fractions: product concentration, HMW, cumulative product yield and cumulative pool monomer (purity). The vertical dashed line indicates end of collection (EOC) target to achieve 90% yield.

Initial experiments with CEX resins were performed at bench scale to identify operating conditions that resulted in adequate removal of aggregated product and CHO host cell proteins including the specific protein galectin-3, while maintaining high recovery. Screening studies with Fractogel® $SO_3^-$ using a 10-CV NaCl elution gradient indicated that high yield was achievable, however with only a modest (<20%) reduction in high molecular weight (HMW) species at approximately 90% yield. FIG. 1 shows the CEX chromatogram overlaid with dimer, oligomer, and total HMW. FIG. 2 shows the CEX chromatogram overlaid with calculated eluant pool purity and total eluant pool HMW content.

Figure 3:
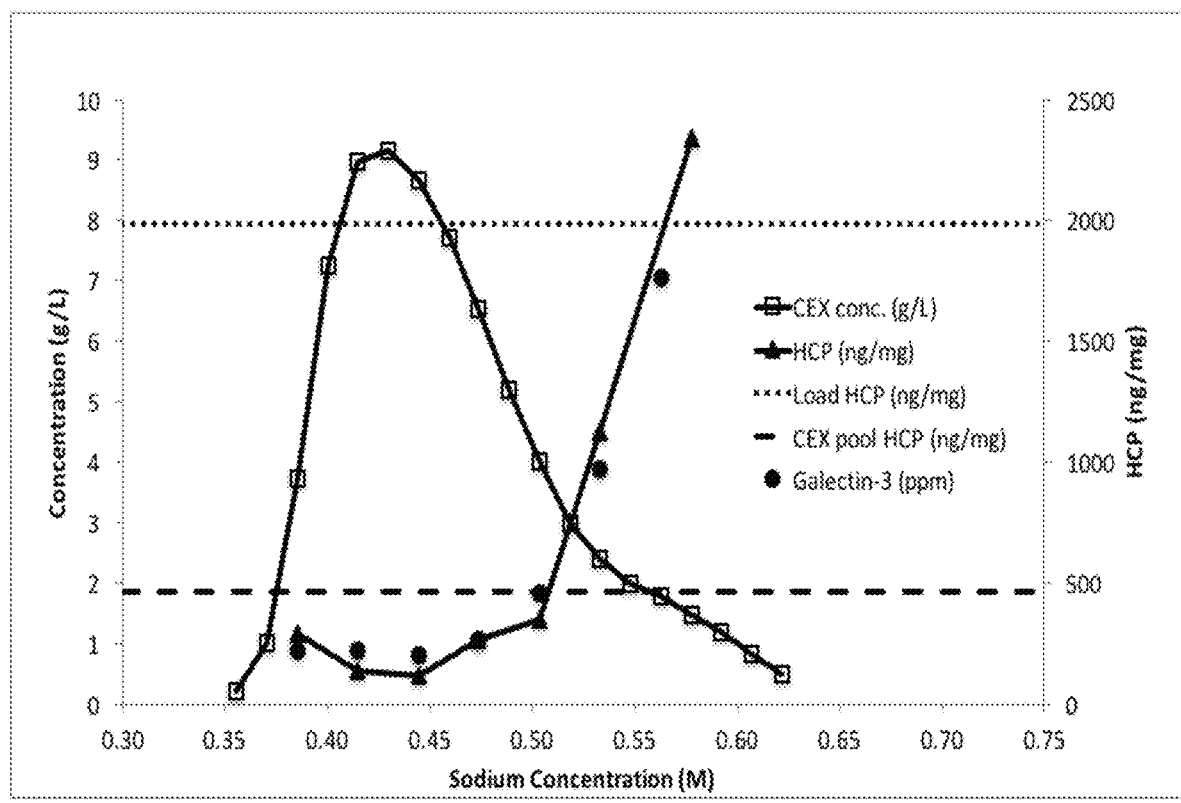
FIG. 3 shows a comparison of galectin-3 and total host cell protein (HCP) levels in individual CEX elution gradient fractions. The horizontal line with short dashes denotes the total CHO HCP level in the CEX load. The horizontal line with long dashes denotes the total CHO HCP level in the CEX pool.
Figure 4A:
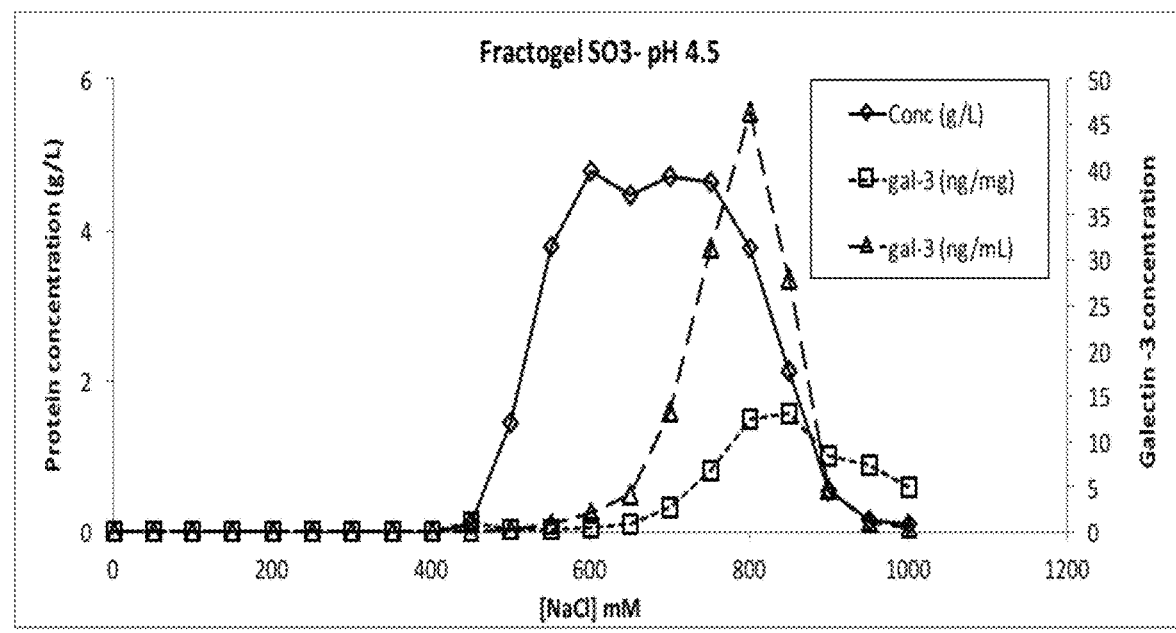
FIG. 4A shows results from pseudo-chromatograms and galectin-3 concentration of individual fractions from a Fractogel® $SO_3^-$-filled RoboColumn® operated at pH 4.5. Diamonds represent product concentration (g/L), squares represent galectin-3 concentration (ng/mg), and triangles represent galectin-3 concentration (ng/mL).
Figure 4B:
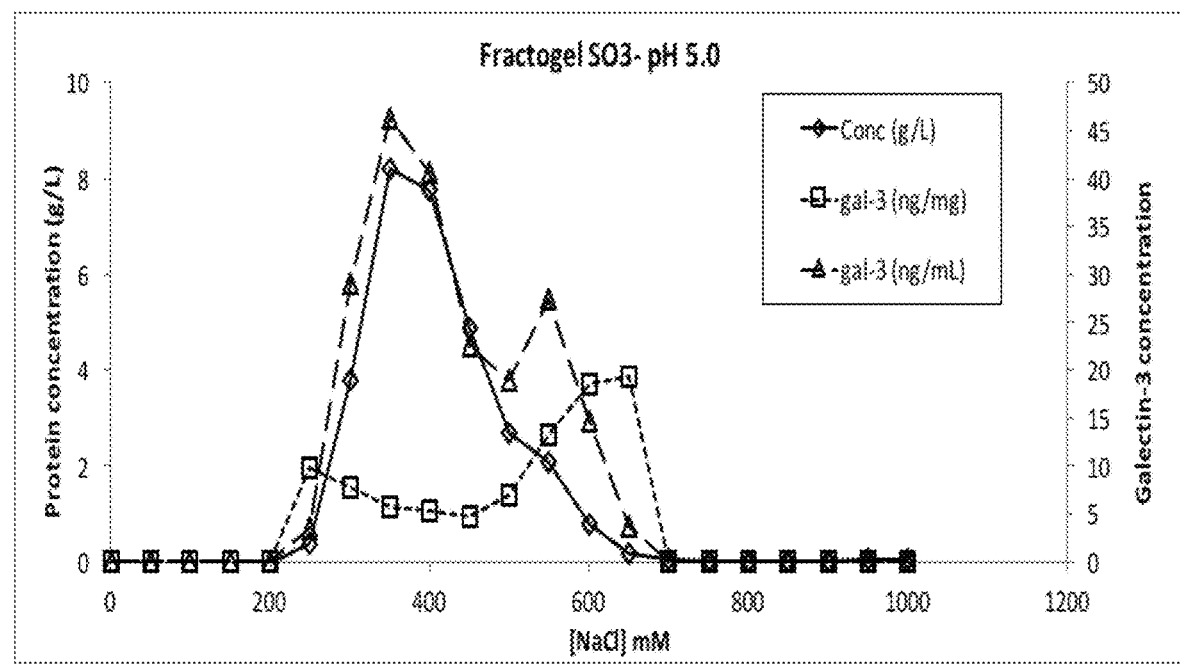
FIG. 4B shows results from pseudo-chromatograms and galectin-3 concentration of individual fractions from a Fractogel® $SO_3^-$-filled RoboColumn® operated at pH 5.0. Diamonds represent product concentration (g/L), squares represent galectin-3 concentration (ng/mg), and triangles represent galectin-3 concentration (ng/mL).
Figure 4C:
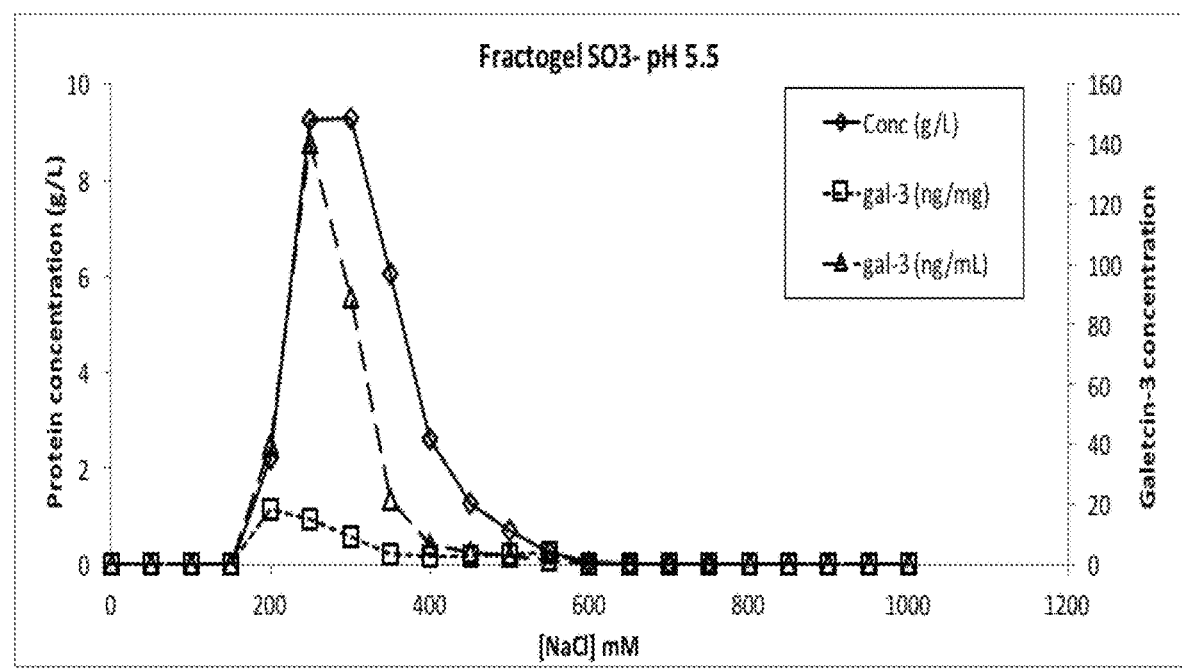
FIG. 4C shows results from pseudo-chromatograms and galectin-3 concentration of individual fractions from a Fractogel® $SO_3^-$-filled RoboColumn® operated at pH 5.5. Diamonds represent product concentration (g/L), squares represent galectin-3 concentration (ng/mg), and triangles represent galectin-3 concentration (ng/mL).
Figure 4D:
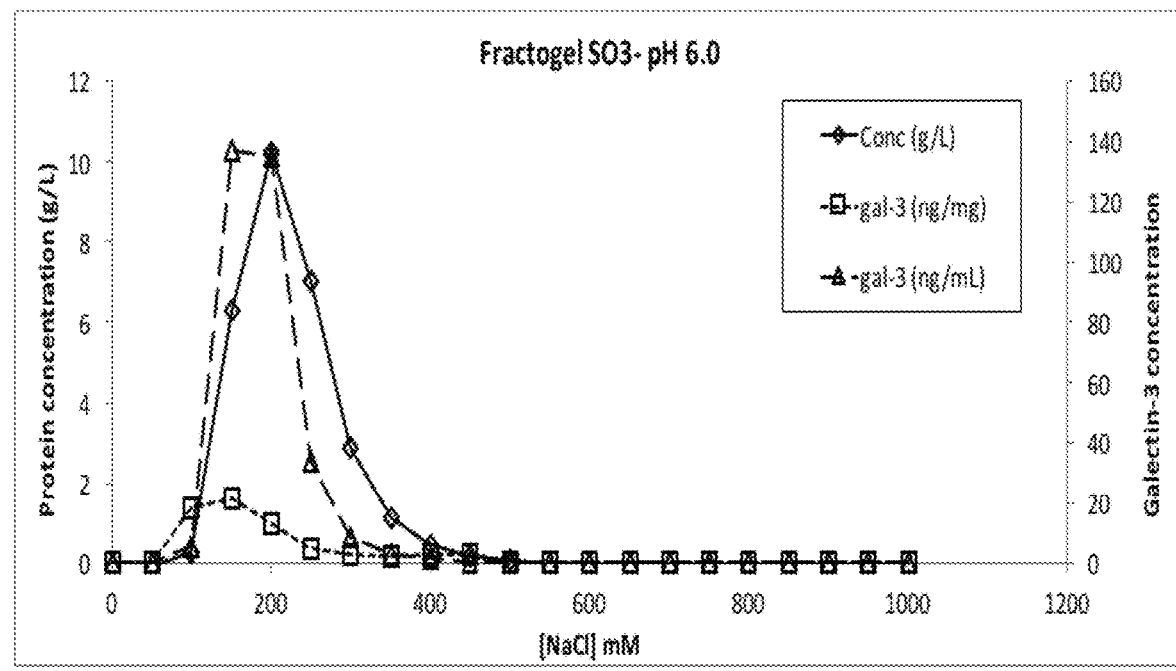
FIG. 4D shows results from pseudo-chromatograms and galectin-3 concentration of individual fractions from a Fractogel® $SO_3^-$-filled RoboColumn® operated at pH 6.0. Diamonds represent product concentration (g/L), squares represent galectin-3 concentration (ng/mg), and triangles represent galectin-3 concentration (ng/mL).
Figure 5A:
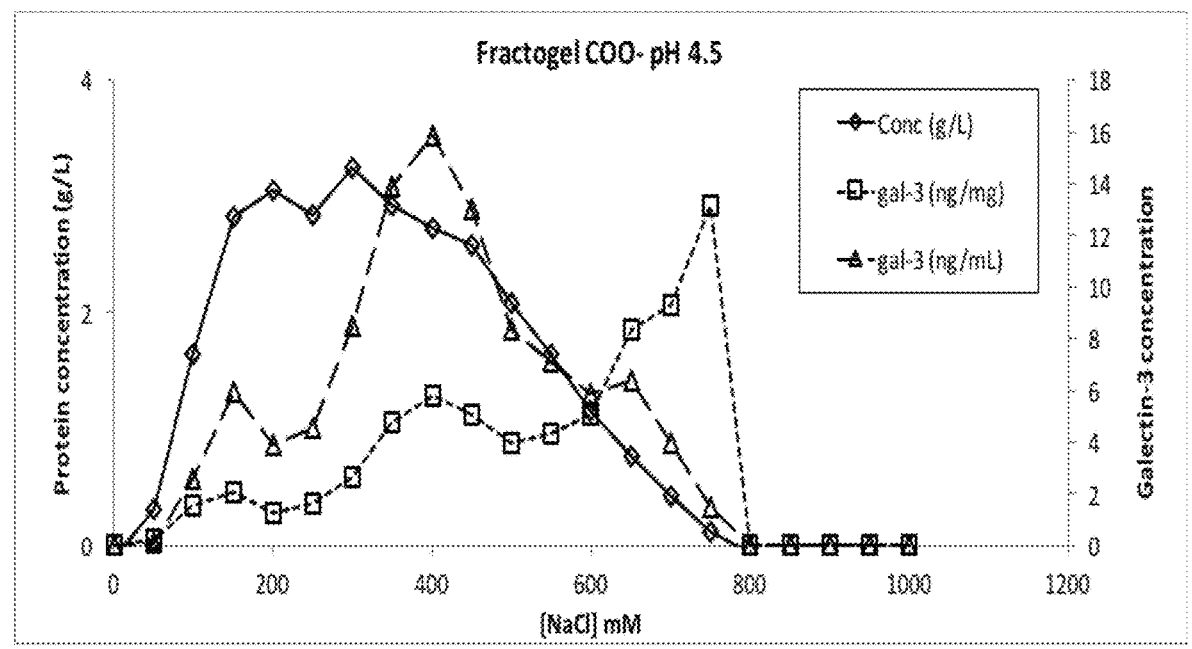
FIG. 5A shows results from pseudo-chromatograms and galectin-3 concentration of individual fractions from a Fractogel® $COO^-$-filled RoboColumn® operated at pH 4.5. Diamonds represent product concentration (g/L), squares represent galectin-3 concentration (ng/mg), and triangles represent galectin-3 concentration (ng/mL).
Figure 5B:
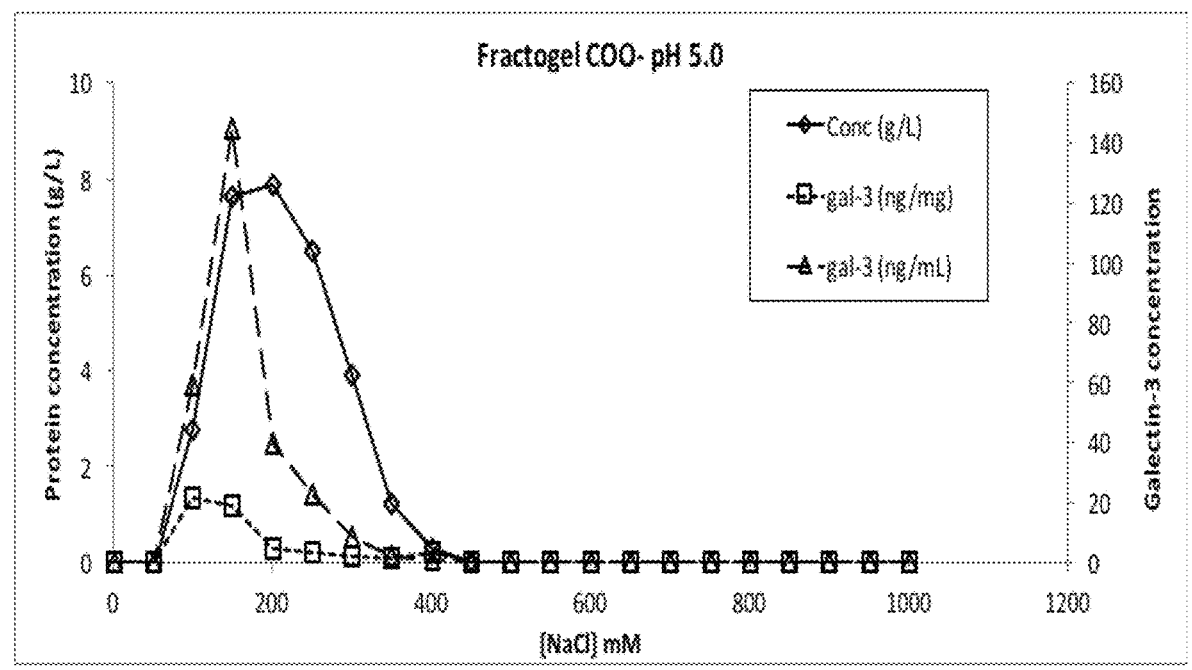
FIG. 5B shows results from pseudo-chromatograms and galectin-3 concentration of individual fractions from a Fractogel® $COO^-$-filled RoboColumn® operated at pH 5.0. Diamonds represent product concentration (g/L), squares represent galectin-3 concentration (ng/mg), and triangles represent galectin-3 concentration (ng/mL).
Figure 5C:
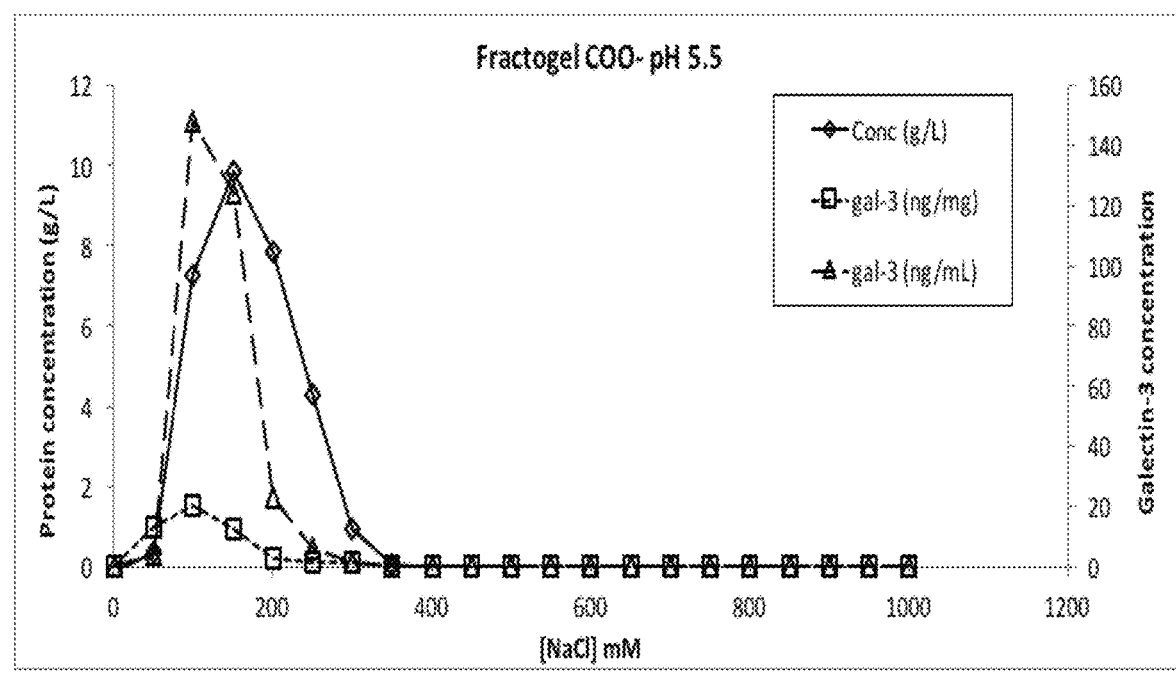
FIG. 5C shows results from pseudo-chromatograms and galectin-3 concentration of individual fractions from a Fractogel® $COO^-$-filled RoboColumn® operated at pH 5.5. Diamonds represent product concentration (g/L), squares represent galectin-3 concentration (ng/mg), and triangles represent galectin-3 concentration (ng/mL).
Figure 5D:
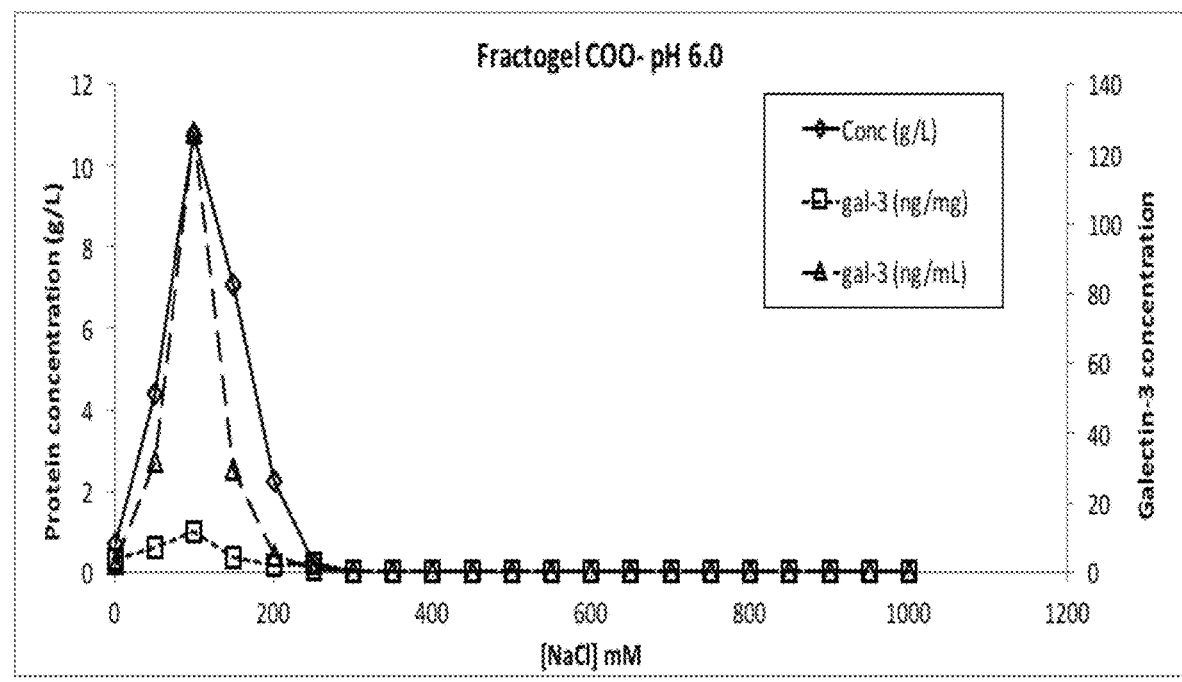
FIG. 5D shows results from pseudo-chromatograms and galectin-3 concentration of individual fractions from a Fractogel® $COO^-$-filled RoboColumn® operated at pH 6.0. Diamonds represent product concentration (g/L), squares represent galectin-3 concentration (ng/mg), and triangles represent galectin-3 concentration (ng/mL).

To determine whether this CEX run could also remove galectin-3, the peptide map-based multi-attribute method ("MAM"; Rogers, R. et al., *Development of a quantitative mass spectrometry multi-attribute method for characterization, quality control testing and disposition of biologics*, mAbs, 7(5): 881-890 (2015)) was used to search for and quantitate galectin-3 levels in the elution fractions (Table 3, below). Additionally, Table 3 shows the concentration of total CHO host cell proteins, as measured by the Cygnus HCP ELISA. FIG. 3 shows the relative of galectin-3, general host cell protein (HCP), and the product of interest in the various NaCl elution gradient fractions.

Analysis of the individual fractions eluting from the Fractogel® $SO_3^-$ column showed that there was a small amount of HCP and galectin-3 that co-elutes with the POI. However, after >80% of the POI elutes, there was a sharp increase in the elution of both total HCP and galectin-3. This indicates that Fractogel $SO_3^-$ can separate significant amounts of galectin-3 from the product while maintaining high product recovery. Additionally, the elution trend for galectin-3 mirrors that of total HCP, implying that a large portion of the HCP observed in the product load was galectin-3. This further implies that the host cell protein (HCP) removal detected by the Cygnus HCP ELISA is a good indicator of galectin-3 removal.

Based on the observation that Fractogel® $SO_3^-$ could provide some galectin-3 removal, HTS was used to screen CEX operating conditions for improved galectin-3 removal. In these studies, a strong and weak cation exchanger Fractogel® $SO_3^-$ and Fractogel® $COO^-$, respectively, were screened at pH 4.5, 5.0, 5.5, and 6.0 on RoboColumns® using a Tecan liquid handling system. Columns were loaded to 30 g/L resin and eluted with a 50 mM/CV stepwise NaCl gradient over 20 CVs. Fractions of the elution gradient were collected and measured for product concentration and galectin-3 concentration by ELISA (FIG. 4A-D and FIG. 5A-D).

A comparison of the relative retention of the POI and galectin-3 on Fractogel® $SO_3^-$ and Fractogel® $COO^-$ revealed that, at lower pH, the galectin-3 eluted in the tail portion of the POI elution peak. As the pH increased to pH 5.0 for Fractogel® $COO^-$ and pH 5.5 for Fractogel® $SO_3^-$, the galectin-3 elution shifted to earlier in the gradient, thus overlapping with POI elution peak. For Fractogel® $COO^-$, the galectin-3 showed some separation from the POI on the pH 4.5 gradient, however it was modest compared to Fractogel® $SO_3^-$.

Figure 6:
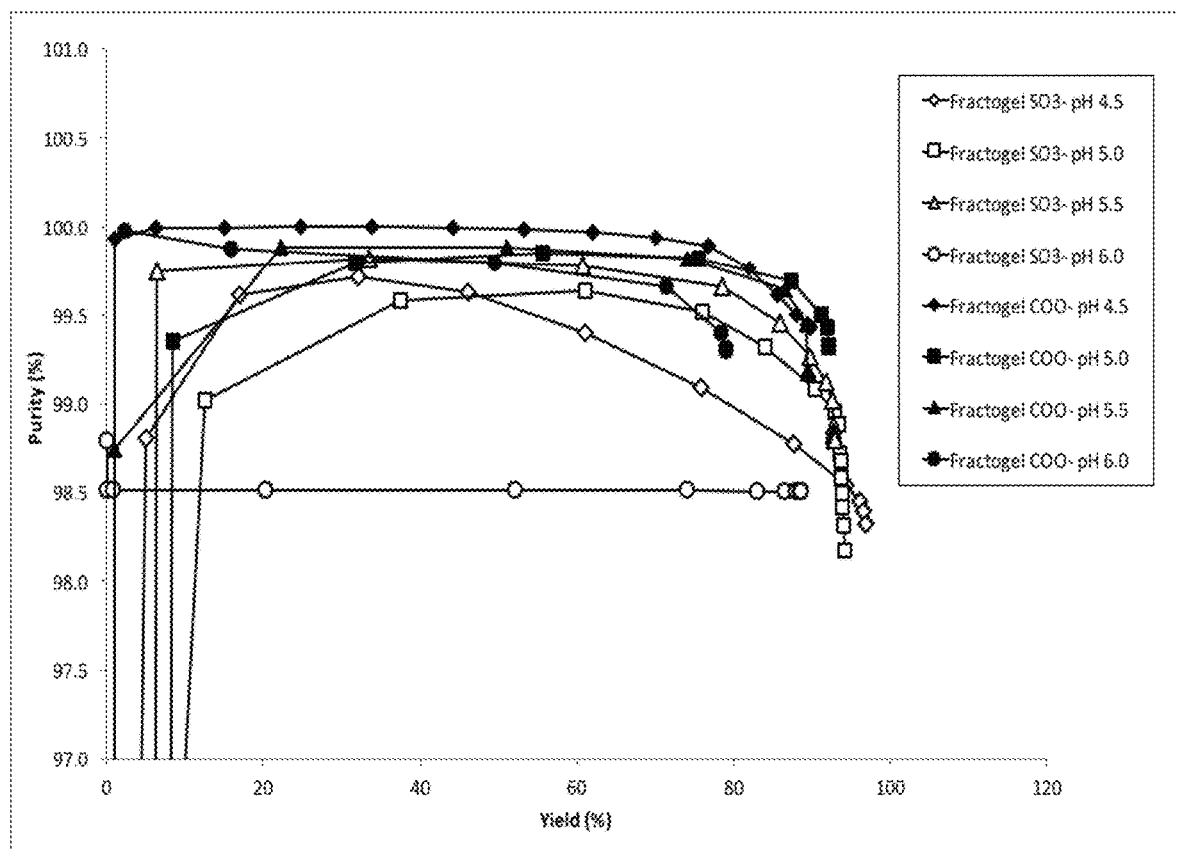
FIG. 6 shows a comparison of percent step yield versus percent purity (monomeric product) for the CEX resin screen. Results from Fractogel® SO$_3^-$ are represented by open symbols, and results from Fractogel® COO$^-$ are represented by solid symbols. Diamonds represent pH 4.5, squares represent pH 5.0, triangles represent pH 5.5 and circles represent pH 6.0.
Figure 7:
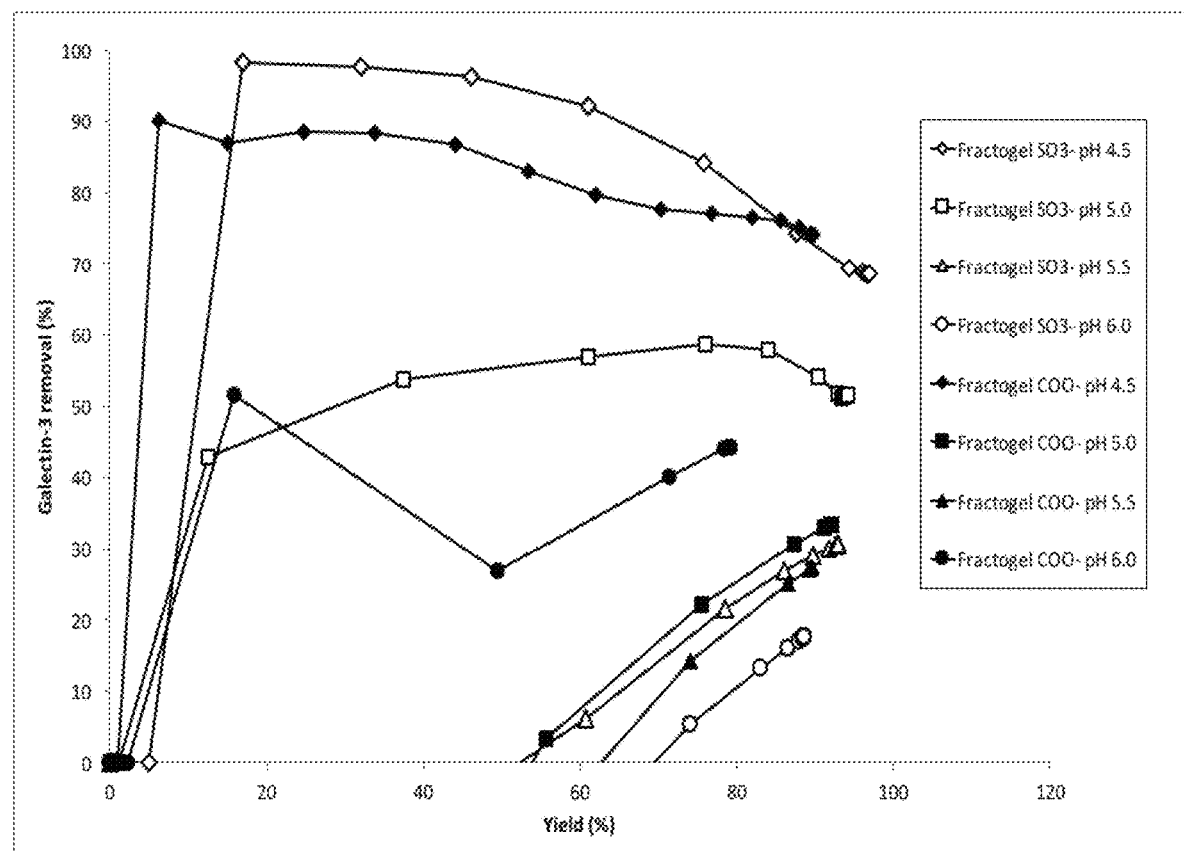
FIG. 7 shows a comparison of percent step yield versus percent galectin-3 removal for the CEX resin screen. Results from Fractogel® SO$_3^-$ are represented by open symbols, and results from Fractogel® COO$^-$ are represented by solid symbols. Diamonds represent pH 4.5, squares represent pH 5.0, triangles represent pH 5.5 and circles represent pH 6.0.

A comparison of product recovery versus % product monomer by size exclusion chromatography is shown in FIG. 6. Product recovery versus galectin-3 removal by ELISA is shown in FIG. 7.

TABLE 3

Galectin-3 and Total CHO HCP concentrations in individual CEX elution gradient fractions.

| Sample | Fraction number | CHO HCP concentration by Cygnus ELISA (ng/mg) | Galectin-3 concentration by MAM (ppm) |
|---|---|---|---|
| Load | NA | 1988 | NT |
| UBAV | NA | NT | NT |
| B2 | 1 | NT | NT |
| B1 | 2 | NT | NT |
| C1 | 3 | 289 | 220.79 |
| C2 | 4 | NT | NT |
| C3 | 5 | 136 | 217.32 |
| C4 | 6 | NT | NT |
| C5 | 7 | 115 | 202.41 |
| C6 | 8 | NT | NT |
| C7 | 9 | 267 | 264.81 |
| C8 | 10 | NT | NT |
| C9 | 11 | 347 | 458.62 |
| C10 | 12 | NT | NT |
| C11 | 13 | 1127 | 969.91 |
| C12 | 14 | NT | NT |
| D12 | 15 | NT | 1762.64 |
| D11 | 16 | 2337 | NT |
| D10 | 17 | NT | 2040.47 |
| D9 | 18 | NT | NT |
| D8 | 19 | NT | NT |
| Total Pool | NA | 466 | NT |
| Strip | NA | NT | NT |

HCP = host cell protein;
NA = Not applicable;
NT = Not tested;
MAM = mass spectrometry multi-attribute method (see, Rogers, R. et al., mAbs, 7(5): 881-890 (2015))

Overall removal of high molecular weight (HMW) species was also monitored by SEC during these experiments and it was found that for both resins there was a wide range of operational conditions where both high yield and high product purity could be achieved. Not unexpectedly, as 100% step yield was approached, product purity decreased, although under all conditions the purity was greater than 98%.

Figure 8A:
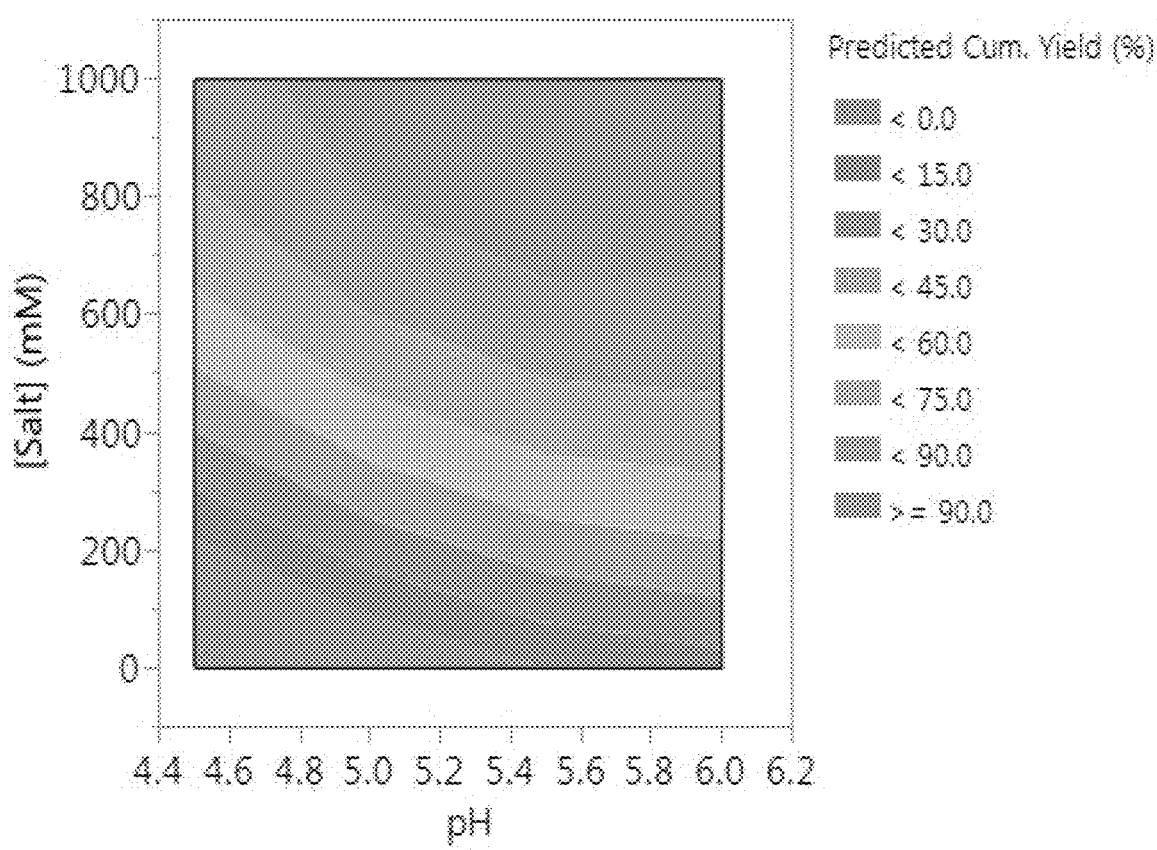
FIG. 8A shows contour plots representing the effect of pH and salt level on percent yield for Fractogel® SO$_3^-$ resin.
Figure 8B:
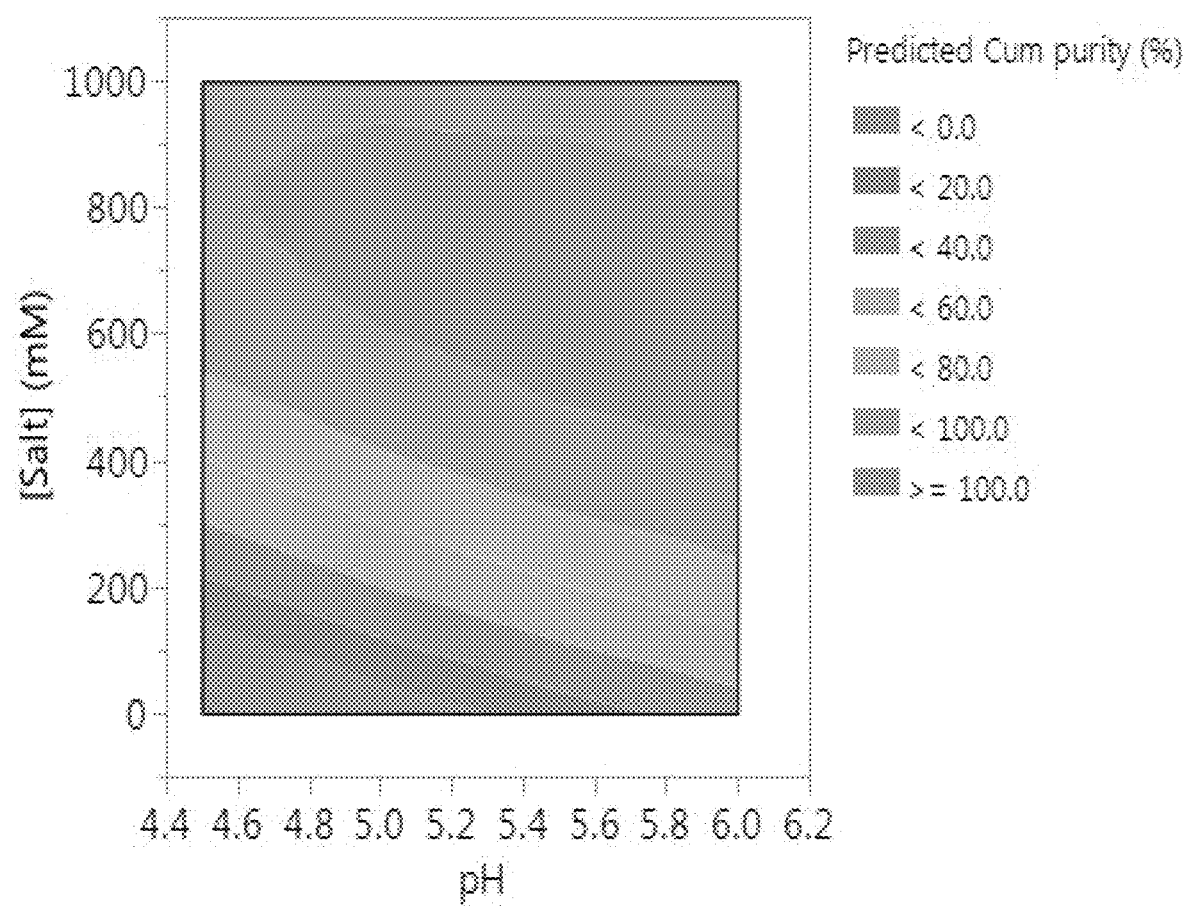
FIG. 8B shows contour plots representing the effect of pH and salt level on percent purity by SEC for Fractogel® SO$_3^-$ resin.
Figure 8C:
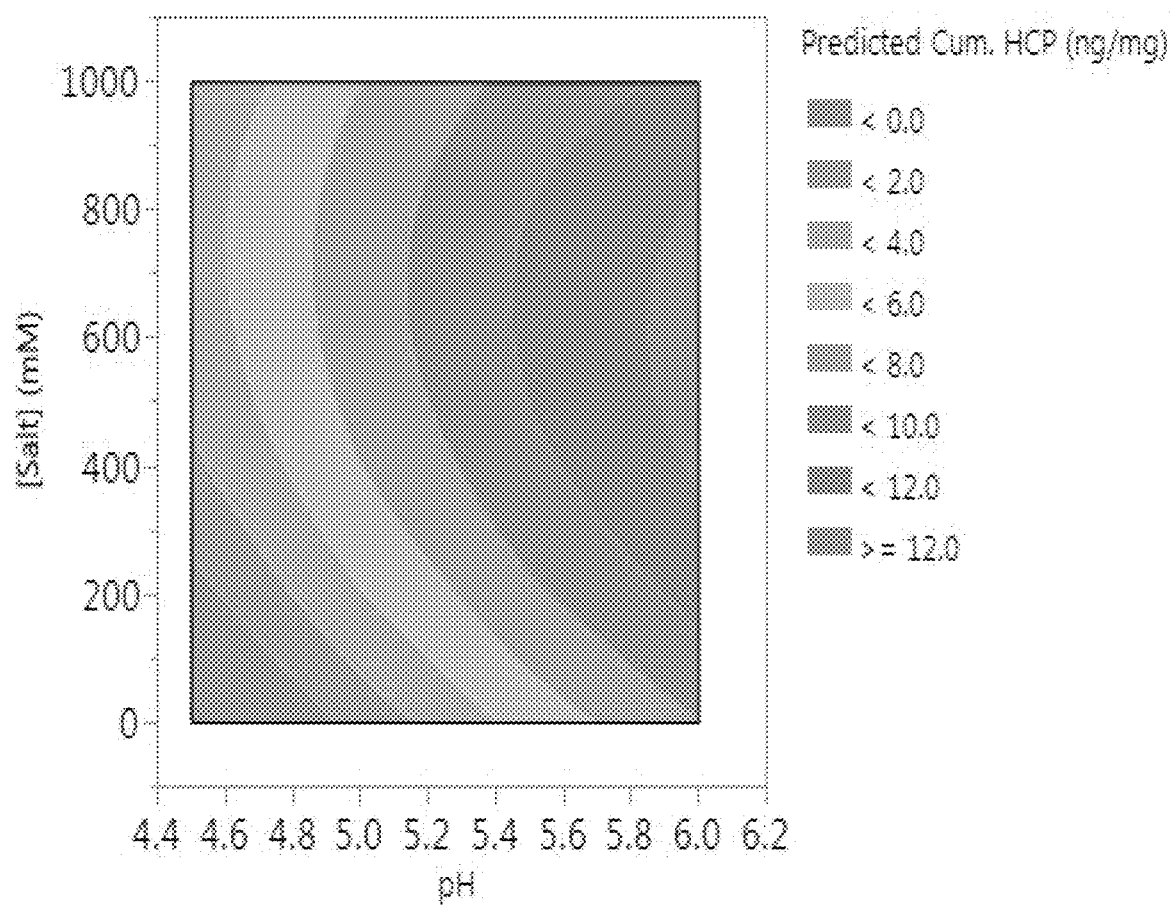
FIG. 8C shows contour plots representing the effect of pH and salt level on galectin-3 concentration (ng/mg) for Fractogel® SO$_3^-$ resin.
Figure 9A:
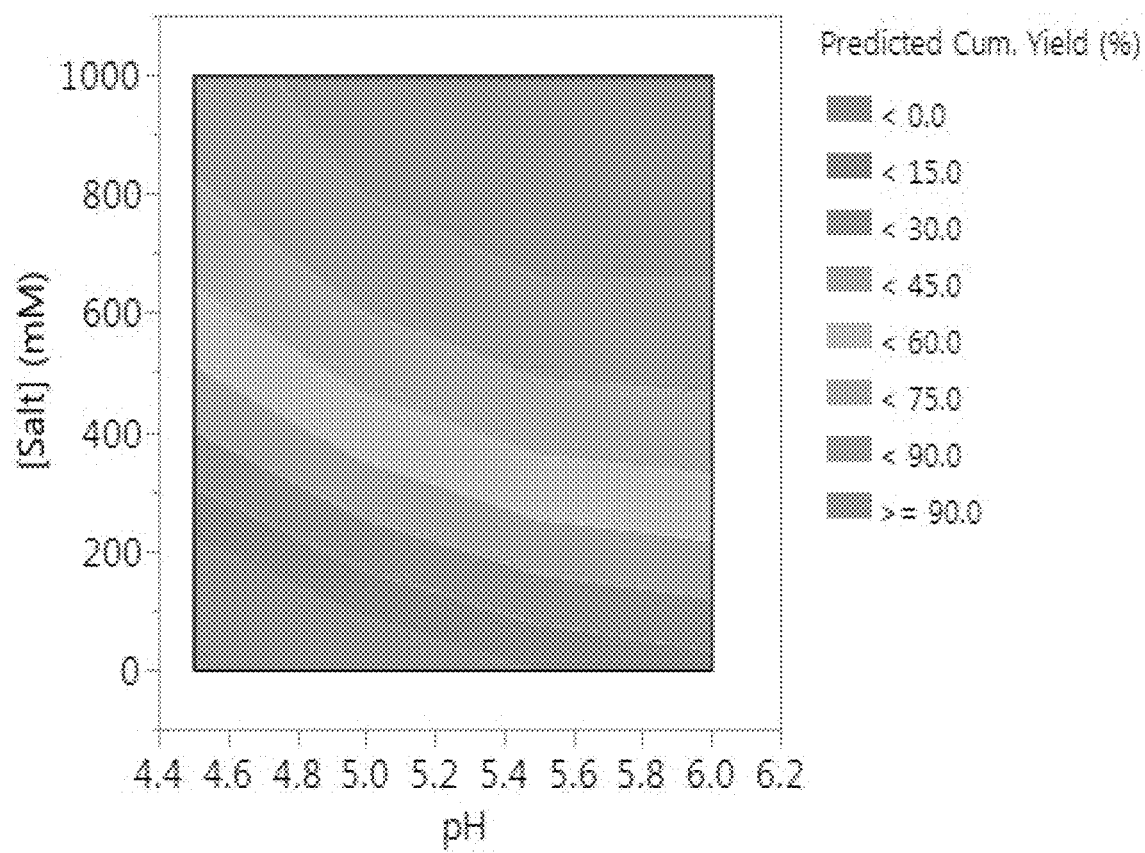
FIG. 9A shows contour plots representing the effect of pH and salt level on percent yield for Fractogel® COO$^-$ resin.
Figure 9B:
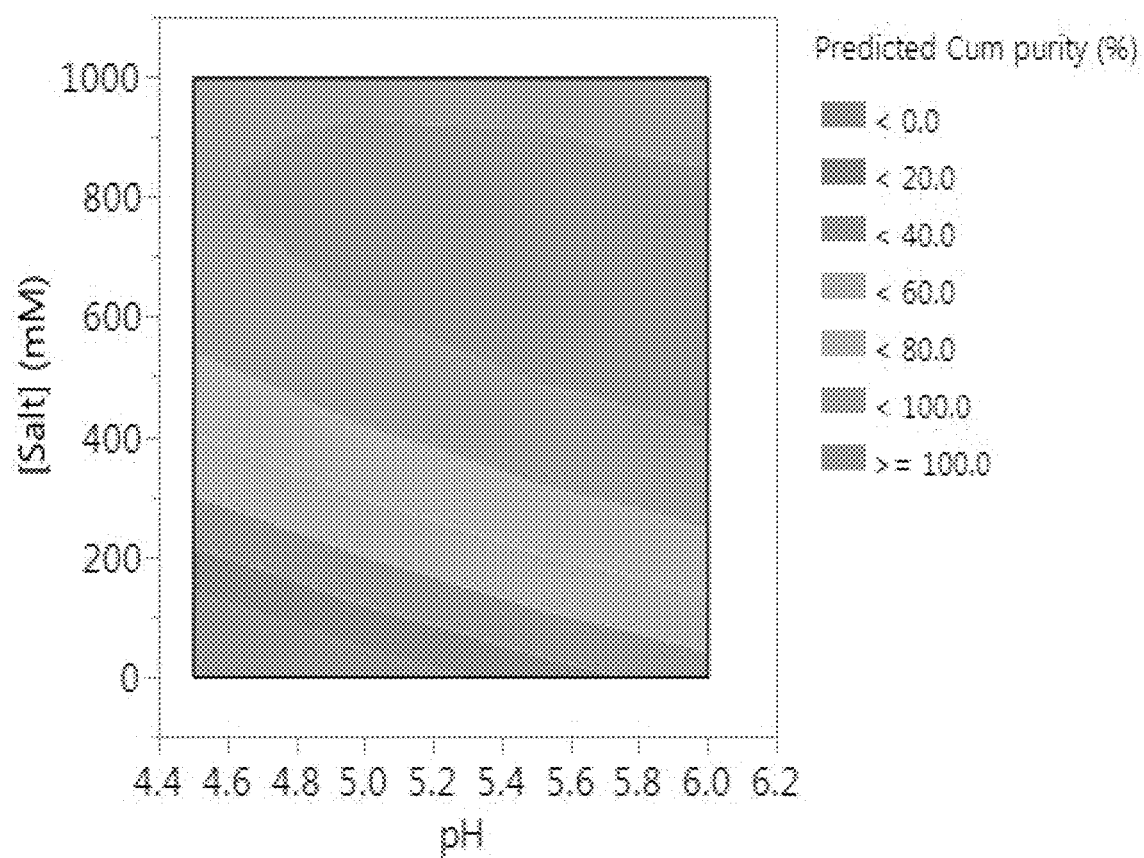
FIG. 9B shows contour plots representing the effect of pH and salt level on percent purity by SEC for Fractogel® COO$^-$ resin.
Figure 9C:
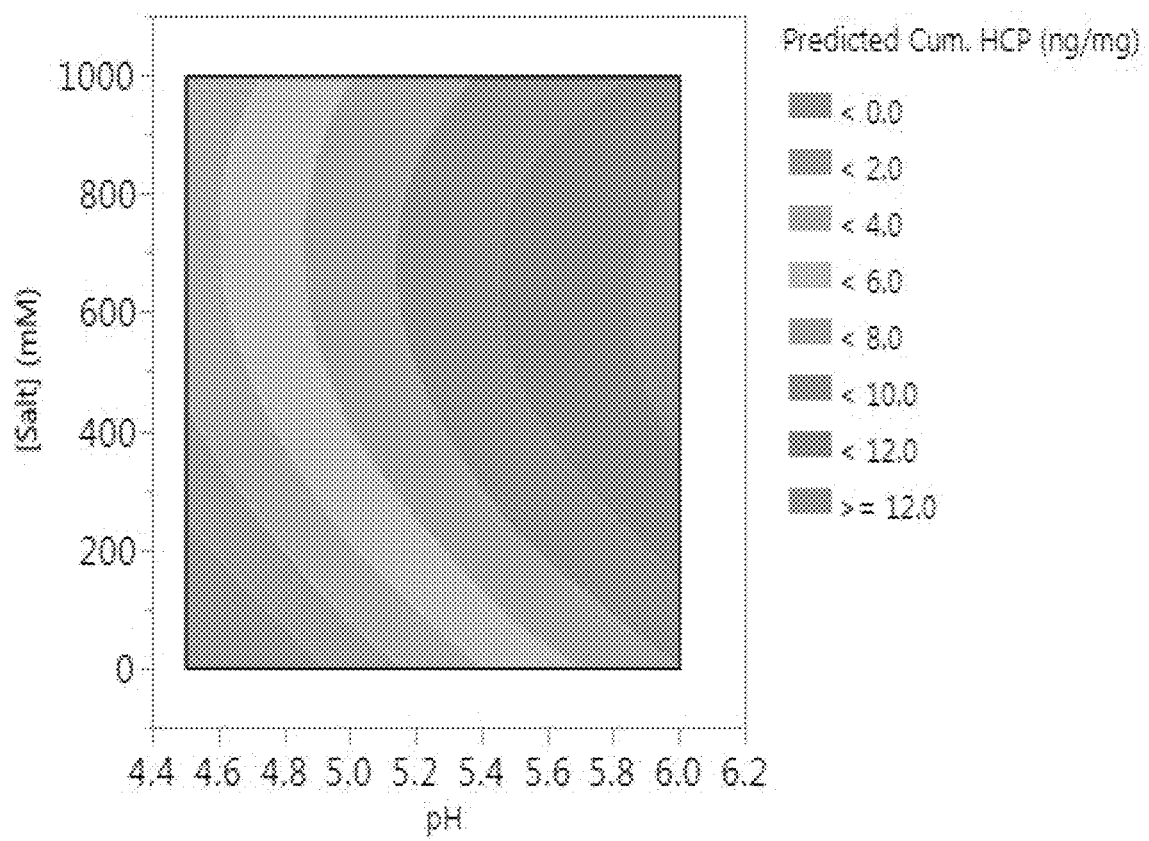
FIG. 9C shows contour plots representing the effect of pH and salt level on galectin-3 concentration (ng/mg) for Fractogel® COO$^-$ resin.

Regression analysis was also performed for step yield, galectin-3 removal, and CEX pool HMW content using a statistical software package (JMP, SAS, version 12.1.0, 2015) to generate predictive models for defining process set points. Contour plots for yield, galectin-3 concentration, and purity by SEC are shown in FIG. 8A-C for Fractogel® $SO_3^-$ and FIG. 9A-C for Fractogel® $COO^-$. The HMW and galectin-3 concentration in the load sample was 1.2% and 13.8 ng/mg, respectively.

Not unexpectedly, when the pH or the elution NaCl strength increased, the step yield increased for both the strong and weak cation exchanger. Additionally, the purity by SEC was high across the range of conditions tested. For both resins tested, galectin-3 removal was improved by lowering pH. For Fractogel® $COO^-$, the best removal of galectin-3 was at pH 4.5, however the operating window was small with marginal removal at ≥pH 5.0. Fractogel® $SO_3^-$ had a larger operating window for galectin-3 removal with clearance observed from pH 4.5-5.5. The optimal operating pH for Fractogel® $SO_3^-$ appeared to be around pH 5.0 to maximize galectin-3 removal, while avoiding operating the CEX at low pH.

Figure 10:
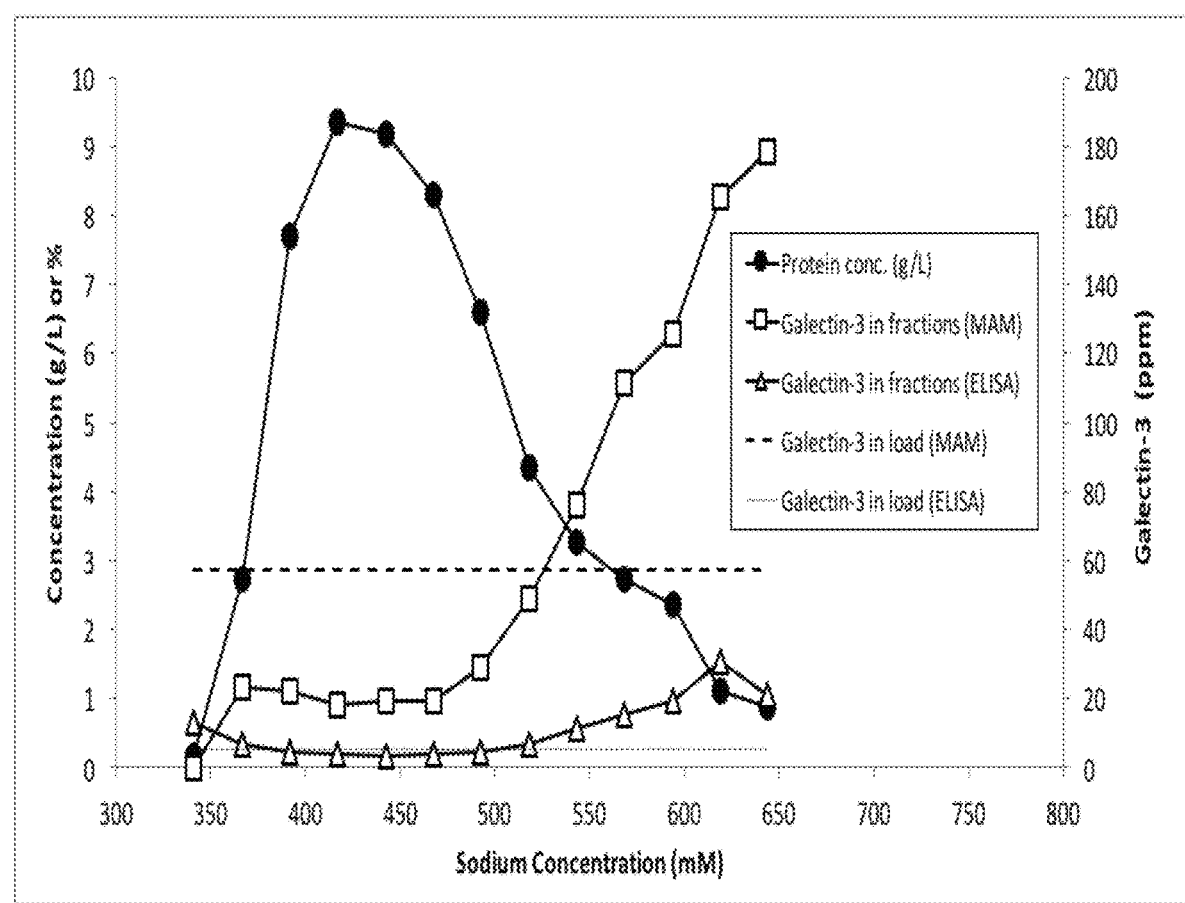
FIG. 10 shows a comparison of galectin-3 levels in individual Fractogel® SO$_3^-$ elution gradient fractions. Circles represent protein concentration of each fraction (g/L), squares represent galectin-3 levels (ppm) of each fraction by the multi-attribute mass spectrometry method (MAM), triangles represent galectin-3 levels (ppm) of each fraction determined by ELISA. Levels of galectin-3 (ppm) in the load are shown as small dashes (measured by ELISA) and larger dashes (measured by MAM).
Figure 11A:
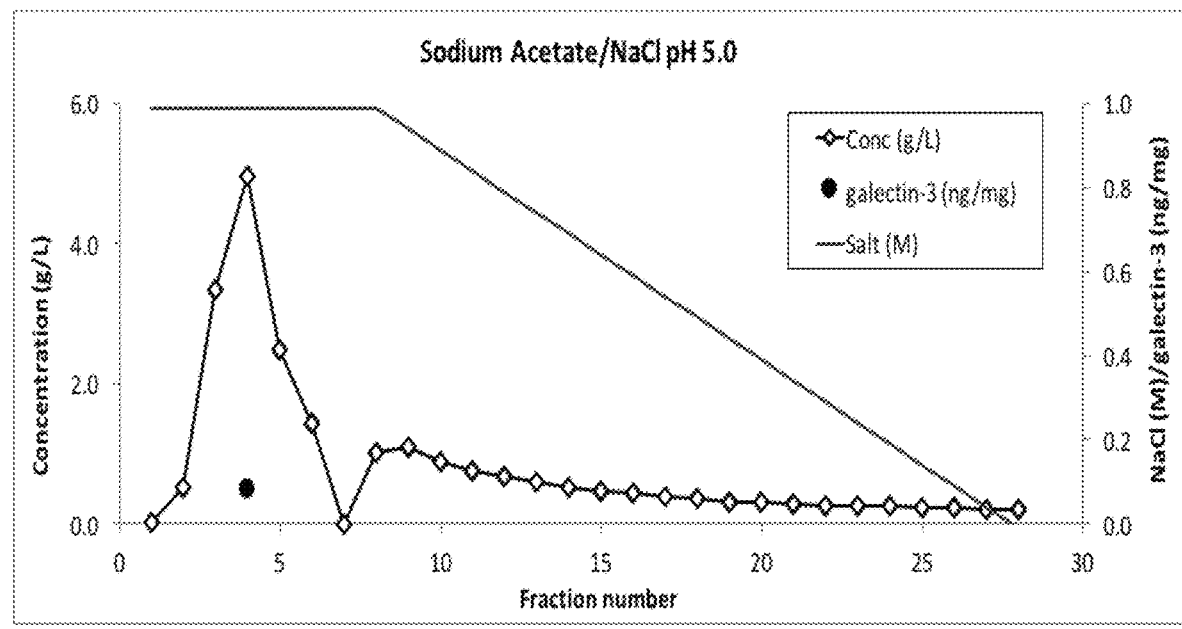
FIG. 11A shows a pseudo-chromatogram, salt concentration and galectin-3 concentration in individual fractions from a Phenyl Sepharose® Fast Flow High Sub in Robo-Column® run with sodium acetate and NaCl at pH 5.0. Diamonds represent product concentration (g/L), solid line represents the salt concentration, circles represent galectin-3 concentration (ng/mL).
Figure 11B:
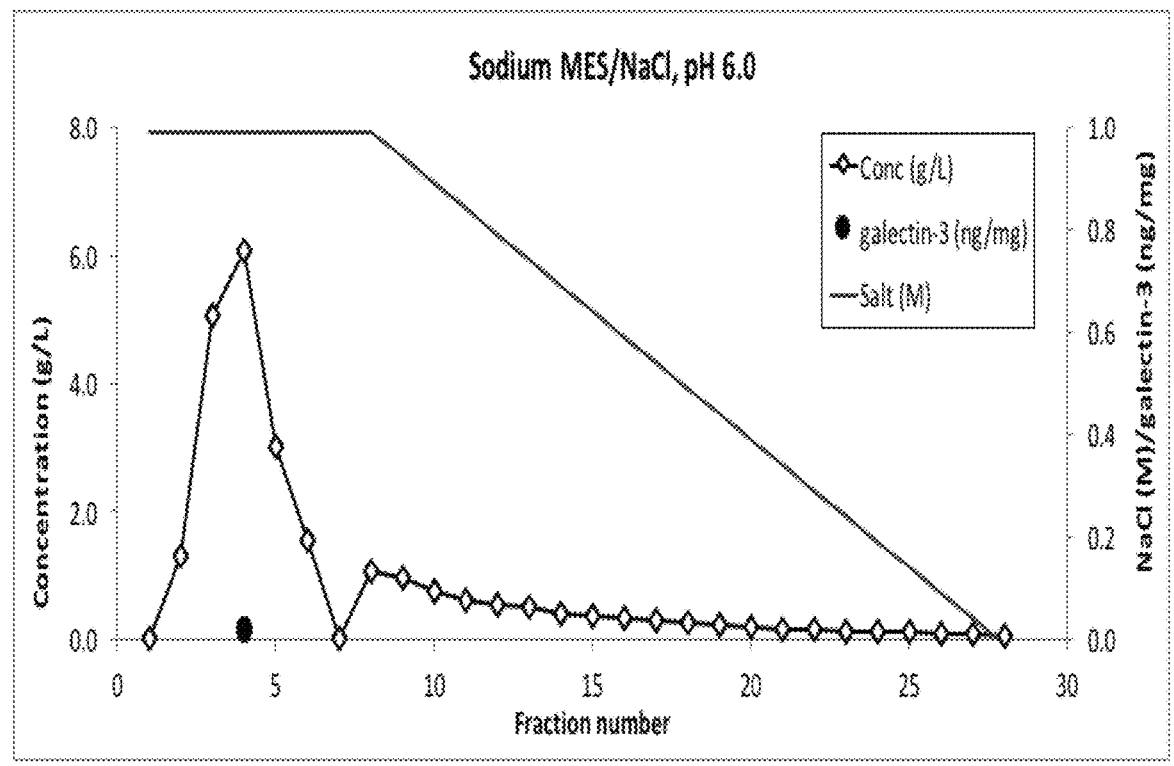
FIG. 11B shows a pseudo-chromatogram, salt concentration and galectin-3 concentration in individual fractions from a Phenyl Sepharose® Fast Flow High Sub in Robo-Column® run with sodium MES and NaCl at pH 6.0. Diamonds represent product concentration (g/L), solid line represents the salt concentration, circles represent galectin-3 concentration (ng/mL).
Figure 11C:
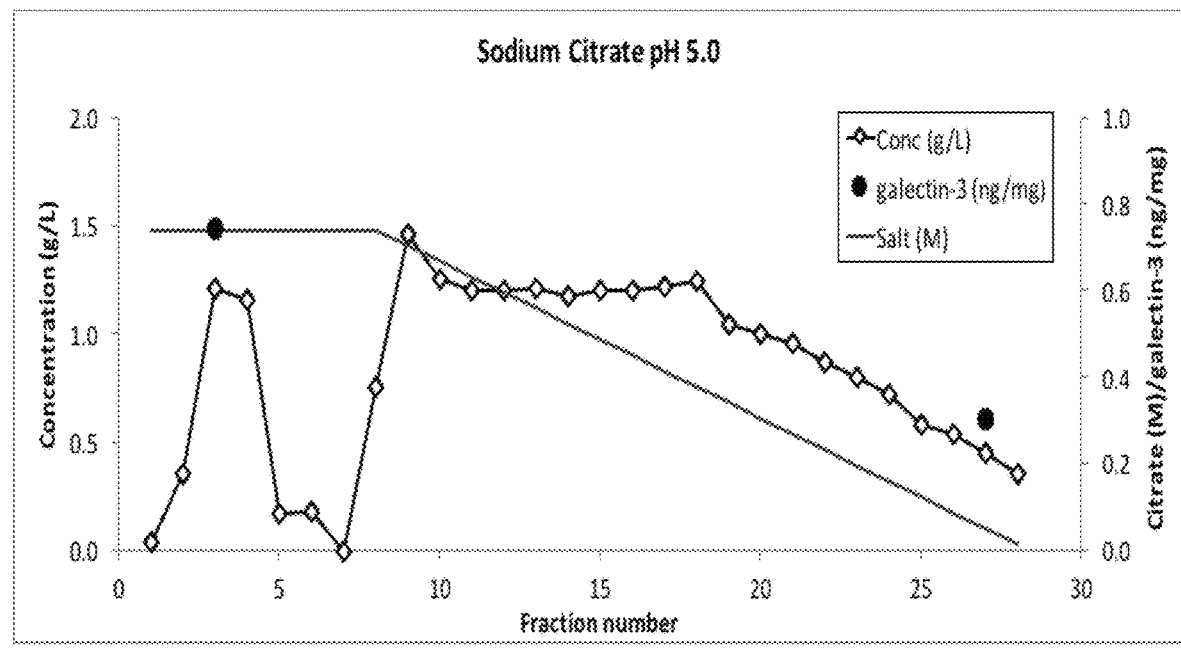
FIG. 11C shows a pseudo-chromatogram, salt concentration and galectin-3 concentration in individual fractions from a Phenyl Sepharose® Fast Flow High Sub in Robo-Column® run with sodium citrate at pH 5.0. Diamonds represent product concentration (g/L), solid line represents the salt concentration, circles represent galectin-3 concentration (ng/mL).
Figure 11D:
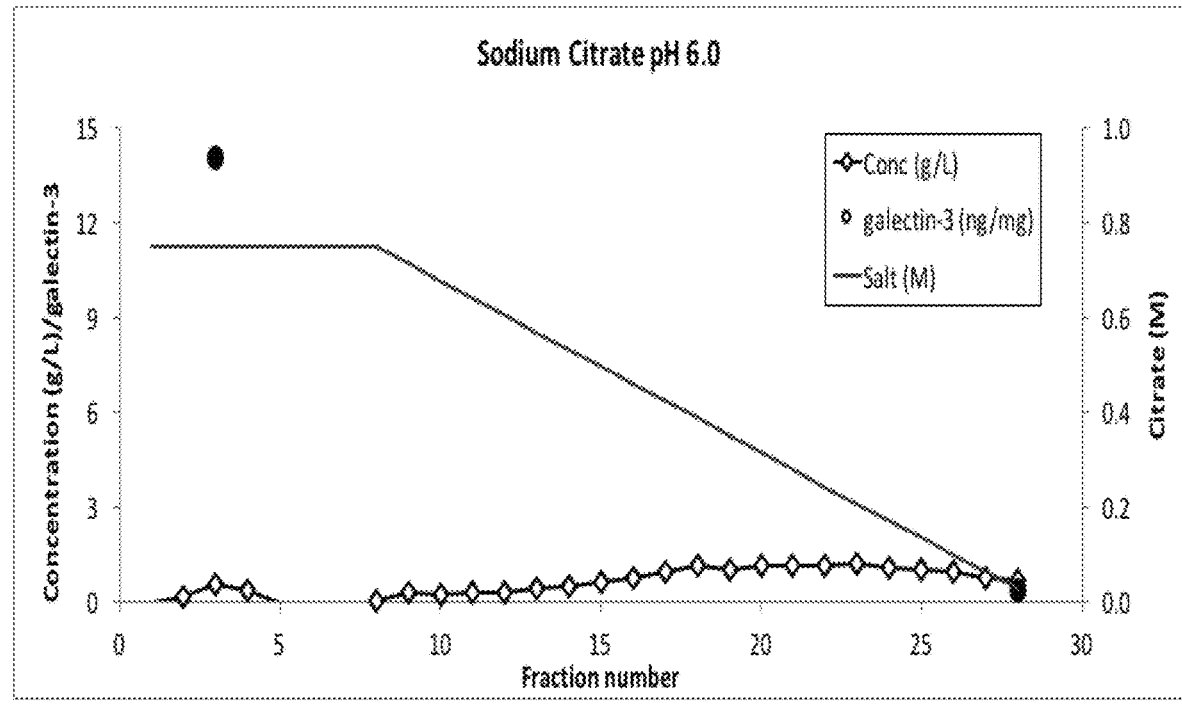
FIG. 11D shows a pseudo-chromatogram, salt concentration and galectin-3 concentration in individual fractions from a Phenyl Sepharose® Fast Flow High Sub in Robo-Column® run with sodium citrate at pH 6.0. Diamonds represent product concentration (g/L), solid line represents the salt concentration, circles represent galectin-3 concentration (ng/mL).
Figure 11E:
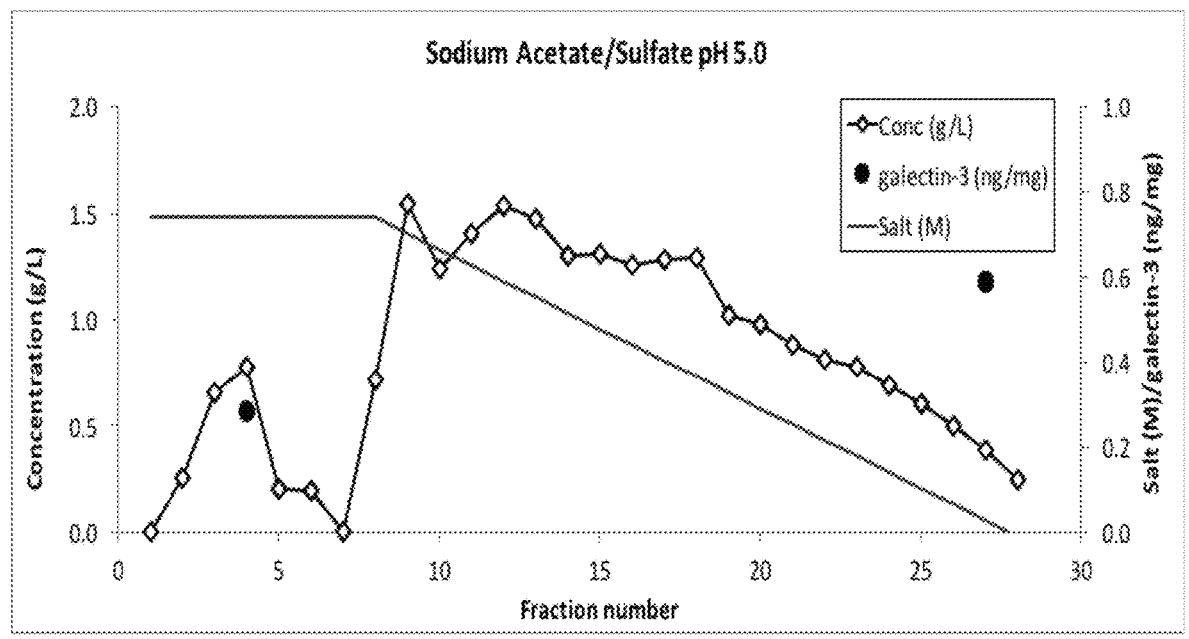
FIG. 11E shows a pseudo-chromatogram, salt concentration and galectin-3 concentration in individual fractions from a Phenyl Sepharose® Fast Flow High Sub in Robo-Column® run with sodium acetate and sodium sulfate at pH 5.0. Diamonds represent product concentration (g/L), solid line represents the salt concentration, circles represent galectin-3 concentration (ng/mL).
Figure 11F:
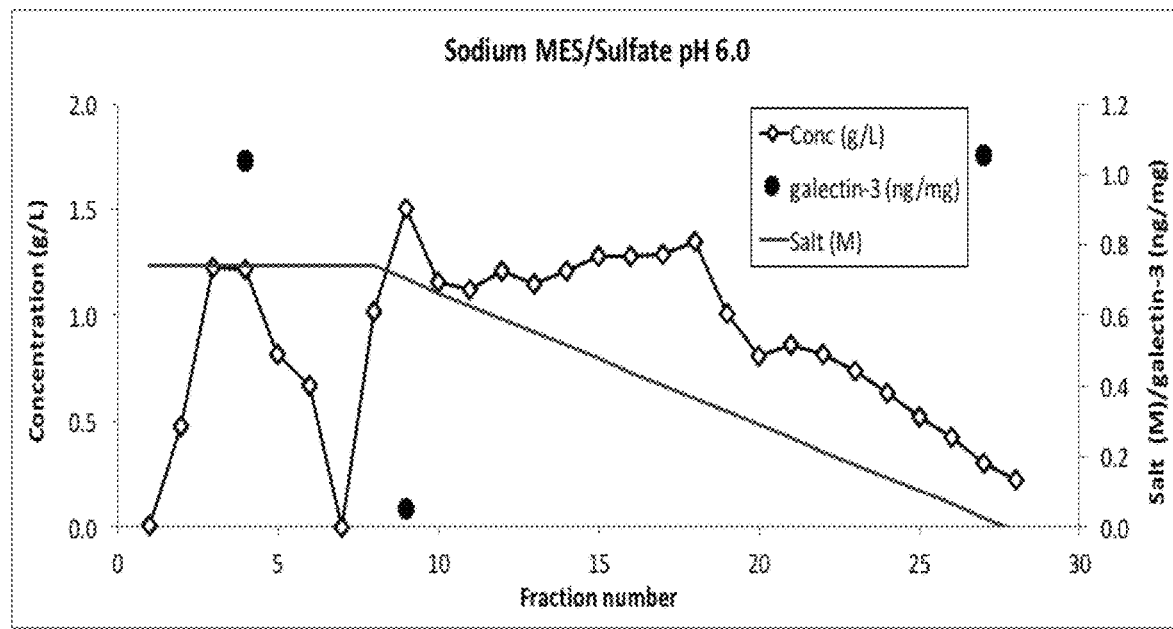
FIG. 11F shows a pseudo-chromatogram, salt concentration and galectin-3 concentration in individual fractions from a Phenyl Sepharose® Fast Flow High Sub in Robo-Column® run with sodium MES and sodium sulfate at pH 6.0. Diamonds represent product concentration (g/L), solid line represents the salt concentration, circles represent galectin-3 concentration (ng/mL).
Figure 11G:
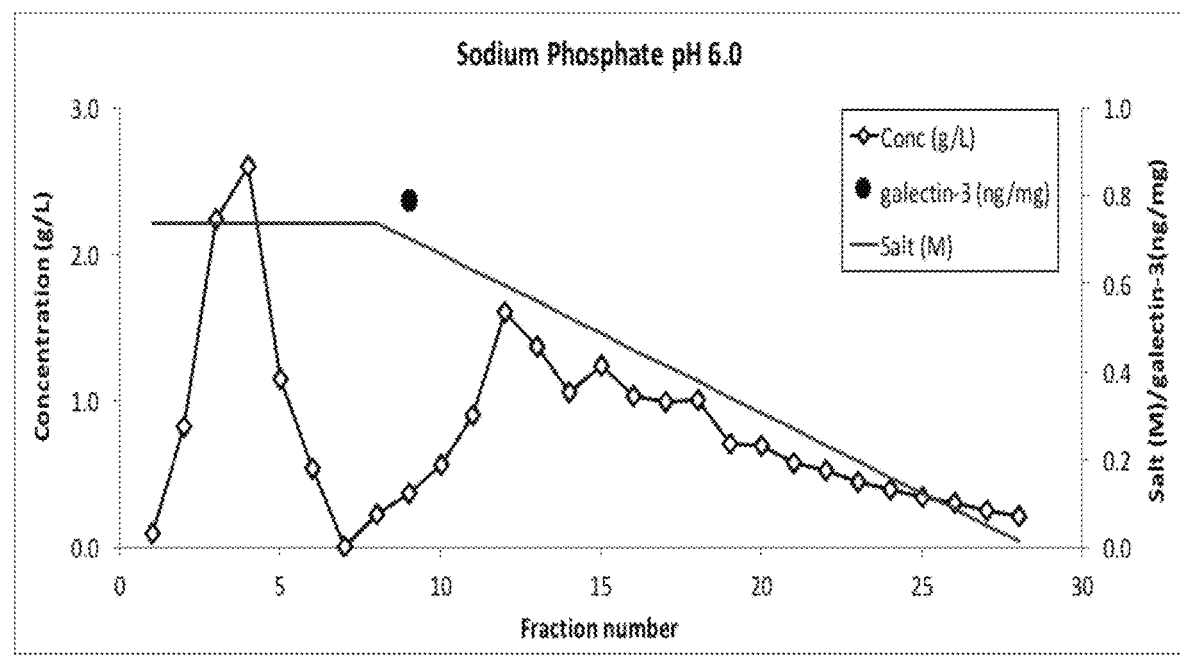
FIG. 11G shows a pseudo-chromatogram, salt concentration and galectin-3 concentration in individual fractions from a Phenyl Sepharose® Fast Flow High Sub in Robo-Column® run with sodium phosphate at pH 6.0. Diamonds represent product concentration (g/L), solid line represents the salt concentration, circles represent galectin-3 concentration (ng/mL).
Figure 11H:
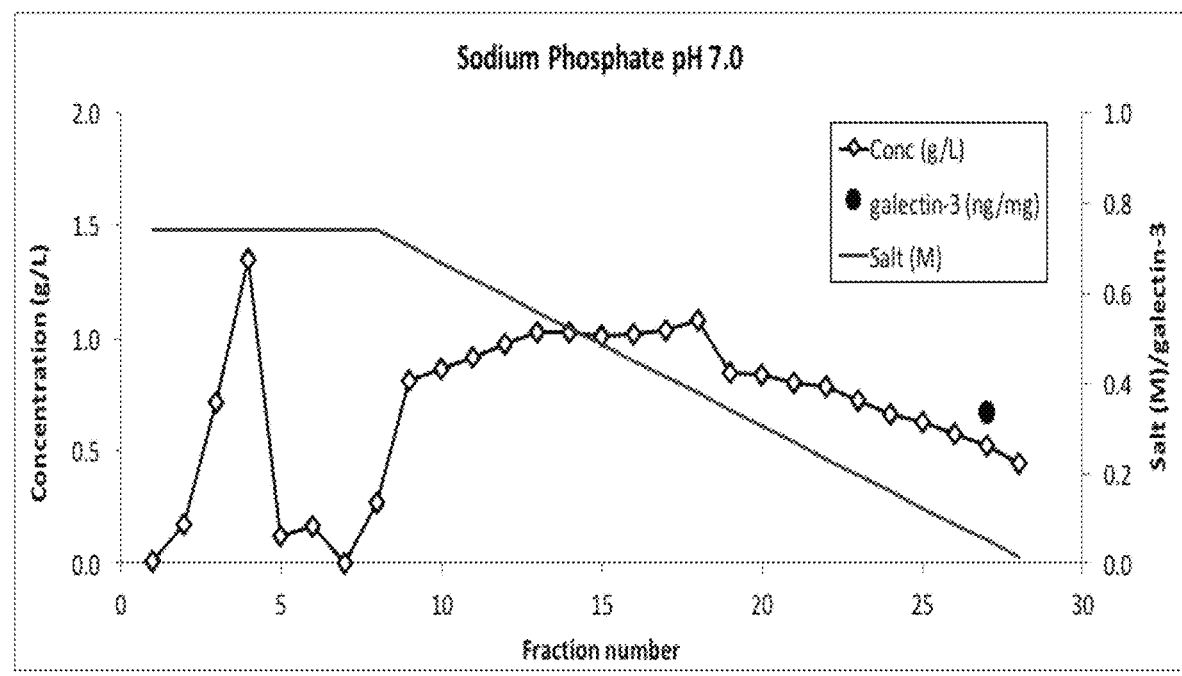
FIG. 11H shows a pseudo-chromatogram, salt concentration and galectin-3 concentration in individual fractions from a Phenyl Sepharose® Fast Flow High Sub in Robo-Column® run with sodium phosphate at pH 7.0. Diamonds represent product concentration (g/L), solid line represents the salt concentration, circles represent galectin-3 concentration (ng/mL).
Figure 12A:
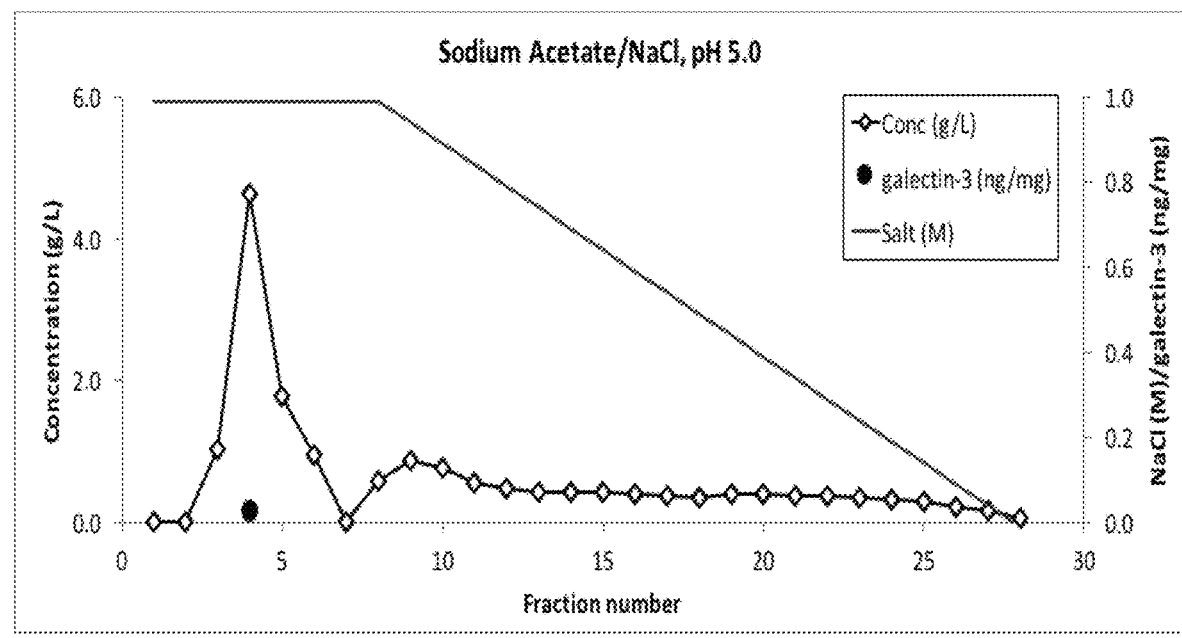
FIG. 12A shows a pseudo-chromatogram, salt concentration and galectin-3 concentration in individual fractions from a Toyopearl® Butyl 650M in RoboColumn® run with sodium acetate and NaCl at pH 5.0. Diamonds represent product concentration (g/L), solid line represents the salt concentration, circles represent galectin-3 concentration (ng/mL).
Figure 12B:
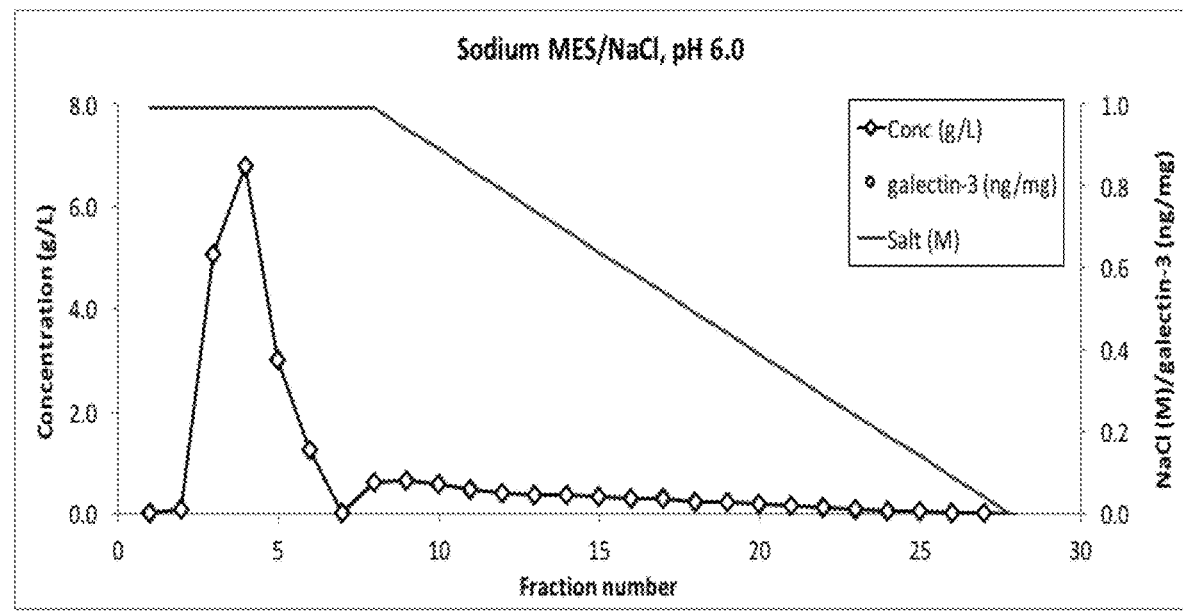
FIG. 12B shows a pseudo-chromatogram, salt concentration and galectin-3 concentration in individual fractions from a Toyopearl® Butyl 650M in RoboColumn® run with sodium MES and NaCl at pH 6.0. Diamonds represent product concentration (g/L), solid line represents the salt concentration, circles represent galectin-3 concentration (ng/mL).
Figure 12C:
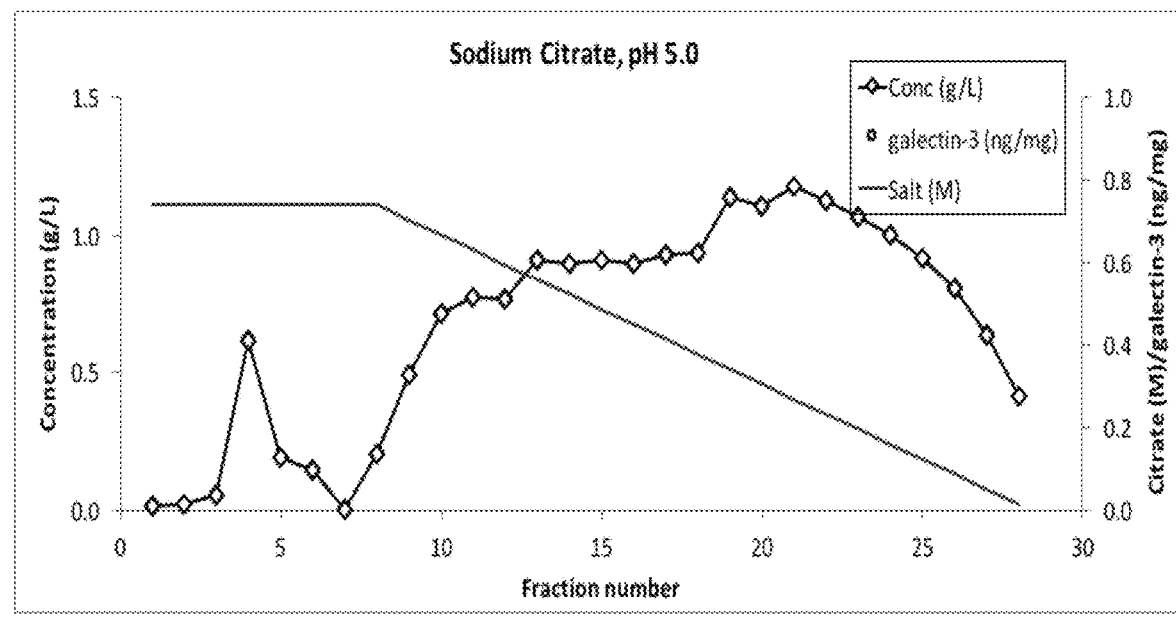
FIG. 12C shows a pseudo-chromatogram, salt concentration and galectin-3 concentration in individual fractions from a Toyopearl® Butyl 650M in RoboColumn® run with sodium citrate at pH 5.0. Diamonds represent product concentration (g/L), solid line represents the salt concentration, circles represent galectin-3 concentration (ng/mL).
Figure 12D:
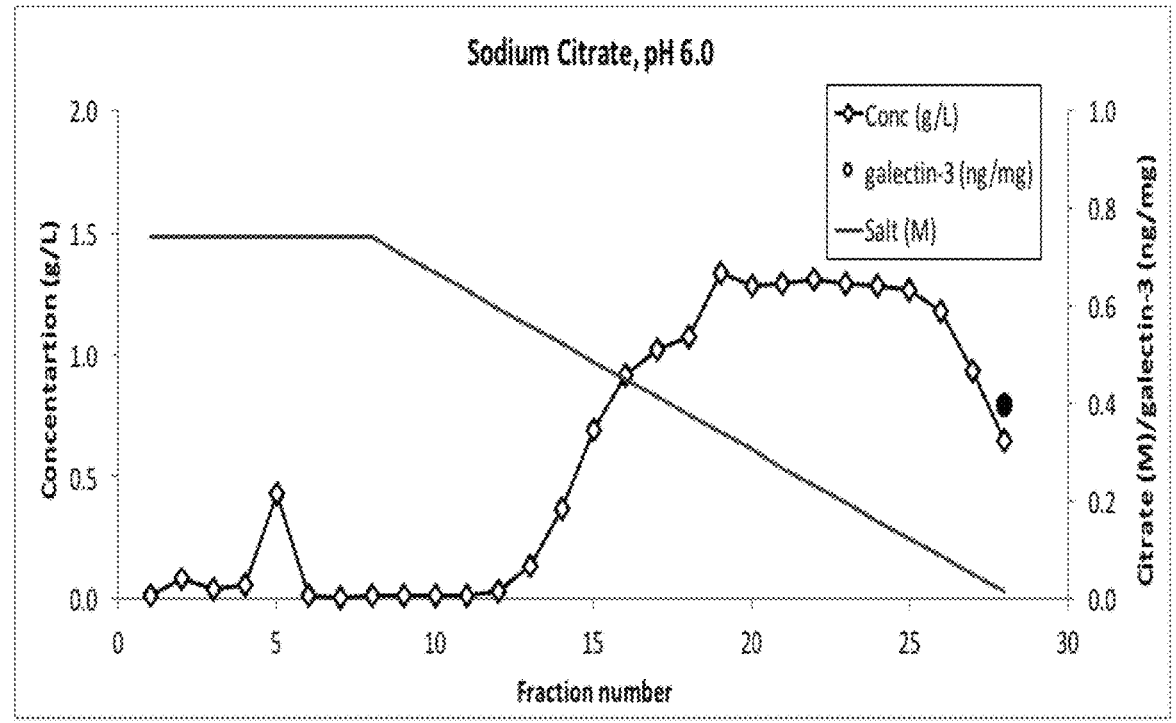
FIG. 12D shows a pseudo-chromatogram, salt concentration and galectin-3 concentration in individual fractions from a Toyopearl® Butyl 650M in RoboColumn® run with sodium citrate at pH 6.0. Diamonds represent product concentration (g/L), solid line represents the salt concentration, circles represent galectin-3 concentration (ng/mL).
Figure 12E:
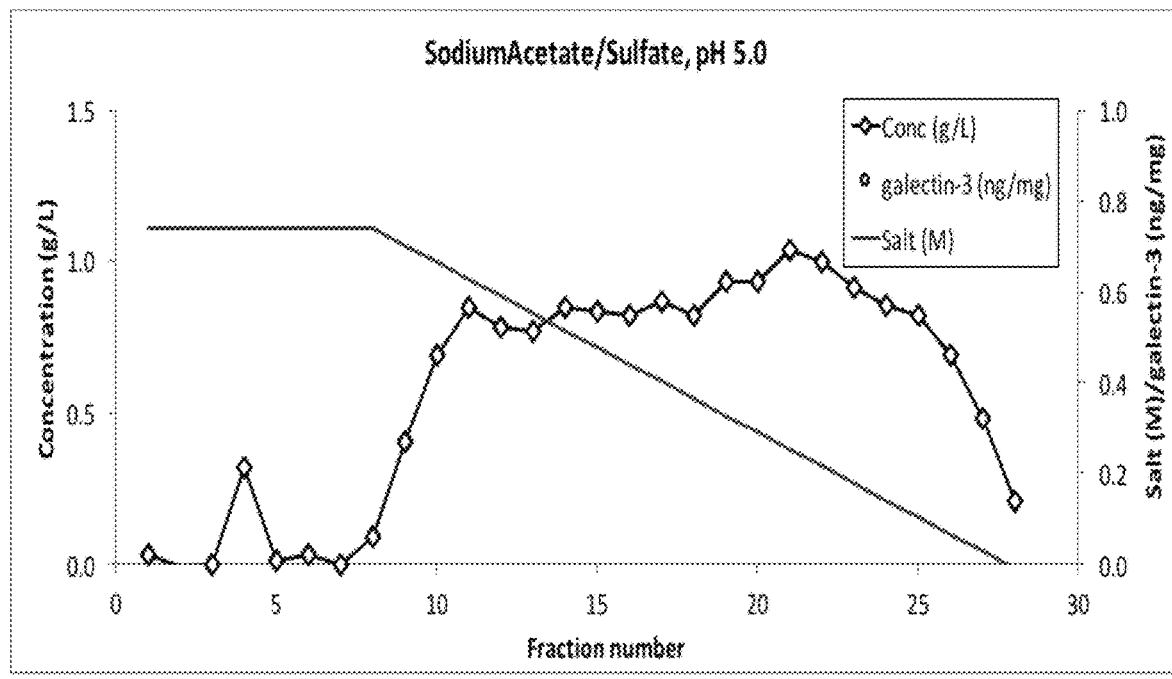
FIG. 12E shows a pseudo-chromatogram, salt concentration and galectin-3 concentration in individual fractions from a Toyopearl® Butyl 650M in RoboColumn® run with sodium acetate and sodium sulfate at pH 5.0. Diamonds represent product concentration (g/L), solid line represents the salt concentration, circles represent galectin-3 concentration (ng/mL).
Figure 12F:
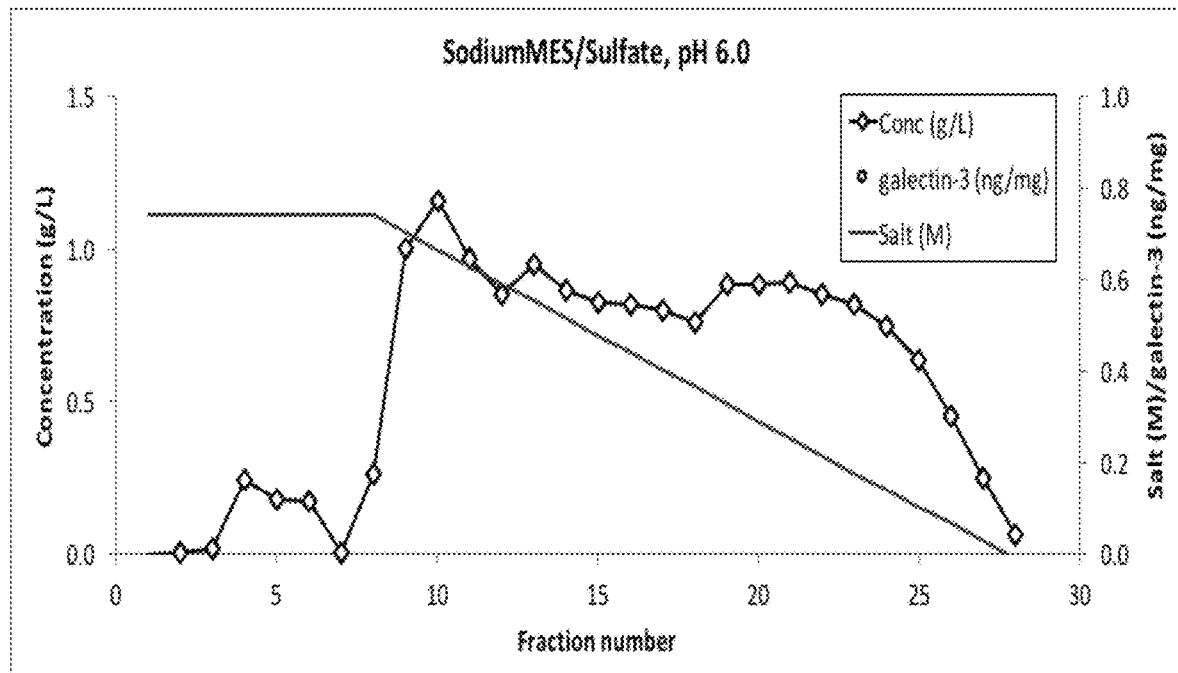
FIG. 12F shows a pseudo-chromatogram, salt concentration and galectin-3 concentration in individual fractions from a Toyopearl® Butyl 650M in RoboColumn® run with sodium MES and sodium sulfate at pH 6.0. Diamonds represent product concentration (g/L), solid line represents the salt concentration, circles represent galectin-3 concentration (ng/mL).
Figure 12G:
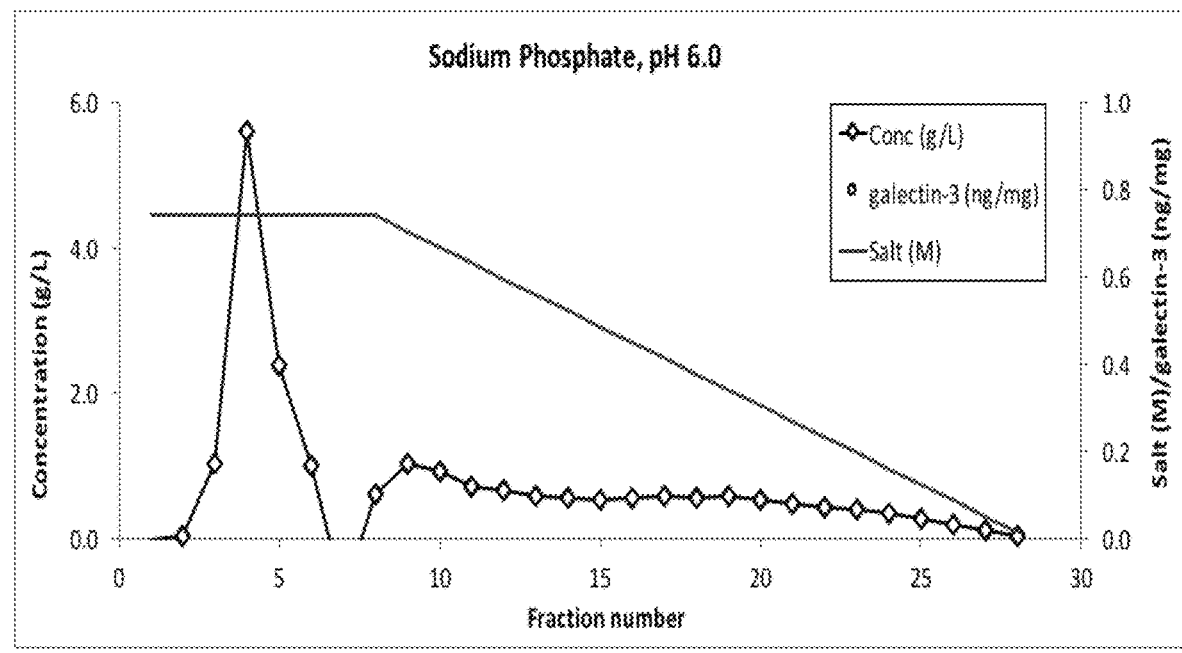
FIG. 12G shows a pseudo-chromatogram, salt concentration and galectin-3 concentration in individual fractions from a Toyopearl® Butyl 650M in RoboColumn® run with sodium phosphate at pH 6.0. Diamonds represent product concentration (g/L), solid line represents the salt concentration, circles represent galectin-3 concentration (ng/mL).
Figure 12H:
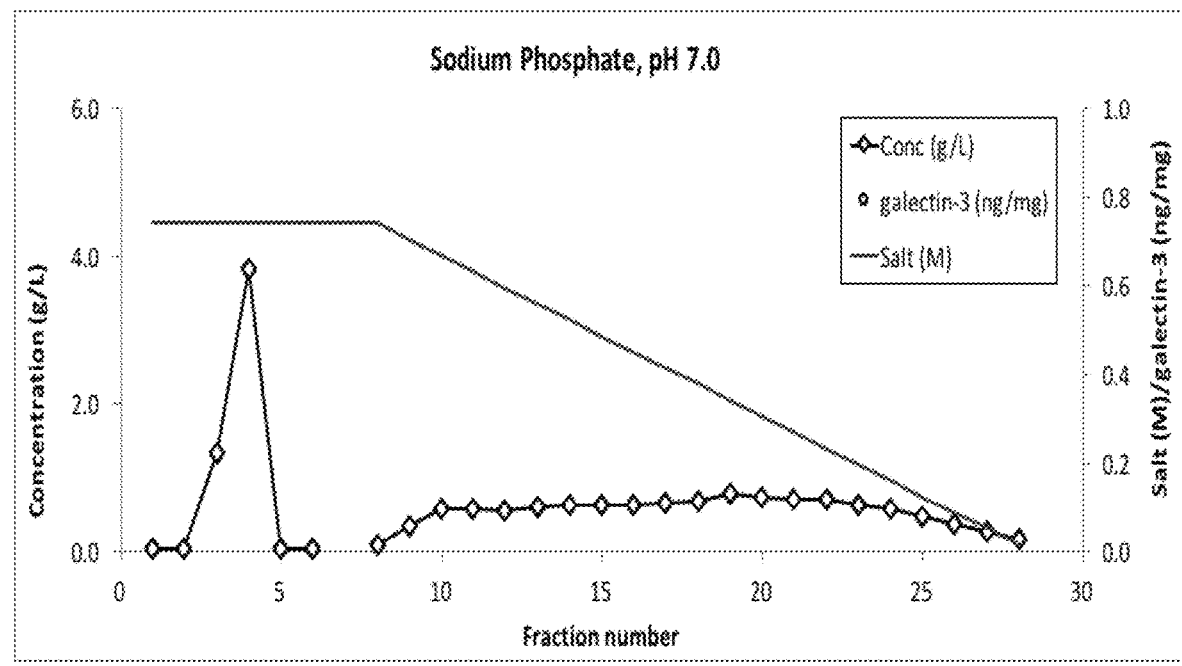
FIG. 12H shows a pseudo-chromatogram, salt concentration and galectin-3 concentration in individual fractions from a Toyopearl® Butyl 650M in RoboColumn® run with sodium phosphate at pH 7.0. Diamonds represent product concentration (g/L), solid line represents the salt concentration, circles represent galectin-3 concentration (ng/mL).

The galectin-3 removal results of the CEX Robocolumn® screen were confirmed at bench scale using a Fractogel® $SO_3^-$ column operated at pH 5.0. The CEX method for the bench scale column was similar to the RoboColumns®, and employed a 20CV elution gradient from 0 to 1 M NaCl in sodium acetate buffer at pH 5.0. The results of the gradient elution are shown in FIG. 10. The load material contained 57.5 ng/mg of galectin-3 by the mass spectrometry multi-attribute method ("MAM"; Rogers et al., *Development of a quantitative mass spectrometry multi-attribute method for characterization, quality control testing and disposition of biologics*, mAbs 7(5): 881-890 (2015), and 5.6 mg/mg by galectin-3 ELISA. The tail end of the elution peak, when the gradient was above approximately 500 mM sodium, was enriched in galectin-3, while the main portion of the peak showed some galectin-3 removal. The level of galectin-3 in the CEX pool can be further controlled by increasing the percentage of the peak that is collected at the end of the elution.

and NaCl or sodium sulfate at pH 6.0, sodium citrate at pH 5.0 and 6.0, and sodium phosphate at pH 6.0 and 7.0. The load material of Protein A-purified aflibercept contained 18 ng/mg galectin-3 by ELISA and was loaded to 25 g/L resin. Bound product was eluted using a salt gradient from high to low salt. Fractions of the flow-through, wash, and the elution gradient peak were analyzed by galectin-3 ELISA. The results are shown in the FIG. 11A-H and FIG. 12A-H. The product did not bind tightly to either of the HIC resins at any of the conditions tested. However, both resins removed some level of galectin-3. Butyl 650M had the most robust clearance of galectin-3, as very few fractions contained detectable galectin-3.

A second RoboColumn® screen was performed to determine optimal pH and salt operating ranges for Butyl 650M, which had the most robust galectin-3 removal. This experiment was performed in product flow-through mode, since the galectin-3 appeared to bind to the resin more strongly than the product. Two different levels of NaCl were evaluated at four different pHs. For pH 5.0 and 5.5, sodium acetate was used as the buffer. For pH 6.0 and 6.5, sodium MES was used as the buffer. The load material was conditioned to have the same pH and salt level as the washes and the columns were loaded up to 100 g/L resin. Fractions of the flow-through were collected and mini-pools representing increasing load levels were analyzed for galectin-3. Additionally, the post-load wash was collected and analyzed in two fractions, with the early fraction containing most of the product washout and the late fraction containing the tailing portion of the washout. The results are shown in Table 4, below. The results indicate that higher salt levels and lower pH's are best for galectin-3 removal by Butyl 650M resin, with complete clearance shown at pH 5.0. Galectin-3 breakthrough does begin to increase with higher loading levels, but the galectin removal is still significant at 100 g/L resin loadings and most or all of the galectin appears to remain bound to the column during the post-load wash.

TABLE 4

Galectin-3 levels determined by specific ELISA of fractions from a RoboColumn® flow-through screen using Butyl 650M resin.

| Flow-through condition | Galectin-3 (ng/mg) | | | | | |
|---|---|---|---|---|---|---|
| | Load | 33 g/Lr | 66 g/Lr | 100 g/Lr | Wash1 | Wash2 |
| 500 mM NaCl, pH 6.5 | 19.5 | <LOQ | 0.04 | 0.10 | 0.39 | 0.36 |
| 250 mM NaCl, pH 6.5 | 18.8 | 0.05 | 0.25 | 0.56 | 0.56 | 2.11 |
| 500 mM NaCl, pH 6.0 | 19.2 | <LOQ | 0.01 | 0.03 | 0.1 | <LOQ |
| 250 mM NaCl, pH 6.0 | 19.6 | <LOQ | 0.03 | 0.08 | 0.31 | 0.2 |
| 500 mM NaCl, pH 5.5 | 17.8 | <LOQ | <LOQ | 0.01 | <LOQ | <LOQ |
| 250 mM NaCl, pH 5.5 | 18.3 | <LOQ | <LOQ | 0.01 | <LOQ | <LOQ |
| 500 mM NaCl, pH 5.0 | 18.3 | <LOQ | <LOQ | <LOQ | <LOQ | <LOQ |
| 250 mM NaCl, pH 5.0 | 20.4 | <LOQ | <LOQ | <LOQ | <LOQ | <LOQ |

LOQ = limit of quantitation of the assay.

HIC Chromatography Screening.

HTS screening with RoboColumns® was used to evaluate two HIC resins for galectin-3 removal: Phenyl Sepharose® Hi-Sub and Toyopearl® Butyl 650M. These resins were screened in bind and elute mode with sodium acetate buffer and NaCl or sodium sulfate at pH 5.0, sodium MES buffer The results from the high throughput flow-through screen were confirmed at bench scale Butyl 650M column. The column was loaded with CEX pool conditioned with 400 mM NaCl at pH 5.0. Fractions of the flow-through, collected up to 125 g/L resin, and the post load wash were analyzed by galectin-3 ELISA (see, Table 5, below).

TABLE 5

Galectin-3 Levels by ELISA of fractions from a bench scale flowthrough run using Butyl 650M resin.

| Flow-through Condition | Load | Galectin-3 (ng/mg) | | | | | |
| --- | --- | --- | --- | --- | --- | --- | --- |
| | | 30 g/Lr | 60 g/Lr | 90 g/Lr | 125 g/Lr | Wash1 | Wash2 |
| 400 mM NaCl, pH 5.0 | 7.3 | <LOQ | <LOQ | <LOQ | <LOQ | <LOQ | <LOQ |

LOQ = limit of quantitation of the assay.

Example 3: Purification of Recombinant Protein by Removal of Iron Cation

Protein a Chromatography Screening.

Figure 13:
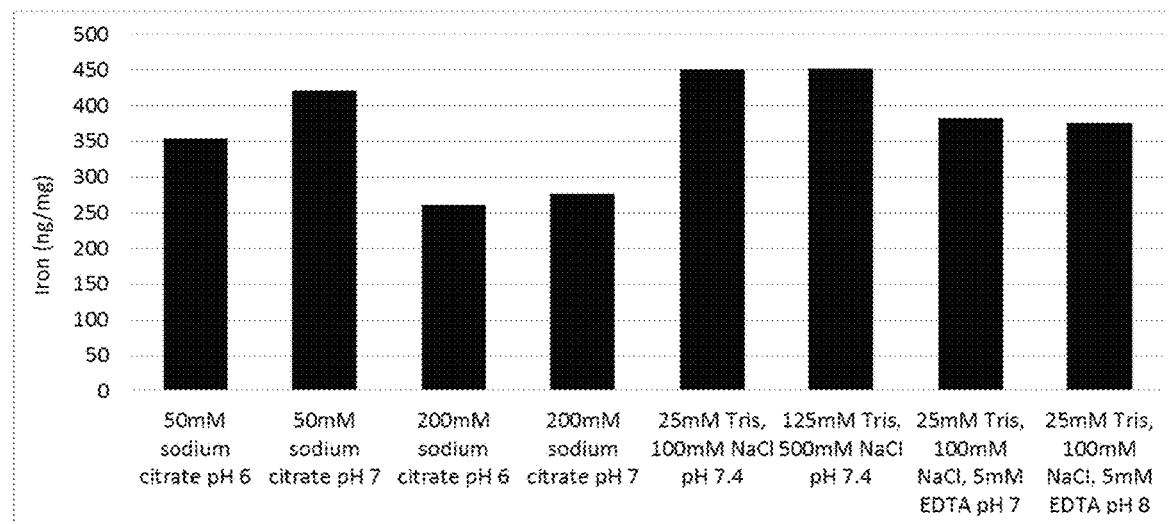
FIG. 13 represents iron levels of Protein A eluant pools from a RoboColumn® screen with different Wash 2 buffers.

A high throughput RoboColumn® screen of Wash 2 condition to remove iron was performed using eight (8) MabSelect SuRe® Protein A-packed columns on a Tecan liquid handler. The columns were equilibrated and loaded similarly with harvested cell culture fluid (HCCF) containing iron, followed by a wash with equilibration buffer (EQ: 25 mM Tris, 100 mM NaCl, pH 7.4.). Each column was then washed with a different secondary wash consisting of known metal chelating compounds such as citrate and EDTA, while EQ was used as a negative control. The secondary washes were followed up by EQ and the product was eluted using a low pH buffer. The elution pools were submitted for iron quantitation by ICP-MS (FIG. 13). All of the elution pools contained a significant amount of iron, with the EQ conditions having the highest level and the 200 mM citrate Wash 2 conditions showing approximately 200 ppm of removal. The EDTA Wash 2 only provided slight removal.

Figure 14:
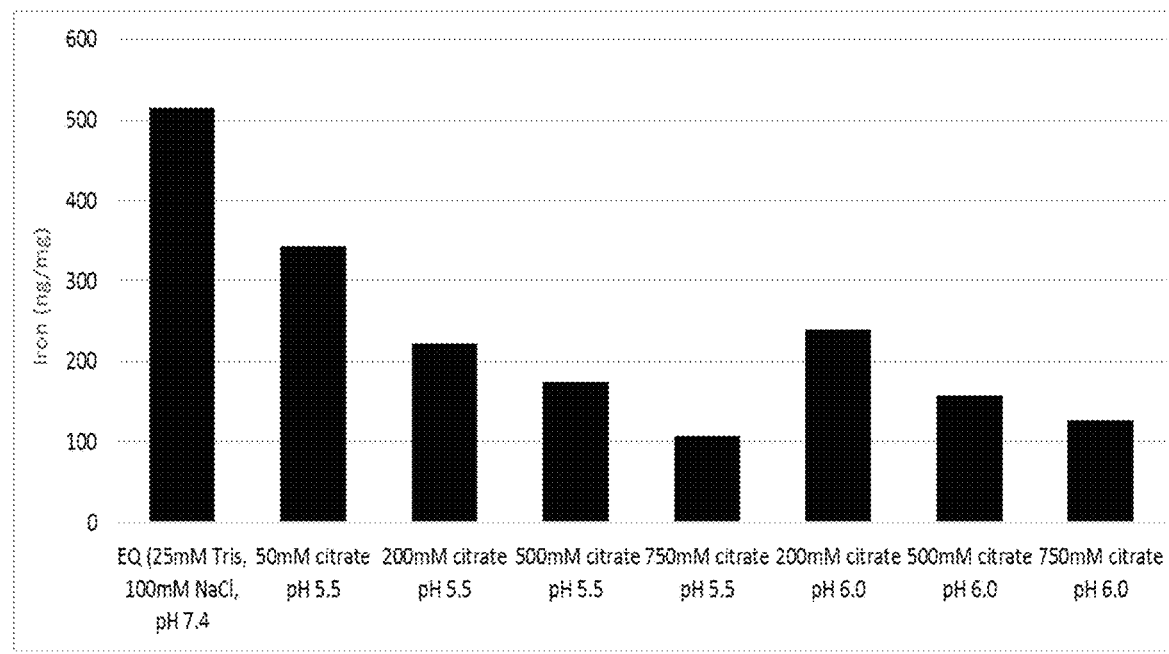
FIG. 14 represents iron levels of Protein A eluant pools from a RoboColumn® screen with Wash 2 buffers containing higher citrate concentrations as shown.

A second RoboColumn® wash screen was performed to determine if higher levels of citrate in the Wash 2 buffer could provide more iron removal. The results are shown in FIG. 14. Increasing the levels of citrate resulted in significantly more iron removal, as determined by ICP-MS. Interestingly, the lower pH condition of pH 5.5 slightly improved iron removal compared to pH 6.0, indicating that lower pH may improve iron chelation by citrate.

Figure 15:
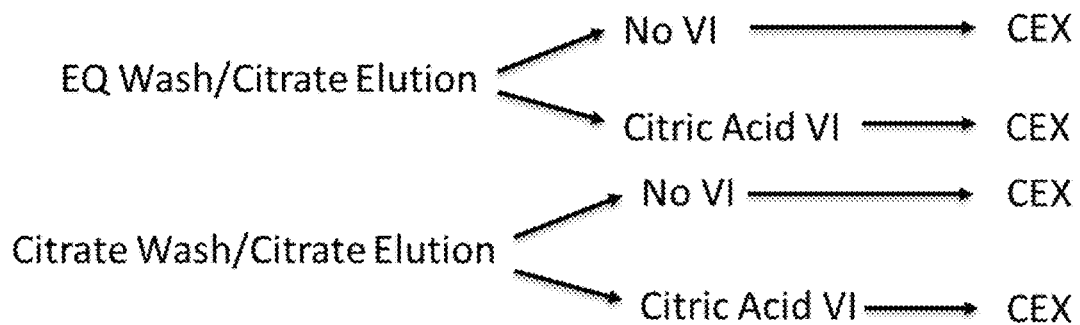
FIG. 15 shows a schematic representation of a Protein A low pH viral inactivation experiment to analyze the effect of citrate on the elution and low pH hold on iron concentration in the product.
Figure 16:
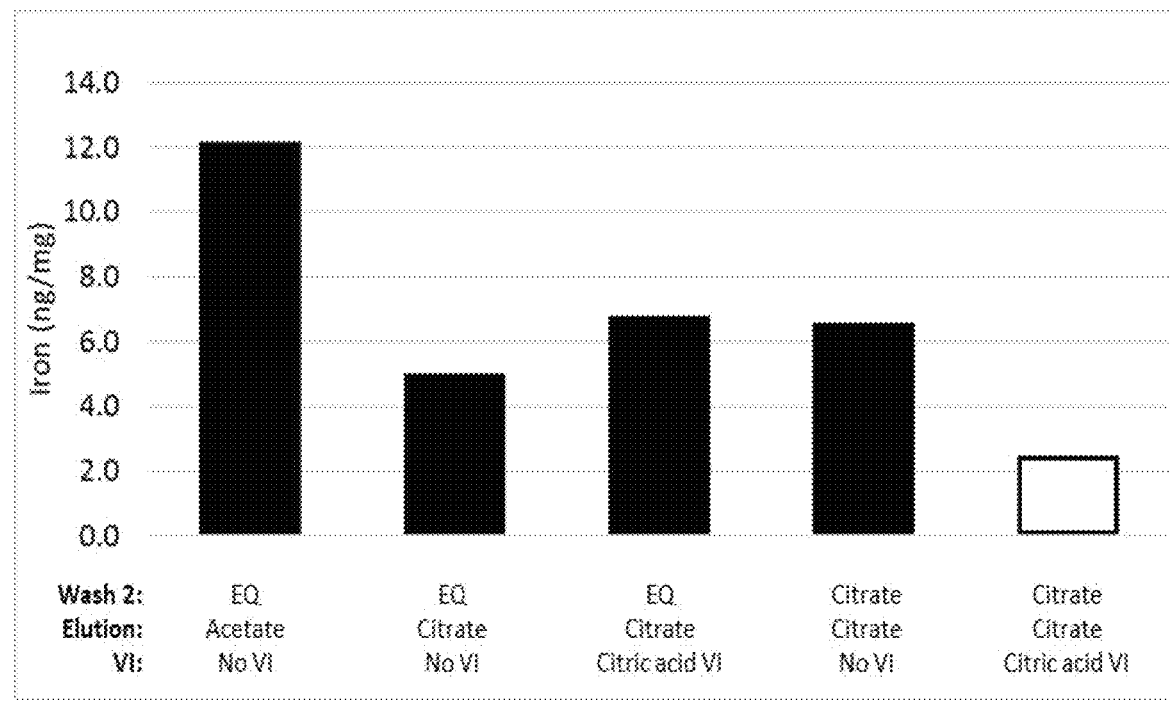
FIG. 16 illustrates iron levels of CEX eluant pools from a RoboColumn® screen evaluating citrate as a Protein A Wash 2 buffer, Protein A elution buffer, and low pH viral inactivation titrant. A white bar indicates that no iron was detected.

The observation of a combined effect of citrate and lower pH led to a study comparing the benefits of using citrate in the low pH elution step and the subsequent low pH hold for viral inactivation (see, schematic of experiments in FIG. 15). Two bench scale Protein A runs were performed using a 25 mM citrate elution at pH 3.6, either with a 200 mM citrate Wash 2 or a EQ Wash 2. Aliquots of the resulting elution pools were divided in two, and half of each elution pool was titrated to pH 3.5 for a 1-hour viral inactivation hold using citric acid while the other half was neutralized to pH 5.0. All four subsequent pools were run on CEX RoboColumns® to remove any iron that had been chelated from of the product. The CEX pools were submitted for ICP-MS analysis along with a control CEX pool using the EQ Wash 2 and sodium acetate elution (see, FIG. 16). The results demonstrate that the addition of the citrate elution significantly reduced the amount of iron bound to the product. Additionally, the combination of the citrate wash, elution and low pH viral inactivation resulted in removal of iron to below the limit of detection.

Figure 17:
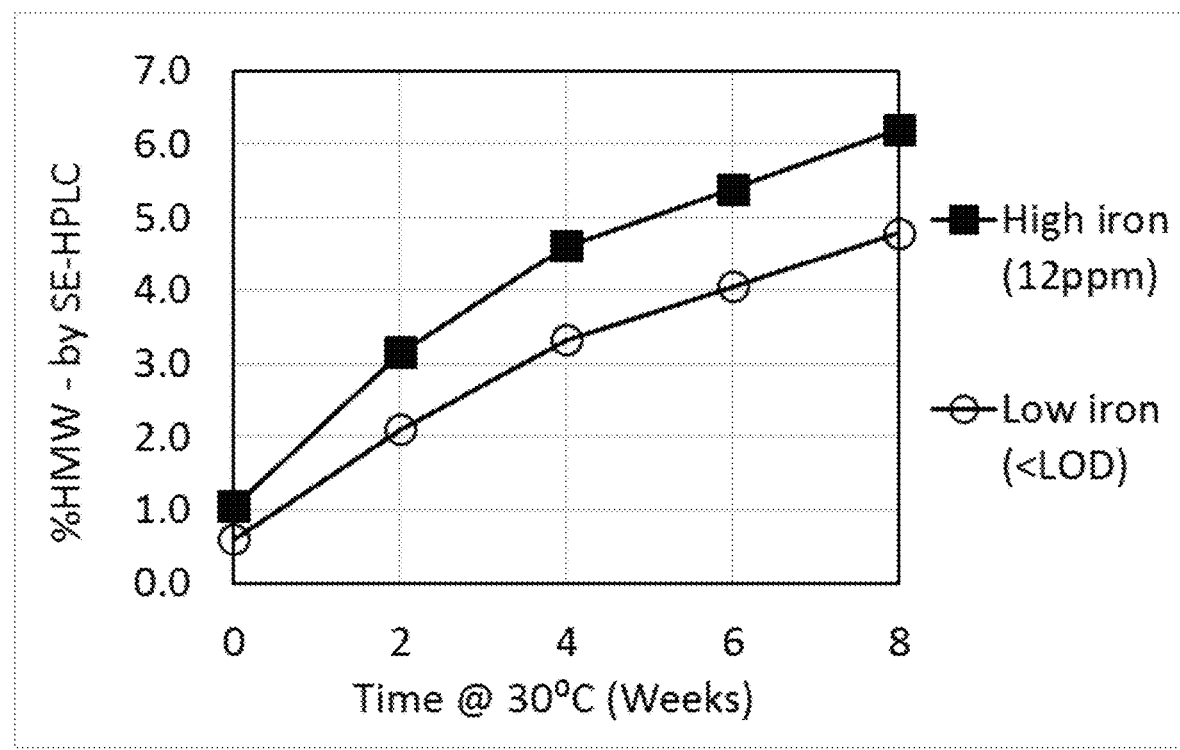
FIG. 17 shows a comparison of high molecular weight (HMW) levels over time in high iron and low iron samples, respectively, held at 30° C. for accelerated stability.
Figure 18:
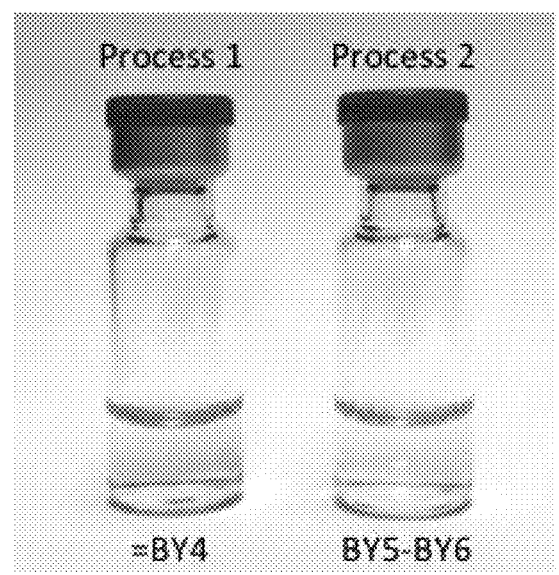
FIG. 18 shows a visual comparison of the formulated high iron sample (process 1) and low iron sample (process 2).

Next, samples of the high iron pool (EQ Wash 2, acetate elution, and no low pH VI) and the low iron pool (citrate Wash 2, citrate elution, and citric acid low pH VI) were placed on accelerated stability to determine if the presence of iron would affect product stability. The samples were formulated into 10 mM phosphate, 40 mM NaCl, 5% (w/v) sucrose and 0.03% PS-20 at a concentration of 40 g/L and held at 30° C. Time points were taken every two weeks and tested for high molecular weight (HMW) species by analytical SEC. The data are shown in FIG. 17. The high iron sample had a greater rate of HMW increase and also a brownish color as compared to the low iron sample (see, FIG. 18). The color of high iron sample is equivalent to the brown/yellow 4 standard (BY4), while the color of the low iron sample is between the brown/yellow 5 and 6 standards (BY5 and BY6).

Example 4: Galectin and Metallic Cation Removal Across a Downstream Process

Figure 19:
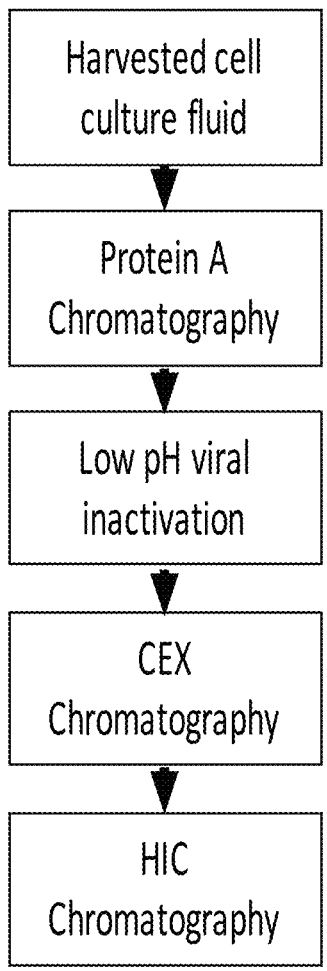
FIG. 19 shows a schematic flow diagram of an exemplary embodiment of the inventive method used to purify a glycosylated recombinant protein of interest from CHO galectin-3 and iron.

Purification of glycosylated recombinant aflibercept by removal of CHO galectin-3 and iron cations from the recombinant aflibercept was evaluated across a three column downstream process which incorporated several of the techniques outlined above in combination in an exemplary embodiment of the present invention. Schematically, the process flow is shown in FIG. 19.

Chromatography runs were performed at bench scale as described in Example 1, above, and the columns were loaded to capacity: 19 g/L resin for Protein A, 30 g/L resin for CEX, and 100 g/L resin for HIC. For galectin-3 removal, the process included a 2 M $CaCl_2$) Wash 2 for the Protein A step, CEX chromatography at pH 5.0 with Fractogel® $SO_3^-$ resin, and an HIC step with Butyl 650M resin. For iron removal, the process included a 25 mM citrate elution for Protein A and a citric acid titration for viral inactivation in order to chelate the iron away from the product. Chelated iron was then removed by the CEX step.

The results demonstrate that galectin-3 is effectively removed by the process, from >667 ppm in the harvested cell culture fluid (HCCF) to non-detectible levels in the HIC pool (see, Table 6, below). The HIC step was the most effective but the Protein A and CEX steps also contributed significantly. Iron was also effectively removed, from 1022 ppb in the HCCF, to 5 ppb in the CEX pool.

The combination of Protein A/VI and CEX steps contributed to iron removal. These data demonstrate that the steps of the method outlined above provided significant removal of galectin-3 and iron cation impurities.

TABLE 6

CHO galectin-3 and iron levels in product pools purified by an embodiment of the three-column inventive method developed to remove these contaminants.

| Step | Galectin-3 (ng/mg) by ELISA | Galectin-3 (ppm) by ELISA | Iron (ug/L) by ICP-MS | Iron (ppb) by ICP-MS |
|---|---|---|---|---|
| Harvested cell culture fluid | >596* | >677 | 891 | 1022 |
| Protein A VI pool | 550 | 42 | 502 | 38 |
| CEX pool | 136 | 32 | 21 | 5 |
| HIC pool | 0.1 | 0.0 | Not tested | |

VI = viral inactivation.
*Level of galectin-3 in the Protein A flow-through fraction.

Example 5: Eliminating Other Sources of Metal Cation Contaminants in the Process Metal Analysis of Water and Buffer Samples.

Figure 20:
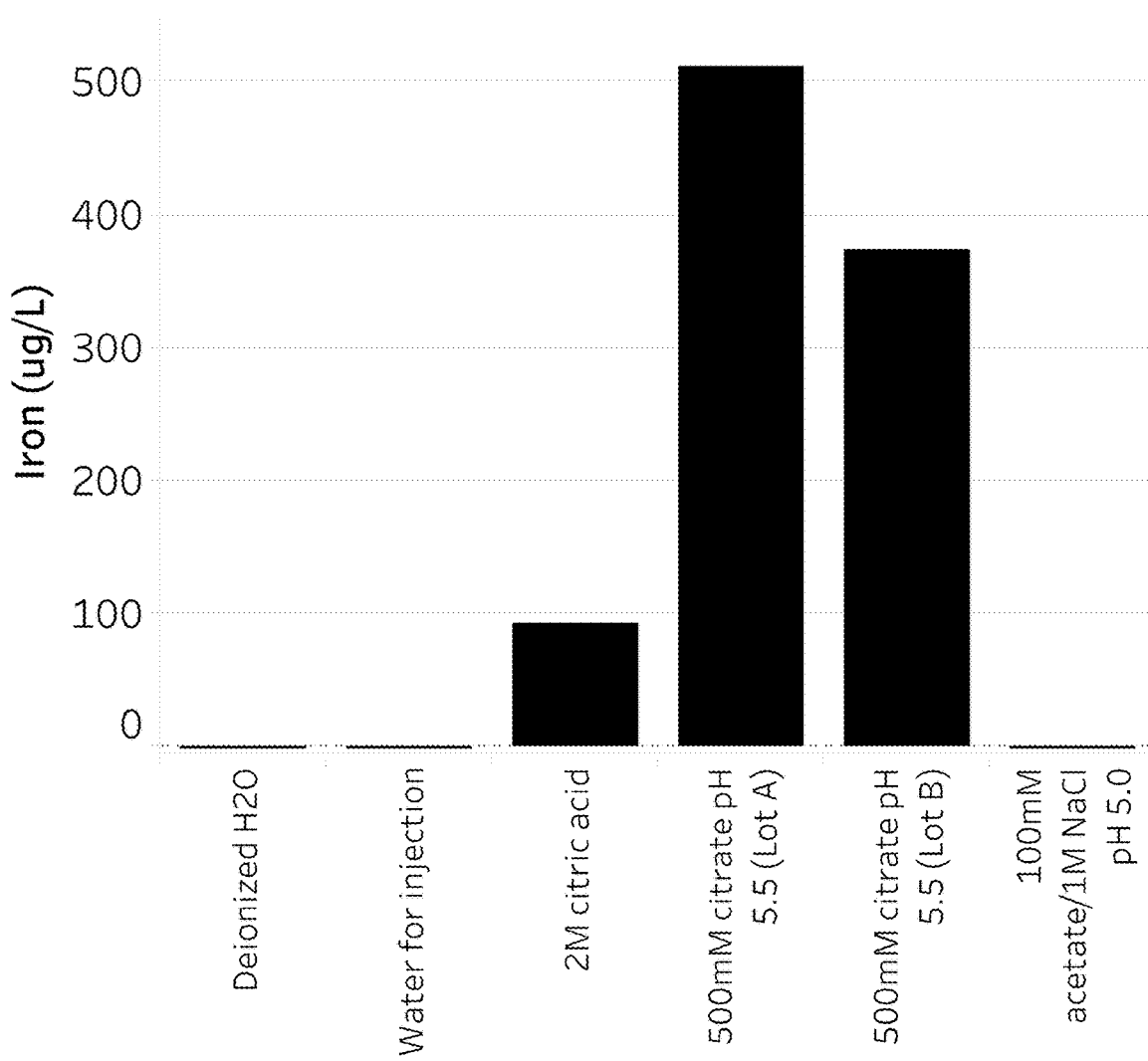
FIG. 20 shows concentrations (μg/L) of iron in water and buffer samples quantitated by ICP-MS.
Figure 21:
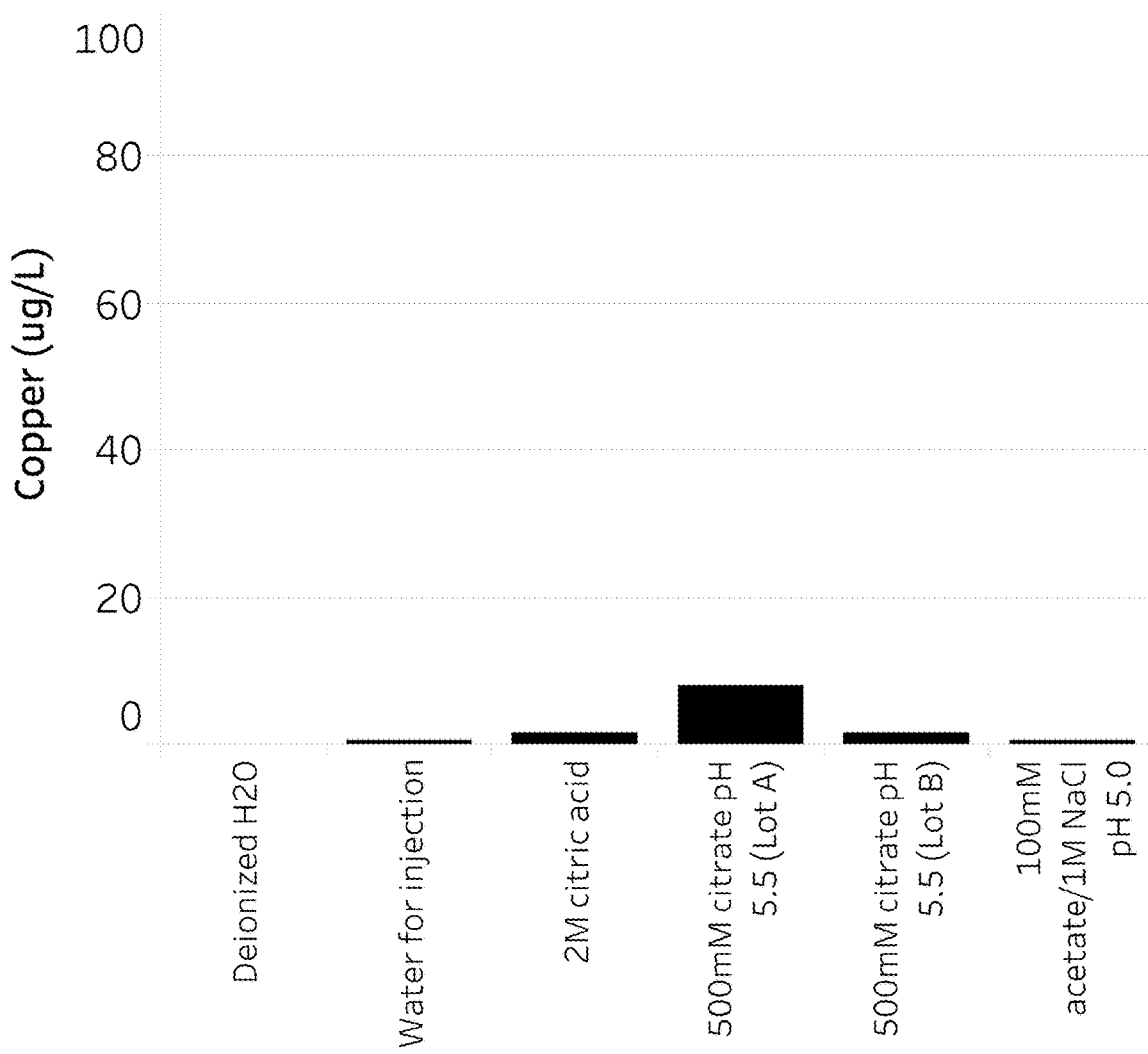
FIG. 21 shows concentrations (μg/L) of copper in water and buffer samples quantitated by ICP-MS.
Figure 22:
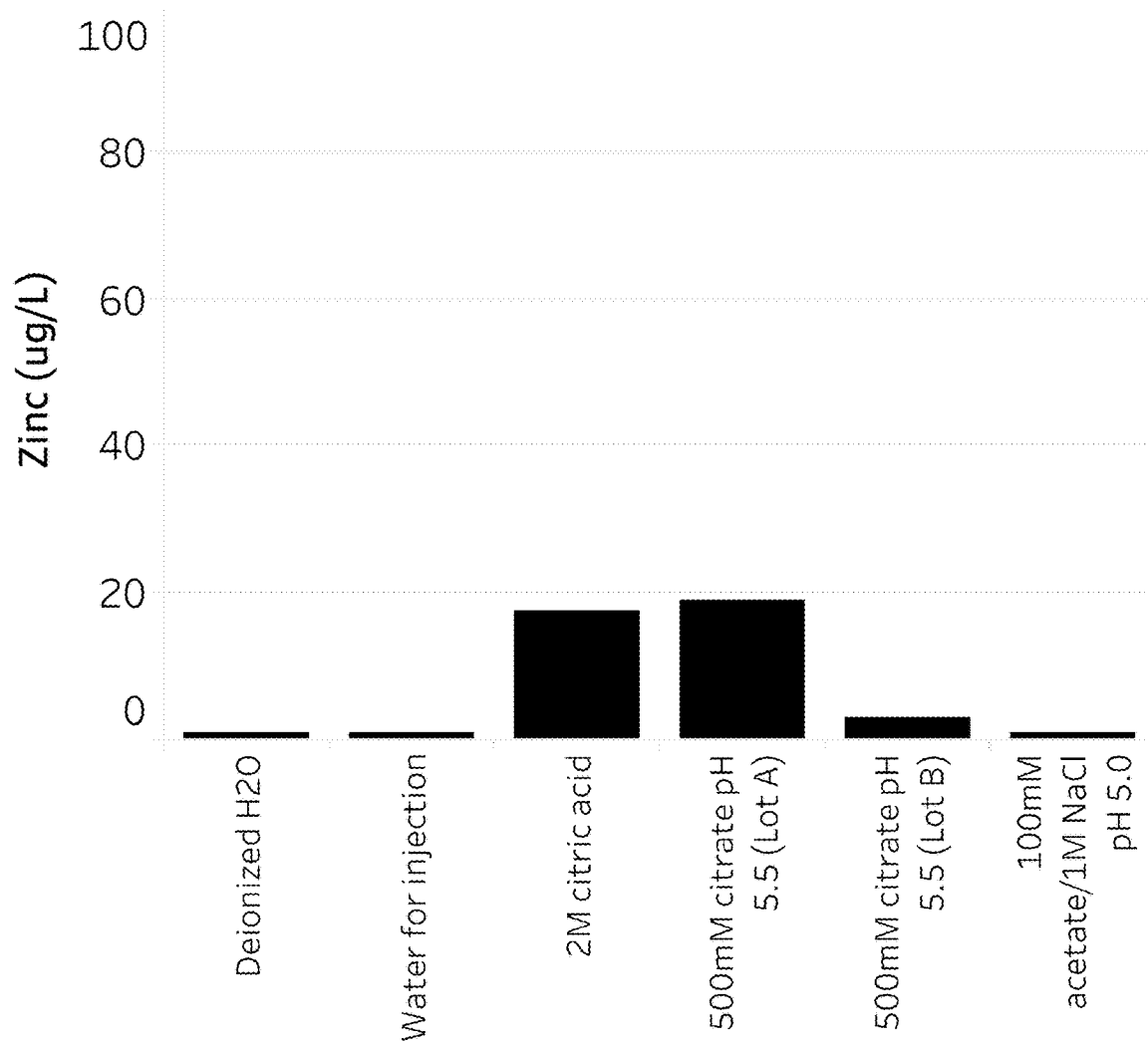
FIG. 22 shows concentrations (μg/L) of zinc in water and buffer samples quantitated by ICP-MS.

To understand potential sources of iron and other metal contaminants in the process, water and buffer samples were evaluated for iron, copper and zinc by ICP-MS as described above. Results are shown in FIG. 20, FIG. 21, and FIG. 22, respectively. The water samples had very low to non-detectible levels of the 3 metals, while the 2 M citric acid and the 500 mM citrate buffer showed significant levels of iron contamination, plus some copper and zinc. The citrate buffer had higher levels of iron than the citric acid, suggesting that the sodium citrate component may have more metal contamination than the acid form. Since citrate is a metal chelator, it is possible that the metal contamination occurs during the manufacture of these chemicals.

Metal Contamination in a Diatomaceous Earth Depth Filter.

Figure 23:
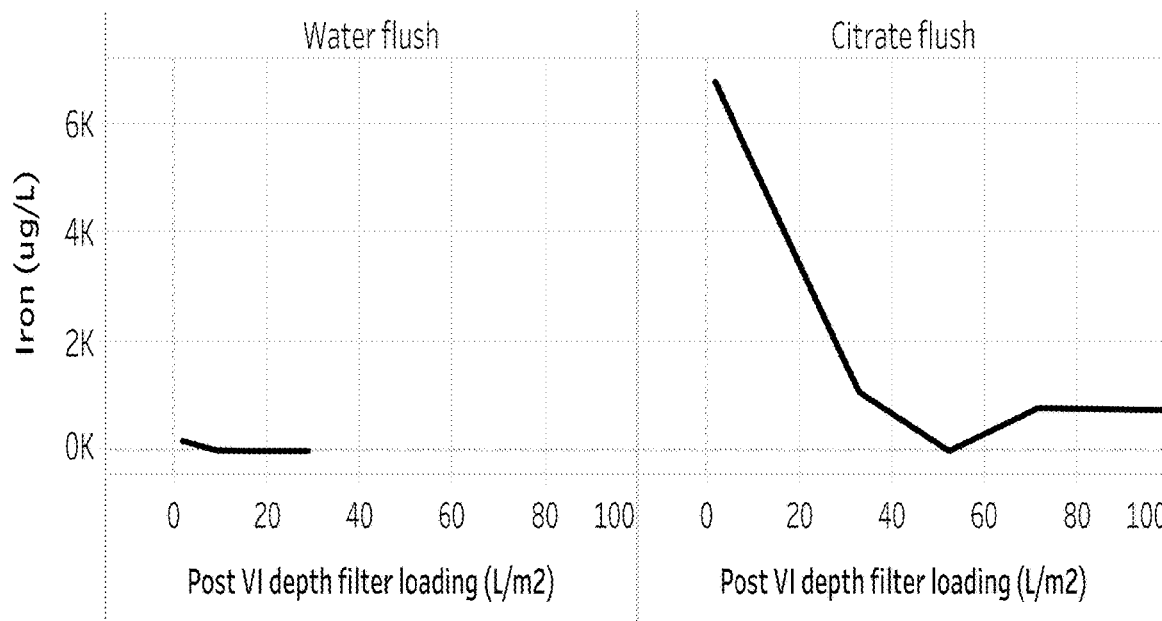
FIG. 23 shows concentrations (μg/L) of iron observed in diatomaceous earth (DE) depth filter fractions from a water flush and a citrate buffer flush.
Figure 24:
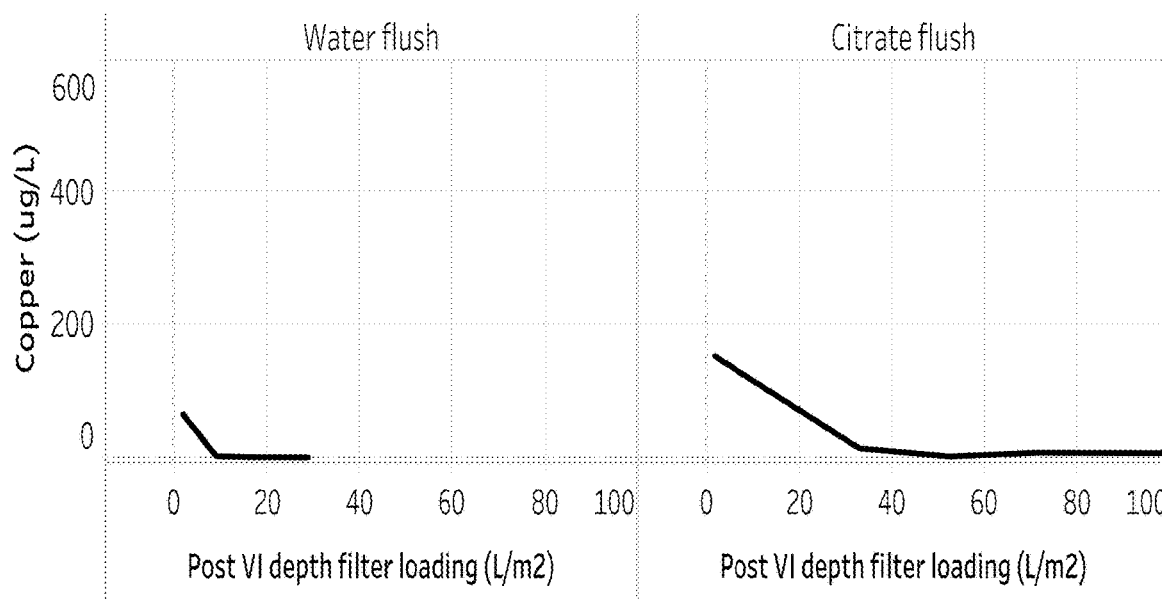
FIG. 24 shows concentrations (μg/L) of copper observed in diatomaceous earth (DE) depth filter fractions from a water flush and a citrate buffer flush.
Figure 25:
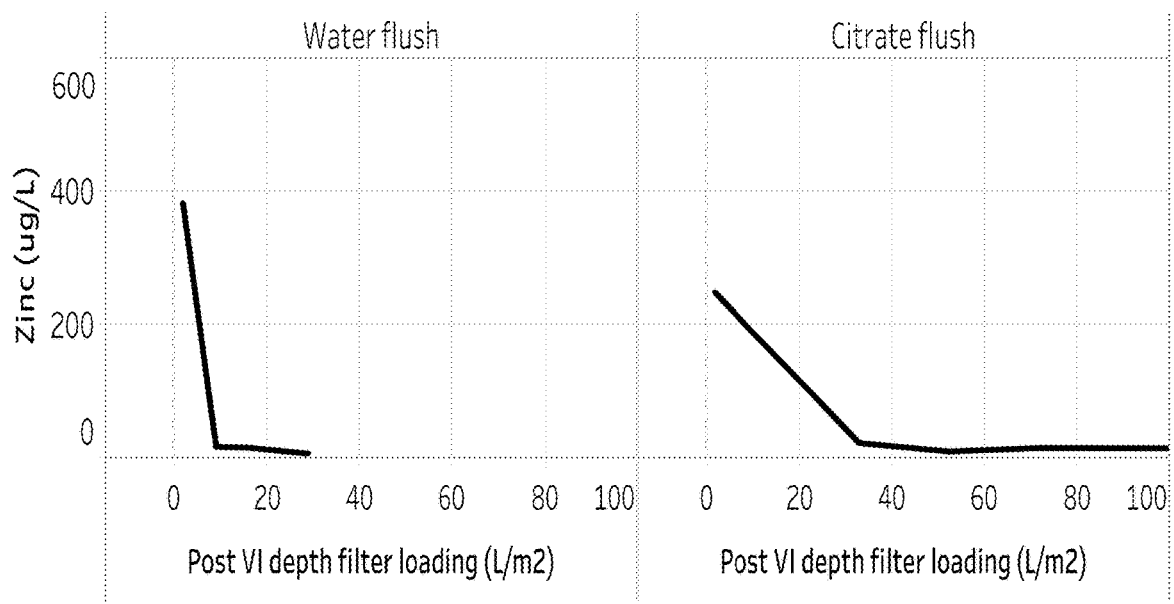
FIG. 25 shows concentrations (μg/L) of zinc observed in diatomaceous earth (DE) depth filter fractions from a water flush and a citrate buffer flush.

To determine whether a diatomaceous earth (DE) depth filter could be a source of metal cation contamination, we performed a filter flush study using a 0.0023 cm$^2$ Millipore A1HC depth filter. The filter was flushed with water at 30 L/m$^2$ followed by 500 mM citrate pH 5.5 at >100 L/m$^2$. Four to five 4-mL fractions of filtrate were collected during each flush and analyzed for iron, copper and zinc by ICP-MS. Results are shown in FIG. 23, FIG. 24, and FIG. 25, respectively. With the water flush, some iron, copper and zinc cations were eluted from the filter and the levels of these metals returned to baseline after 10 L/m$^2$ of water had been flushed through the filter. Subsequently flushing the filter with 0.5 M citrate pH 5.5 resulted in additional elution of all three metals, including high levels of iron (>6000 μg/L). These data indicate that the citrate buffer can likely chelate additional metal cations from the filter. The metal levels returned to baseline (i.e. the level of metal present in the buffer) after ~50 L/m$^2$ of buffer. These results imply that DE can be a significant source of metal cation contamination, including iron, which could be exacerbated by the presence of citrate in the Protein A pool from the use of citrate containing elution buffer or use of citric acid for viral inactivation.

Evaluation of Iron, Copper and Zinc Cation Removal Using Different Protein a Elution and Depth Filter Flush Buffers.

Figure 26:
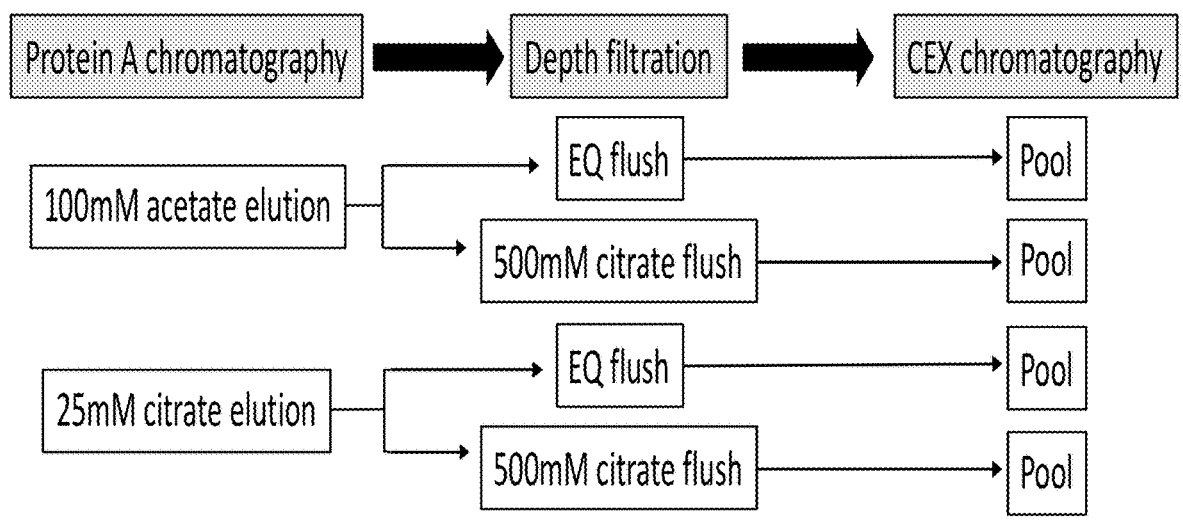
FIG. 26 is a schematic representation of an experimental sequence incorporating, between the Protein A affinity chromatography and CEX chromatography steps, an optional depth filtration step, with either an equilibration buffer (EQ) or citrate buffer flush through the diatomaceous earth in the depth filter, as described in Example 5 herein.
Figure 27:
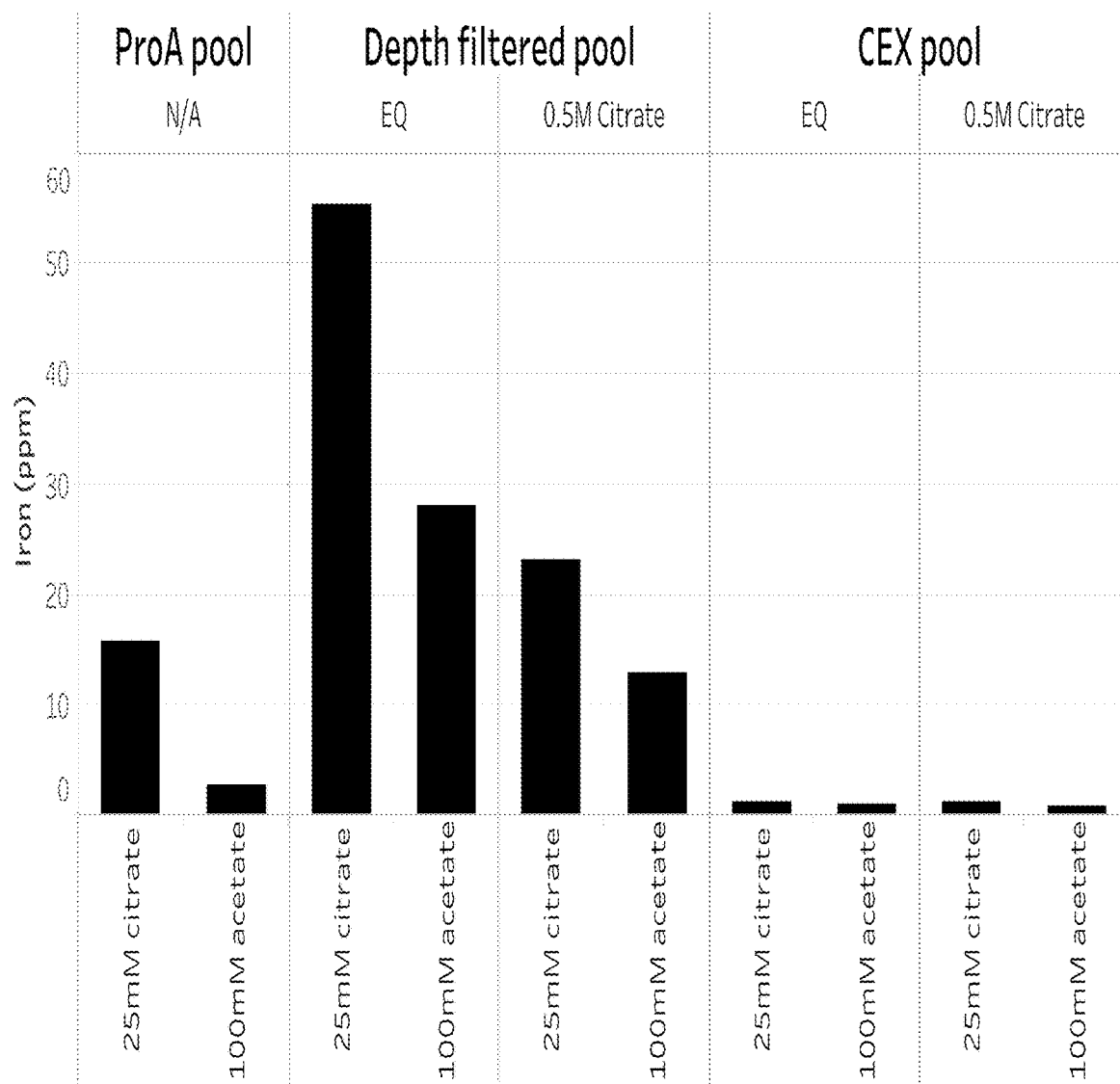
FIG. 27 shows levels (ppm) of iron observed in Protein A, depth filter and CEX pools with different Protein A elution and depth filter flush conditions.
Figure 28:
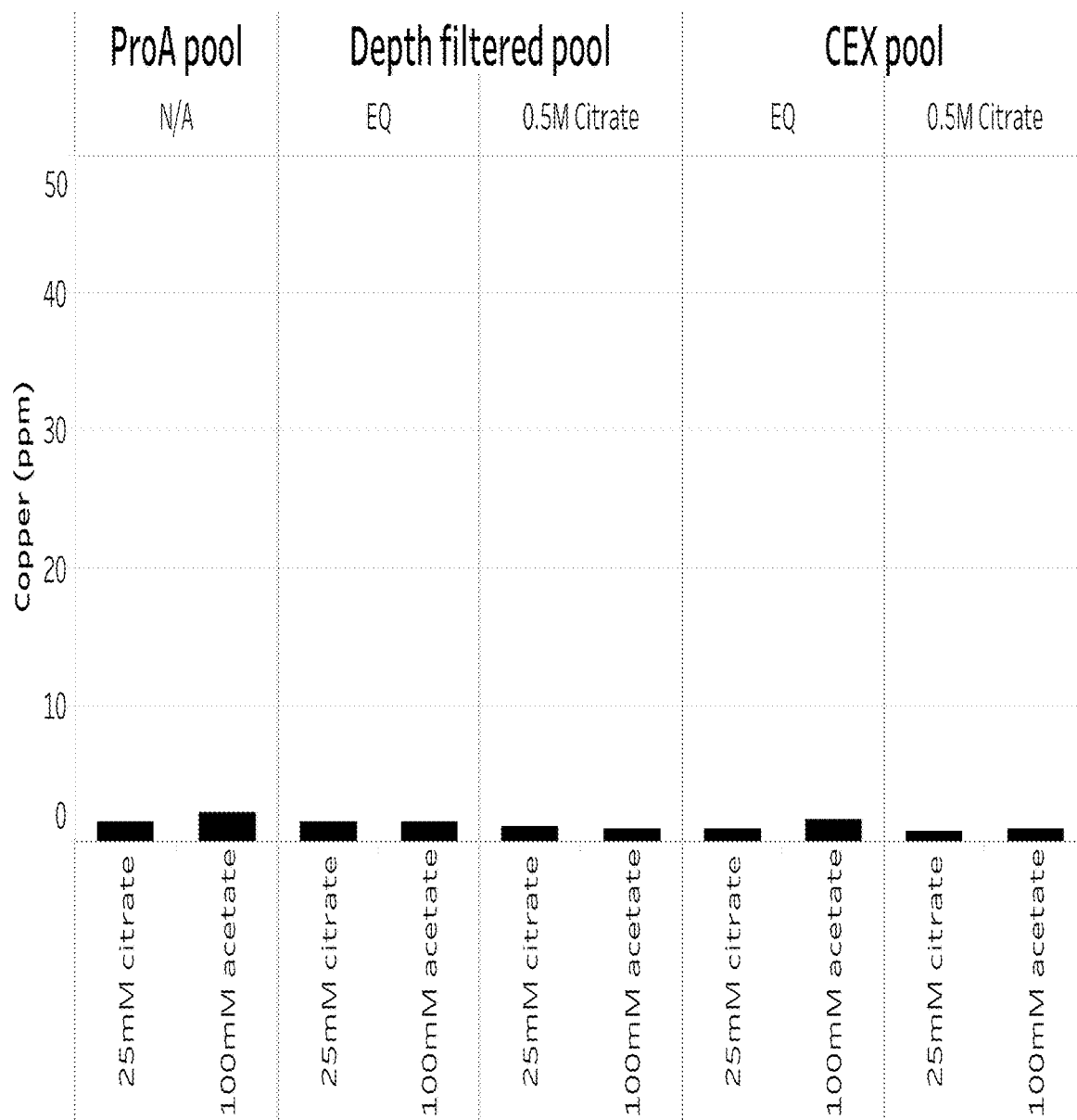
FIG. 28 shows levels (ppm) of copper observed in Protein A, depth filter and CEX pools with different Protein A elution and depth filter flush conditions.
Figure 29:
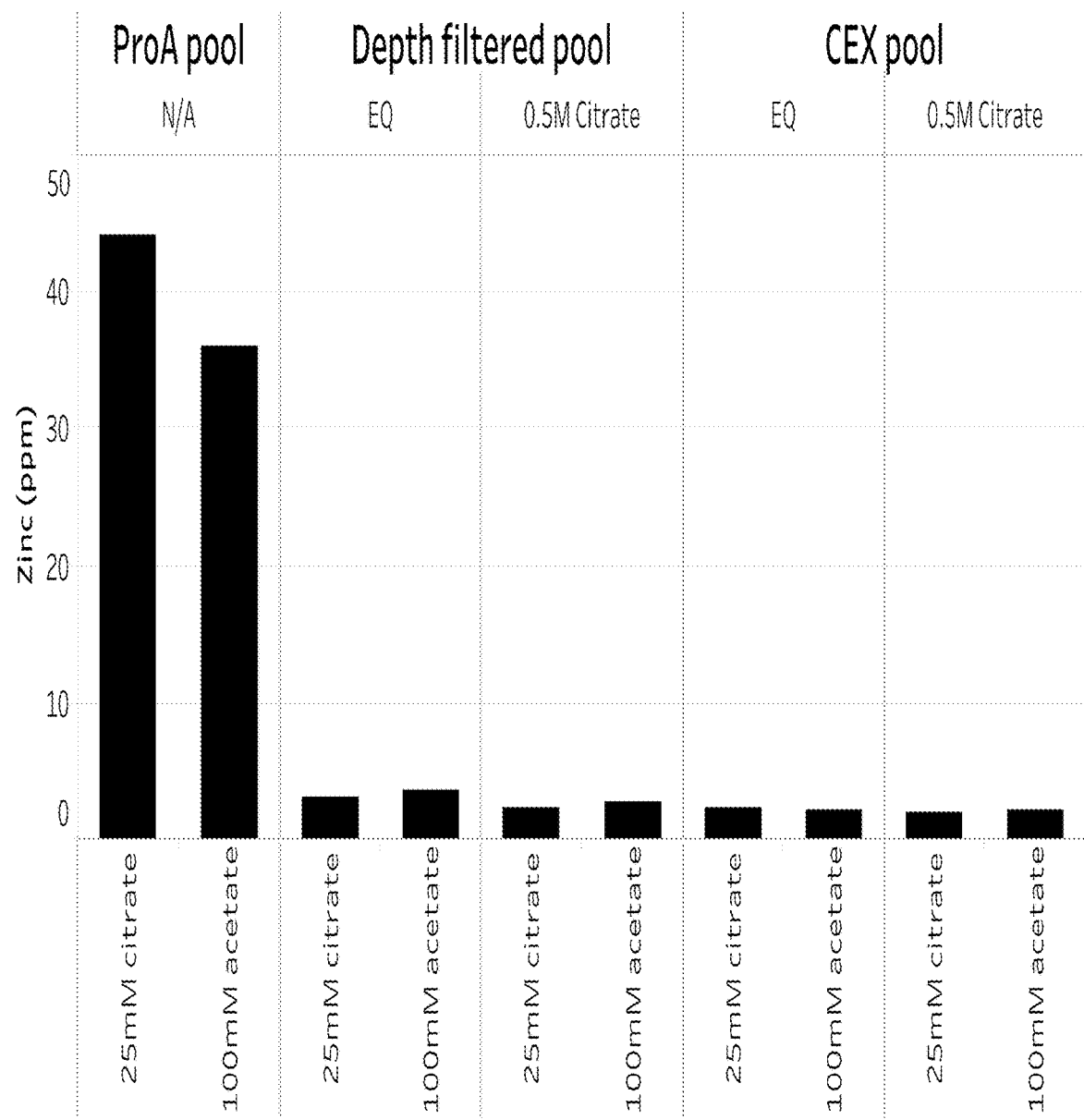
FIG. 29 shows levels (ppm) of zinc observed in Protein A, depth filter and CEX pools with different Protein A elution and depth filter flush conditions.

We evaluated the ability of the inventive method to remove iron, copper and zinc cations from a protein of interest using a series of three steps: Protein A chromatography, depth filtration with an A1HC depth filter, and CEX chromatography (FIG. 26). As part of the experiment, we tested the impact on metal removal of two different Protein A elution buffers, 100 mM acetate, pH 3.6 and 25 mM citrate, pH 3.6, and two different depth filter flush buffers, equilibration (EQ) buffer alone (100 mM acetate, pH 5.0) and 500 mM citrate, pH 5.5, followed by an EQ flush. Iron, copper, and zinc cation levels were quantitated in the Protein A eluant pool ("ProA pool"), Protein A eluant pool subjected to depth filtration ("depth filtered pool"), and CEX eluant pool ("CEX pool") using ICP-MS; results are shown in FIG. 27, FIG. 28, and FIG. 29, respectively.

Use of 100 mM acetate buffer for Protein A elution resulted in lower levels of iron and zinc cations in the Protein A eluant pool, compared to a 25 mM citrate buffer elution, while the levels of copper were low and unchanged. When the pools were filtered over the depth filter, the levels of iron increased in all cases, likely due to iron cation contamination from the filter. Pre-conditioning the depth filter by pre-flushing with 500 mM citrate buffer lowered the iron level of the depth filter pool, and that condition coupled with the 100 mM acetate Protein A elution buffer provided additional reduction of the quantity of iron cations. Levels of copper and zinc cations remained low under all depth filtered conditions.

Purification of the POI in the depth filter pools by CEX chromatography removed a significant amount of iron cation, with all conditions containing around 1 ppm of iron. For zinc and copper cations, all of the conditions had low levels (1-2 ppm) similar to those observed in the depth filter pool. Taken together, these data indicate that use of the 100 mM acetate Protein A elution buffer coupled with a citrate buffer depth filter pre-conditioning flush can significantly reduce iron cation contamination in the purification process through the depth filter pool stage. Zinc cation levels were reduced by the acetate buffer Protein A elution in the Protein A eluant pool stage, while copper cation levels remained low and relatively unaffected in all conditions.

We claim:

1. A method for purifying a glycosylated recombinant protein of interest from a contaminant, comprising:
   (a) loading onto a Protein A matrix, at about neutral pH, a host cell culture supernatant or filtrate comprising the glycosylated recombinant protein of interest (POI) and a galectin host cell protein (HCP) contaminant, comprising galectin-3, wherein the POI comprises the $C_H2$ and $C_H3$ domains of an immunoglobulin Fc domain and one or more terminal beta-galactosyl residues to which the galectin-3 is reversibly bound;
   (b) washing the Protein A matrix that has the POI bound to it, with a buffer at about pH 6.0-6.5, comprising 1-3 M calcium chloride;
   (c) eluting the POI from the Protein A matrix with a buffer comprising citric acid or a citrate salt below about pH 4 into an eluant pool, and:
      (i) if the eluant pool is more basic than the pH range of pH 3.3-3.7, titrating the eluant pool to pH 3.3-3.7 with citric acid, and
      (ii) optionally, keeping the eluant pool at pH 3.3-3.7 for a period sufficient for viral inactivation;
   (d) binding the POI in the eluant pool from (c) to a cation exchange matrix (CEX) in a low conductivity buffer of about 2-15 mS, at pH 5.0-5.5;
   (e) eluting the POI from the cation exchange matrix with an electrolyte concentration gradient of increasingly higher conductivity, up to about 40-100 mS, into a CEX eluant pool; and
   (f) loading the CEX eluant pool onto a hydrophobic interaction chromatography (HIC) matrix in a high conductivity buffer, about 40-100 mS in conductivity, or greater, at pH 5.0-6.0 and washing the HIC matrix, whereby the POI is separated from the galectin-3.

2. The method of claim 1, wherein in (b) washing the Protein A matrix that has the POI bound to it, is with a buffer comprising 2 to 2.7 M calcium chloride.

3. The method of claim 1, wherein the POI is selected from aflibercept, alefacept, etanercept, abatacept, belatacept, rFVIIIFc, rFIXFc, and rilonacept.

4. The method of claim 3, wherein the POI is aflibercept.

5. The method of claim 1, wherein the host cell culture supernatant or filtrate further comprises a metallic cation contaminant, and wherein the POI is also separated from the metallic cation contaminant.

6. The method of claim 5, wherein the metallic cation contaminant is selected from aluminum, barium, calcium, cobalt, copper, zinc, iron, magnesium, manganese, mercury, nickel, and strontium cations.

7. The method of claim 6, wherein the metallic cation contaminant is an iron cation.

8. The method of claim 1, further comprising: before binding the POI in the eluant pool from (c) to a cation exchange matrix, subjecting the eluant pool to depth filtration comprising filtration through diatomaceous earth.

9. The method of claim 8, wherein the diatomaceous earth was pre-conditioned with a citrate buffer.

* * * * *

SEQUENCE LISTING

```
<160> NUMBER OF SEQ ID NOS: 1

<210> SEQ ID NO 1
<211> LENGTH: 431
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1
```

-continued

```
Ser Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys Asp Lys Thr
        195                 200                 205

His Thr Cys Pro Pro Cys Pro Ala Pro Glu Leu Leu Gly Gly Pro Ser
210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Asp Glu Leu Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
370                 375                 380

Ser Asp Gly Ser Phe Phe Leu Tyr Ser Lys Leu Thr Val Asp Lys Ser
385                 390                 395                 400
```

-continued

```
Arg Trp Gln Gln Gly Asn Val Phe Ser Cys Ser Val Met His Glu Ala
            405                 410                 415

Leu His Asn His Tyr Thr Gln Lys Ser Leu Ser Leu Ser Pro Gly
            420                 425             430
```